US007115740B2

(12) United States Patent
Chen et al.

(10) Patent No.: US 7,115,740 B2
(45) Date of Patent: Oct. 3, 2006

(54) PYRIMIDO COMPOUNDS HAVING ANTIPROLIFERATIVE ACTIVITY

(75) Inventors: Yi Chen, Nutley, NJ (US); Apostolos Dermatakis, Parlin, NJ (US); Jin-Jun Liu, Warren, NJ (US); Kin-Chun Luk, North Caldwell, NJ (US); Christophe Michoud, New York, NY (US); Pamela Loreen Rossman, Nutley, NJ (US)

(73) Assignee: Hoffmann-la Roche Inc., Nutley, NJ (US)

( * ) Notice: Subject to any disclaimer, the term of this patent is extended or adjusted under 35 U.S.C. 154(b) by 145 days.

(21) Appl. No.: 10/817,697

(22) Filed: Apr. 2, 2004

(65) Prior Publication Data
US 2004/0204427 A1    Oct. 14, 2004

Related U.S. Application Data

(60) Provisional application No. 60/461,694, filed on Apr. 10, 2003.

(51) Int. Cl.
*C07D 487/04* (2006.01)
*C07D 239/47* (2006.01)
*C07D 407/12* (2006.01)
*A61K 31/519* (2006.01)
*A61P 35/00* (2006.01)

(52) U.S. Cl. ............. 544/256; 544/317; 514/262.1
(58) Field of Classification Search ........... 544/256, 544/317; 514/262.1
See application file for complete search history.

(56) References Cited

U.S. PATENT DOCUMENTS

| 2,949,466 A | 8/1960 | Hoefle et al. |
| 3,939,084 A | 2/1976 | Sullivan |
| 4,425,346 A | 1/1984 | Horlington |
| 4,886,807 A | 12/1989 | Kitamura et al. |
| 6,150,373 A | 11/2000 | Harris et al. |
| 6,451,804 B1 | 9/2002 | Dunn et al. |
| 2004/0019210 A1 | 1/2004 | Connolly et al. |
| 2004/0097485 A1 | 5/2004 | Burkitt et al. |

FOREIGN PATENT DOCUMENTS

| WO | WO 98/24432 | 6/1998 |
| WO | WO 99/61444 | 12/1999 |
| WO | WO 00/24744 | 5/2000 |
| WO | WO 01/29041 | 4/2001 |
| WO | WO 01/29042 | 4/2001 |
| WO | WO 01/64679 | 9/2001 |
| WO | WO 02/18380 | 3/2002 |
| WO | WO 03/062236 | 7/2003 |

OTHER PUBLICATIONS

Draetta, G. and Pagano, M. in "Annual Reports in Medicinal Chemistry, vol. 31", 1996, Academic Press, San Diego, p. 241-246.*
Noble, M.E.M. et al, Science, vol. 303, 2004, pp. 1800-1805.*
Anderson, M.R. et al, Expert Opin. Investig. Drugs, 2003, 12(4) 577-592.*
Laird, A.D. et al, Expert opin. Investig. Drugs, 2003, 12(1), 51-64.*
Traxler, Peter, Expert Opin. Ther. Targets, 2003, 7(2) 215-234.*
Boschelli, et al., *Drugs of the Future, 2000* 25(7) pp. 717-736.
Alexander J. et al., *J. Med. Chem. 1988*, vol. 31, pp. 318-322.
Masquelin et al., *Helvetica Chimica Acta*, vol. 81 (1998) pp. 646-659.
Devi et al., *Indian Journal of Heterocyclic Chemistry*, vol. 7, Jan.-Mar. 1998, pp. 193-196.
Tominaga et al., *Chemical& Pharmaceutical Bulletin*, vol. 32, No. 1, Jan. 1984, pp. 122-129.
Tominaga et al., *Heterocycles*, vol. 12, No. 4. 1979, pp. 503-504.
Marsh, et al., *Chemical Communications*, 1996, pp. 1527-1528.
Z. Chem. 20 Jg (1980) Heft. 11, pp. 412-413.
Cappuccino et al., *Cancer Research*, vol. 24, Aug. 1964, pp. 1243-1248.
Chatterjee et al., *J. Sci. Industr. Res.*, vol. 17B, Feb. 1958, pp. 63-70.
Chatterjee et al., *J. Sci. Industr. Res.*, vol. 18B, Jul. 1959, pp. 272-278.
Graboyes et al., *Pteridines X.*, vol. 11 Jan. 6, 1968, pp. 568-573.
Grohe et al., *Liebigs Ann. Chem.*, 1974, pp. 2066-2073.
Gulevskaya et al., *Chemistry of Heterocyclic Compounds*, vol. 30, No. 9, 1994, pp. 1083-1091.
Hirota et al., *J. Chem. Soc. Perkin Trans. 1*, 1990, pp. 123-128.
Srivastava et al., *Combinatorial Chemistry & High Throughout Screening*, 1999, 2, pp. 33-37.
Taylor, *Pyrimido [4,5-D]Pyrimidines*, vol. 82, pp. 5711-5718.
Wamhoff et al., *Heterocycles*, vol. 35, No. 2, 1993, pp. 1055-1066.
Hirota, M. et al. *"A Facile Synthesis of 7-Substituted Pyrimido[4,5-d]-Pyrimidine-2, 4-diones"*, Synthesis, pp. 589-590 (1984).

* cited by examiner

*Primary Examiner*—Thomas C. McKenzie
(74) *Attorney, Agent, or Firm*—George W. Johnston; Patricia S. Rocha-Tramaloni

(57) ABSTRACT

Disclosed are novel pyrimido compounds that are selective inhibitors of both KDR and FGFR kinases. These compounds and their pharmaceutically acceptable salts are antiproliferative agents useful in the treatment or control of solid tumors, in particular breast, colon, lung and prostate tumors. Also disclosed are pharmaceutical compositions containing these compounds and methods of treating cancer.

30 Claims, No Drawings

PYRIMIDO COMPOUNDS HAVING ANTIPROLIFERATIVE ACTIVITY

PRIORITY TO RELATED APPLICATIONS

This application claims the benefit of Provisional Application Ser. No. 60/461,694, filed Apr. 10, 2003.

FIELD OF THE INVENTION

The present invention is directed to novel pyrimido compounds that inhibit KDR (kinase insert domain-containing receptor) and FGFR (fibroblast growth factor receptor) kinases. These compounds and their pharmaceutically acceptable salts have antiproliferative activity and are useful in the treatment or control of cancer, in particular solid tumors. In addition these compounds have advantageous bioavailability profiles. This invention is also directed to pharmaceutical compositions containing such compounds and to methods of treating or controlling cancer, most particularly the treatment or control of breast, lung, colon and prostate tumors.

BACKGROUND OF THE INVENTION

Protein kinases are a class of proteins (enzymes) that regulate a variety of cellular functions. This is accomplished by the phosphorylation of specific amino acids on protein substrates resulting in conformational alteration of the substrate protein. The conformational change modulates the activity of the substrate or its ability to interact with other binding partners. The enzyme activity of the protein kinase refers to the rate at which the kinase adds phosphate groups to a substrate. It can be measured, for example, by determining the amount of a substrate that is converted to a product as a function of time. Phosphorylation of a substrate occurs at the active-site of a protein kinase.

Tyrosine kinases are a subset of protein kinases that catalyze the transfer of the terminal phosphate of adenosine triphosphate (ATP) to tyrosine residues on protein substrates. These kinases play an important part in the propagation of growth factor signal transduction that leads to cellular proliferation, differentiation and migration.

For example, fibroblast growth factor (FGF) and vascular endothelial growth factor (VEGF) have been recognized as important mediators of tumor promoted angiogenesis. VEGF activates endothelial cells by signaling through two high affinity receptors, one of which is the kinase insert domain-containing receptor (KDR). See Hennequin L. F. et. al., J. Med. Chem. 2002, 45(6), pp1300. FGF activates endothelial cells by signaling through the FGF receptor (FGFR). Solid tumors depend upon the formation of new blood vessels (angiogenesis) to grow. Accordingly, inhibitors of the receptors FGFR and KDR that interfere with the growth signal transduction, and thus slow down or prevent angiogenesis, are useful agents in the prevention and treatment of solid tumors. See Klohs W. E. et. al., Current Opinion in Biotechnology 1999, 10, p. 544.

There are several examples of small molecule inhibitors of protein kinase catalytic activity. In particular, small molecule inhibitors typically block the phosphorylation of substrates by tightly interacting with the protein kinase ATP binding site (or "active site"). See WO 98/24432 and Hennequin L. F. et. al., J. Med. Chem. 2002, 45(6), pp3100. Several of these compounds inhibit multiple targets. For example, WO99/61444 (Warner-Lambert) discloses bicyclic pyrimidines and bicyclic 3,4-dihydropyrimidines of formula

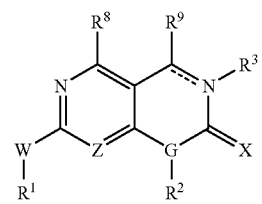

that are asserted to inhibit cyclin dependent kinases Cdk1, Cdk2 and Cdk4 as well as the growth factor receptor tyrosine kinase enzymes PDGFR and FGFR. Some compounds are also asserted to inhibit Cdk6.

U.S. Pat. No. 6,150,373 (Hoffmann-La Roche Inc.) discloses bicyclic nitrogen heterocycles of formula

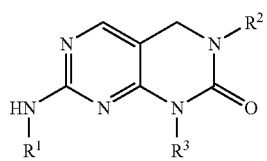

that are stated to inhibit the T-cell tyrosine kinase $p56^{lck}$.

WO 01/29041 A1 and WO 01/29042 (F. Hoffmann-La Roche AG) disclose alkylamino substituted bicyclic nitrogen heterocycles of formula

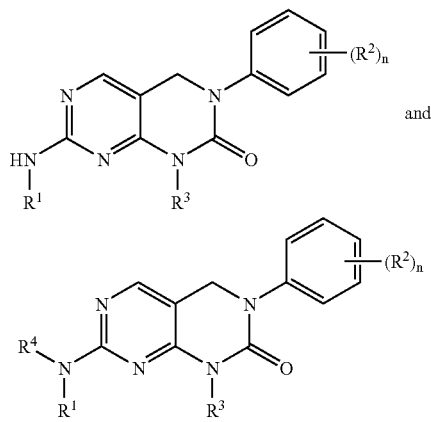

that are stated to inhibit p38 mediated cellular functions and are thus inhibitors of cellular proliferation.

WO 01/64679 A1 (SmithKline Beecham) discloses 1,5-disubstituted-3,4-dihydro-1H-pyrimido[4,5-D]pyrimidin-2-one compounds of formula

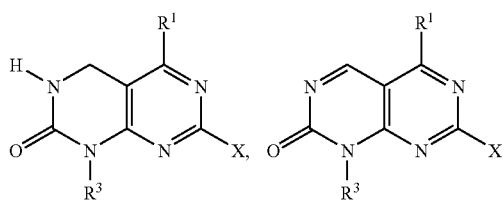

that are stated to be useful in treating CSBP/P38 kinase mediated diseases.

There continues to be a need for easily synthesized, small-molecule compounds effective in inhibiting the catalytic activity of protein kinases, in particular FGFR and KDR kinases for treating one or more types of solid tumors. It is particularly desirable to provide small molecule inhibitors that are selective for FGFR and KDR. This is desirable because of the potential concomitant toxicity and other undesirable complications that may follow from inhibiting multiple targets. It is preferable that such small molecule inhibitors also possess advantageous bioavailability profiles. It is thus an object of this invention to provide such compounds and pharmaceutical compositions containing these compounds.

SUMMARY OF THE INVENTION

The present invention relates to novel pyrimido compounds capable of selectively inhibiting the activity of KDR and FGFR. These compounds are useful in the treatment or control of cancer, in particular the treatment or control of solid tumors. In particular this invention relates to compounds of formula

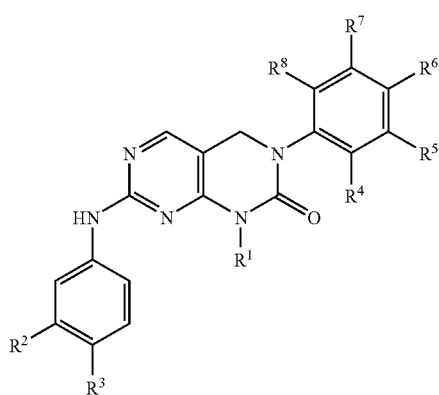

I or the pharmaceutically acceptable salts thereof, wherein $R^1$, $R^2$, $R^3$, $R^4$, $R^5$, $R^6$, $R^7$ and $R^8$ are as defined below.

The present invention also relates to pharmaceutical compositions comprising a therapeutically effective amount of one or more compounds of formula I, and/or a pharmaceutically acceptable salt thereof, and a pharmaceutically acceptable carrier or excipient.

The present invention further relates to a method for treating or controlling solid tumors, in particular treatment or control of breast, lung, colon and prostate tumors, most particularly breast or colon tumors, by administering to a human patient in need of such therapy an effective amount of a compound of formula I and/or a pharmaceutically acceptable salt thereof.

The present invention is further directed to novel intermediate compounds useful in the preparation of compounds of formula I.

DETAILED DESCRIPTION OF THE INVENTION

Definitions

As used herein, the following terms shall have the following definitions.

"Alkenyl" denotes a straight-chain or branched aliphatic hydrocarbon having 2 to 10, preferably 2 to 6, carbon atoms, and at least one carbon-carbon double bond, for example vinyl, 2-butenyl, and 3-methyl-2-butenyl.

"Alkynyl" denotes a straight-chain or branched aliphatic hydrocarbon having 2 to 10, preferably 2 to 6, carbon atoms and at least one carbon-carbon triple bond, for example ethynyl, and 2-butynyl.

"Alkyl" denotes a straight-chain or branched saturated aliphatic hydrocarbon having 1 to 10, preferably 1 to 6, and more preferably 1 to 4 carbon atoms. Alkyl groups having 1 to 6 carbon atoms are also referred to herein as "lower alkyl." Typical lower alkyl groups include methyl, ethyl, propyl, isopropyl, butyl, t-butyl, 2-butyl, pentyl and hexyl. As used herein the sample designation $C_{1-4}$ alkyl means alkyl having from 1 to 4 carbon atoms.

"Alkoxy" means an alkyl radical that is attached to the remainder of the molecule by oxygen (—OR), e.g. methoxy, ethoxy.

"Cycloalkyl" means a non-aromatic, partially or completely saturated cyclic aliphatic hydrocarbon group containing 3 to 10 atoms, preferably 3 to 6 atoms. Examples of cycloalkyl groups include cyclopropyl, cyclopentyl and cyclohexyl.

"Effective amount" or "Therapeutically Effective amount" means an amount of at least one compound for formula I, or a pharmaceutically acceptable salt thereof, that significantly inhibits proliferation of tumor cells, including human tumor cell lines.

"Halogen" means fluorine, chlorine, bromine or iodine, preferably chlorine or fluorine.

"Hetero atom" means an atom selected from N, O, and S, preferably N. If the hetero atom is N, it can be present as —NH— or —N-lower alkyl-. If the hetero atom is S, it can be present as S, SO or $SO_2$.

"Heterocycle" or "heterocyclyl" means a 3- to 10-membered saturated or partially unsaturated non-aromatic monovalent cyclic radical having from one to 4 hetero atoms selected from nitrogen, oxygen or sulfur or a combination thereof. Examples of preferred heterocycles are piperidine, piperazine, pyrrolidine, and morpholine.

"Hydroxy" is a prefix indicating the presence of a monovalent OH group.

"$IC_{50}$" refers to the concentration of a particular compound according to the invention required to inhibit 50% of a specific measured activity. $IC_{50}$ can be measured, inter alia, as is described in Examples 41 and 42, infra.

"Pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456–1457.

"Pharmaceutically acceptable," such as pharmaceutically acceptable carrier, excipient, etc., means pharmacologically acceptable and substantially non-toxic to the subject to which the particular compound is administered.

"Substituted," as in substituted alkyl, means that the substitution can occur at one or more positions and, unless otherwise indicated, that the substituents at each substitution site are independently selected from the specified options.

In one embodiment, the invention relates to compounds of formula

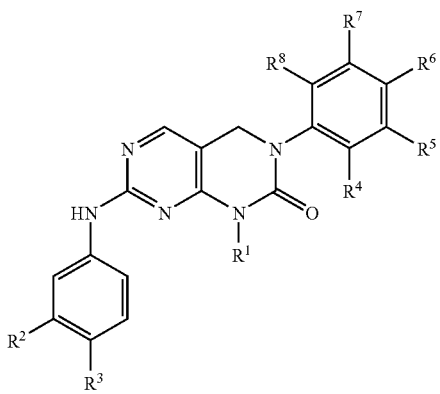

I wherein
$R^1$ is selected from the group consisting of
—H,
—$(CH_2)_n$-heterocycle,
-alkyl,
-cycloalkyl,
-alkenyl, and
-alkynyl,
where n is 0, 1, 2, or 3, and the heterocycle, alkyl, cycloalkyl, alkenyl, and alkynyl groups are each independently, optionally substituted by up to 3 groups selected from
—$OR^9$,
—$COR^{10}$,
—$CO_2R^{10}$,
—$CONR^{10}R^{11}$,
—$SO_2NR^{10}R^{11}$,
—$SO_2R^{10}$, and
—CN;
$R^2$ and $R^3$ are independently selected from the group consisting of
—H,
—$OR^9$,
-halogen,
—$COR^{10}$,
—$CO_2R^{10}$,
—$(CH_2)_n$-heterocycle,
-alkyl,
-cycloalkyl,
-alkenyl, and
-alkynyl,
where n is 0, 1, 2, or 3, and the heterocycle, alkyl, cycloalkyl, alkenyl, and alkynyl groups are each independently, optionally substituted by up to 3 groups selected from
—$OR^9$,
-halogen,
—$COR^{10}$, and
—$CO_2R^{10}$;
$R^4$, $R^5$, $R^6$, $R^7$ and $R^8$ are each independently selected from the group consisting of
—H,
-lower alkyl that optionally may be substituted by hydroxy or alkoxy,
—$OR^{12}$,
-halogen,
—$COR^{13}$, and
—$CO_2R^{13}$;
$R^9$ is selected from the group consisting of
—H,
—$COR^{10}$,
-lower alkyl that optionally may be substituted by hydroxy or alkoxy,
-cycloalkyl that optionally may be substituted by hydroxy, alkoxy, and lower alkyl, and
-heterocycle that optionally may be substituted by hydroxy, alkoxy or lower alkyl;
$R^{10}$ and $R^{11}$ are each independently selected from the group consisting of
—H,
-lower alkyl that optionally may be substituted by hydroxy or alkoxy,
-cycloalkyl that optionally may be substituted by hydroxy, alkoxy or lower alkyl, and
-heterocycle that optionally may be substituted by hydroxy, alkoxy or lower alkyl;
$R^{12}$ is selected from the group consisting of —H, lower alkyl and —$COR^{13}$; and
$R^{13}$ is selected from the group consisting of —H and lower alkyl;
or the pharmaceutically acceptable salts thereof.

Compounds disclosed herein and covered by formula I above may exhibit tautomerism or structural isomerism. It is intended that the invention encompasses any tautomeric or structural isomeric form of these compounds, or mixtures of such forms (e.g. racemic mixtures), and is not limited to any one tautomeric or structural isomeric form depicted in formula I above.

In a preferred embodiment of the compounds of formula I, $R^1$ is selected from cycloalkyl, cycloalkyl substituted by —OH, heterocycle, lower alkyl, and lower alkyl substituted by —OH.

In another preferred embodiment of the compounds of formula I, $R^2$ is —H or —$OCH_3$.

In another preferred embodiment of the compounds of formula I, $R^3$ is —H, F or —$OCH_3$.

In another preferred embodiment of the compounds of formula I, $R^2$ and $R^3$ are both —H.

In another preferred embodiment of the compounds of formula I, $R^4$, $R^5$ and $R^7$ are —H.

In another preferred embodiment of the compounds of formula I, $R^6$ is selected from $OR^{12}$, preferably —$OCH_3$, lower alkyl, preferably methyl, or halogen, preferably F.

In another preferred embodiment of the compounds of formula I, $R^8$ is —H or —F.

In another preferred embodiment of the compounds of formula I, $R^9$, $R^{10}$ and $R^{11}$ are independently selected from —H, lower alkyl, or lower alkyl substituted by hydroxy, most preferably —H.

In another preferred embodiment of the compounds of formula I, $R^{12}$ and $R^{13}$ are independently selected from —H and lower alkyl, most preferably —H.

In a particularly preferred embodiment, the invention relates to compounds of formula I wherein
$R^1$ is selected from
 —H,
 -lower alkyl substituted by —OH, $COR^{10}$, —CN, —CONH$_2$,
 —(CH$_2$)$_n$-heterocycle,
 —(CH$_2$)$_n$-heterocycle substituted by —COR$^{10}$, —CO$_2$R$^{10}$, (=O)$_2$,
 cycloalkyl,
 cycloalkyl substituted by —OH,
$R^2$ is H or —OCH$_3$;
$R^3$ is H, F or —OCH$_3$;
$R^4$, $R^5$ and $R^7$ are H;
$R^6$ is —OCH$_3$ or lower alkyl;
$R^8$ is H or F, preferably H;
$R^{10}$ is lower alkyl substituted by alkoxy; and
n is 0 or 1, preferably 0.

The following compounds are preferred embodiments according to the present invention:

1-Cyclohexyl-3-(4-methoxy-phenyl)-7-phenylamino-3,4-dihydro-1H-pyrimido[4,5-d]pyrimidin-2-one (Example 1e), 3-(4-Methoxy-phenyl)-7-phenylamino-1-piperidin-4-yl-3,4-dihydro-1H-pyrimido[4,5-d]pyrimidin-2-one (Example 2b), 1-(trans-4-Hydroxy-cyclohexyl)-3-(4-methoxy-phenyl)-7-phenylamino-3,4-dihydro-1H-pyrimido[4,5-d]pyrimidin-2-one (Example 3c), 3-(4-Methoxy-phenyl)-7-phenylamino-1-piperidin-3-yl-3,4-dihydro-1H-pyrimido[4,5-d]pyrimidin-2-one (Example 4b), 1-Cyclopentyl-3-(4-methoxy-phenyl)-7-phenylamino-3,4-dihydro-1H-pyrimido[4,5-d]pyrimidin-2-one (Example 5), 1-(1,1-Dioxo-tetrahydrothiophen-3-yl)-3-(4-methoxy-phenyl)-7-phenylamino-3,4-dihydro-1H-pyrimido[4,5-d]pyrimidin-2-one (Example 6), 3-[3-(4-Methoxy-phenyl)-2-oxo-7-phenylamino-3,4-dihydro-2H-pyrimido[4,5-d]pyrimidin-1-yl]-piperidine-1-carbaldehyde (Example 7), 3-(4-Methoxy-phenyl)-7-phenylamino-1-(tetrahydro-pyran-4-yl)-3,4-dihydro-1H-pyrimido[4,5-d]pyrimidin-2-one (Example 8), (±)-1-(trans-3-Hydroxy-cyclopentyl)-3-(4-methoxy-phenyl)-7-phenylamino-3,4-dihydro-1H-pyrimido[4,5-d]pyrimidin-2-one (Example 9d), (±)-cis-1-(3-Hydroxy-cyclopentyl)-3-(4-methoxy-phenyl)-7-phenylamino-3,4-dihydro-1H-pyrimidin-2-one (Example 10e), (R)-3-(4-Methoxy-phenyl)-7-phenylamino-1-(tetrahydro-furan-3-yl)-3,4-dihydro-1H-pyrimido[4,5-d]pyrimidin-2-one (Example 11b), (R)-3-(4-Methoxy-phenyl)-7-phenylamino-1-pyrrolidin-3-yl-3,4-dihydro-1H-pyrimido[4,5-d]pyrimidin-2-one (Example 12), (±)-7-(4-Fluoro-phenylamino)-1-(trans-3-hydroxy-cyclopentyl)-3-(4-methoxy-phenyl)-3,4-dihydro-1H-pyrimido[4,5-d]pyrimidin-2-one (Example 13c), (±)-3-(2-Fluoro-4-methoxy-phenyl)-1-(trans-3-hydroxy-cyclopentyl)-7-phenylamino-3,4-dihydro-1H-pyrimido[4,5-d]pyrimidin-2-one (Example 14d), (S)-(+)-1-(2-Hydroxy-1-methyl-ethyl)-3-(4-methoxy-phenyl)-7-phenylamino-3,4-dihydro-1H-pyrimido[4,5-d]pyrimidin-2-one (Example 15d), (S)-(+)-7-(4-Fluoro-phenylamino)-1-(2-hydroxy-1-methyl-ethyl)-3-(4-methoxy-phenyl)-3,4-dihydro-1H-pyrimido[4,5-d]pyrimidin-2-one (Example 16), 3-(2-Fluoro-4-methoxy-phenyl)-1-(trans-4-hydroxy-cyclohexyl)-7-(4-methoxy-phenylamino)-3,4-dihydro-1H-pyrimido[4,5-d]pyrimidin-2-one (Example 17d), 3-(2-Fluoro-4-methoxy-phenyl)-1-(trans-4-hydroxy-cyclohexyl)-7-(3,4-dimethoxy-phenylamino)-3,4-dihydro-1H-pyrimido[4,5-d]pyrimidin-2-one (Example 18), 3-(4-Methoxy-phenyl)-1-(trans-4-hydroxy-cyclohexyl)-7-(3,4-dimethoxy-phenylamino)-3,4-dihydro-1H-pyrimido[4,5-d]pyrimidin-2-one (Example 19c), 3-(4-Methoxy-phenyl)-1-(trans-4-hydroxy-cyclohexyl)-7-(4-methoxy-phenylamino)-3,4-dihydro-1H-pyrimido[4,5-d]pyrimidin-2-one (Example 20b), (S)-(+)-3-(2-Fluoro-4-methoxy-phenyl)-7-(4-fluoro-phenylamino)-1-(2-hydroxy-1-methyl-ethyl)-3,4-dihydro-1H-pyrimido[4,5-d]pyrimidin-2-one (Example 21b), (S)-(+)-3-(2-Fluoro-4-methoxy-phenyl)-1-(2-hydroxy-1-methyl-ethyl)-7-(4-methoxy-phenylamino)-3,4-dihydro-1H-pyrimido[4,5-d]pyrimidin-2-one (Example 22), (R)-(−)-1-(2-Hydroxy-1-methyl-ethyl)-3-(4-methoxy-phenyl)-7-phenylamino-3,4-dihydro-1H-pyrimido[4,5-d]pyrimidin-2-one (Example 23d), 3-(4-Methoxy-phenyl)-1-methyl-7-phenylamino-3,4-dihydro-1H-pyrimido[4,5-d]pyrimidine-2-one (Example 24b), 1-(2-methoxy-ethoxymethyl)-3-(4-methoxy-phenyl)-7-phenylamino-3,4-dihydro-1H-pyrimido[4,5-d]pyrimidin-2-one (Example 25), 3-[3-(4-Methoxy-phenyl)-2-oxo-7-phenylamino-3,4-dihydro-1H-pyrimido[4,5-d]pyrimidin-1-yl]-propionitrile (Example 26), (+)-(1R,3R)-1-(3-Hydroxy-cyclopentyl)-3-(4-methoxy-phenyl)-7-phenylamino-3,4-dihydro-1H-pyrimido[4,5-d]pyrimidin-2-one (Example 27f), (R)-1-(2-Hydroxy-propyl)-3-(4-methoxy-phenyl)-7-phenylamino-3,4-dihydro-1H-pyrimido[4,5-d]pyrimidin-2-one (Example 28d), (−)-(1S,3S)-1-(3-Hydroxy-cyclopentyl)-3-(4-methoxy-phenyl)-7-phenylamino-3,4-dihydro-1H-pyrimido[4,5-d]pyrimidin-2-one (Example 29h), 3-[3-(4-Methoxy-phenyl)-2-oxo-7-phenylamino-3,4-dihydro-1H-pyrimido[4,5-d]pyrimidin-1-yl]-propionamide (Example 30), (S)-(+)-1-(2-Hydroxy-propyl)-3-(4-methoxy-phenyl)-7-phenylamino-3,4-dihydro-1H-pyrimido[4,5-d]pyrimidin-2-one (Example 31d), 1-(cis-3,5-Dihydroxy-cyclohexyl)-3-(2-fluoro-4-methoxy-phenyl)-7-(4-methoxyphenylamino)-3,4-dihydro-1H-pyrimido[4,5-d]pyrimidin-2-one (Example 32f), 1-(cis-3,5-Dihydroxy-cyclohexyl)-3-(4-methoxy-phenyl)-7-(4-methoxyphenylamino)-3,4-dihydro-1H-pyrimido[4,5-d]pyrimidin-2-one (Example 33c), 1-(cis-3,5-Dihydroxy-cyclohexyl)-3-(4-methoxy-phenyl)-7-(4-fluoro-3-methoxyphenylamino)-3,4-dihydro-1H-pyrimido[4,5-d]pyrimidin-2-one (Example 34f), 1-(cis-3,5-Dihydroxy-cyclohexyl)-3-(4-methoxy-phenyl)-7-phenylamino-3,4-dihydro-1H-pyrimido[4,5-d]pyrimidin-2-one (Example 35b), 1-(cis-3,5-Dihydroxy-cyclohexyl)-3-(2-fluoro-4-methoxy-phenyl)-7-phenylamino-3,4-dihydro-1H-pyrimido[4,5-d]pyrimidin-2-one (Example 36b), 1-(cis-3,5-Dihydroxy-cyclohexyl)-3-(2-fluoro-4-methoxy-phenyl)-7-(4-fluoro-3-methoxyphenylamino)-3,4-dihydro-1H-pyrimido[4,5-d]pyrimidin-2-one (Example 37b), (R)-3-(4-Ethyl-phenyl)-7-(4-fluoro-phenylamino)-1-(2-hydroxy-1-methyl-ethyl)-3,4-dihydro-1H-pyrimido[4,5-d]pyrimidin-2-one (Example 38g), (±)-3-(4-Ethyl-phenyl)-7-(4-fluoro-phenylamino)-1-(trans-3-hydroxy-cyclopentyl)-3,4-dihydro-1H-pyrimido[4,5-d]pyrimidin-2-one (Example 39d), and 1-Cyclopropylmethyl-3-(4-methoxy-phenyl)-7-phenylamino-3,4-dihydro-1H-pyrimido[4,5-d]pyrimidine-2-one (Example 40).

The compounds of the invention are selective for FGF and KDR kinases. These compounds are useful in the treatment or control of cancer, in particular the treatment or control of solid tumors, specifically breast, lung, colon and prostate tumors. These compounds are highly permeable to cell membranes and thus possess advantageous bioavailability profiles such as improved oral bioavailability.

General Synthesis of Compounds According to the Invention

The compounds of the present invention can be prepared by any conventional means. Suitable processes for synthesizing these compounds are provided in the examples. Generally, compounds of formula I can be prepared according to the below described synthetic routes.

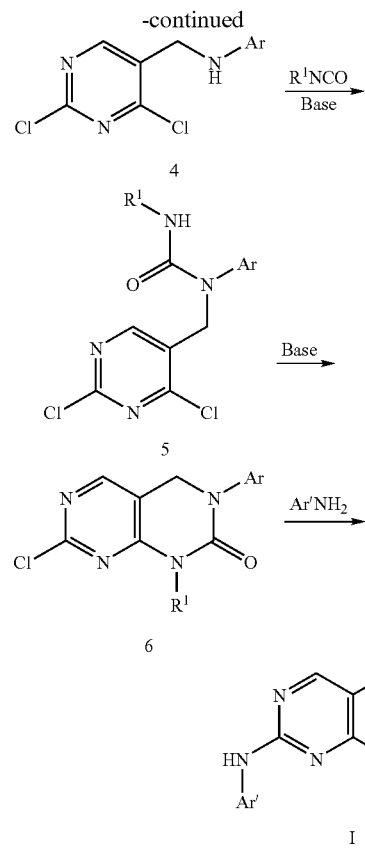

Alternatively, compounds of Formula I may be obtained as follows:

Alternately, compounds of Formula I can be synthesized as follows.

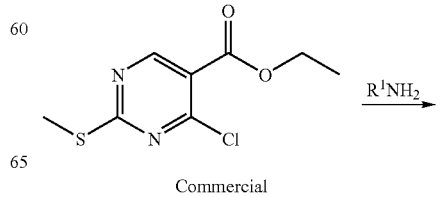

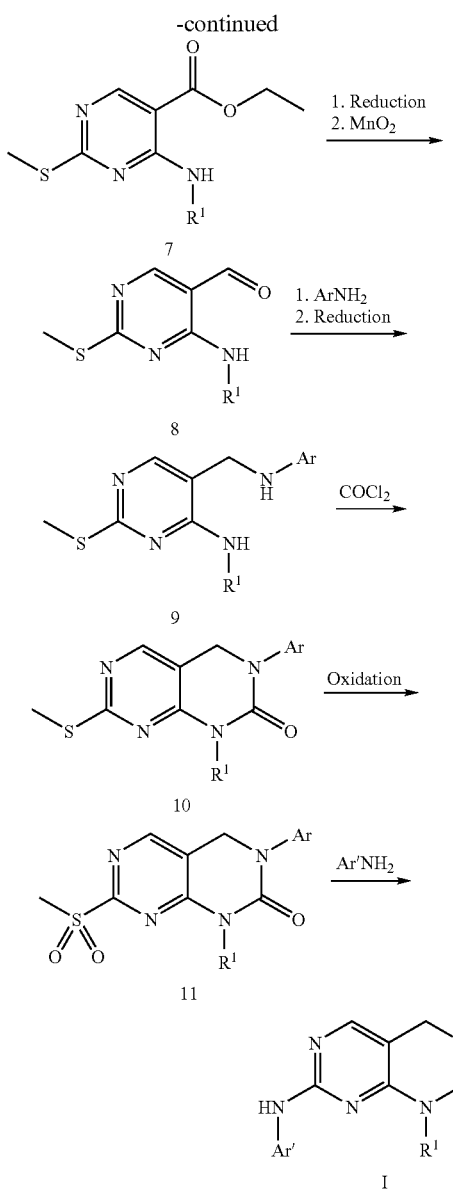

Compounds of Formula I may also be obtained from compound 4 as follows:

Alternatively, compound 6 may be obtained from compound 4 as follows:

Compositions/Formulations

In an alternative embodiment, the present invention relates to pharmaceutical compositions comprising at least one compound of formula I, and/or a pharmaceutically acceptable salt thereof, and a pharmaceutically acceptable carrier or excipient.

These pharmaceutical compositions can be administered orally, for example in the form of tablets, coated tablets, dragees, hard or soft gelatin capsules, solutions, emulsions or suspensions. They can also be administered rectally, for example, in the form of suppositories, or parenterally, for example, in the form of injection solutions.

The pharmaceutical compositions of the present invention comprising compounds of formula I, and/or the pharmaceutically acceptable salts thereof, may be manufactured in a manner that is known in the art, e.g. by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, corn starch or derivatives thereof, talc, steric acid or its salts can be used as such carriers for tablets, coated tablets, dragees and hard gelatin capsules. Suitable carriers for soft gelatin capsules include vegetable oils, waxes and fats. Depending on the nature of the active substance, no carriers are generally required in the case of soft gelatin capsules. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I, in particular other oncological agents.

Dosages

As mentioned above, the compounds of the present invention, including the compounds of formula I, and/or the pharmaceutically acceptable salts thereof, are useful in the treatment or control of cell proliferative disorders, in particular oncological disorders. These compounds and formulations containing said compounds are particularly useful in the treatment or control of solid tumors, such as, for example, breast, colon, lung and prostate tumors. Thus, the present invention is further directed to a method for treating such solid tumors by administering to a patient in need of such therapy an effective amount of a compound of formula I and/or a pharmaceutically acceptable salt thereof.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70–75 Kg, a daily dosage of about 10 mg to about 10,000 mg, preferably from about 200 mg to about 1,000 mg, most preferably 300 mg to 600 mg, should be appropriate, although the upper limit may be exceeded when indicated. The daily dosage can be administered as a single dose or in divided doses, or for parenteral administration, it may be given as continuous infusion.

The present invention is also directed to the following novel intermediates useful in the synthesis of compounds of formula I:

4-[3-(4-Methoxy-phenyl)-2-oxo-7-phenylamino-3,4-dihydro-2H-pyrimido[4,5-d]pyrimidin-1-yl]-piperidine-1-carboxylic acid tert-butyl ester (Example 2a), 1-[trans-4-(tert-Butyl-dimethyl-silanyloxy)-cyclohexyl]-3-(4-methoxy-phenyl)-7-phenylamino-3,4-dihydro-1H-pyrimido[4,5-d]pyrimidin-2-one (Example 3b), 3-[3-(4-Methoxy-phenyl)-2-oxo-7-phenylamino-3,4-dihydro-2H-pyrimido[4,5-d]pyrimidin-1-yl]-piperidine-1-carboxylic acid tert-butyl ester (Example 4a), (±)-3-cis-(tert-Butyl-dimethyl-silanyloxy)-cyclopentyl]-3-(4-methoxy-phenyl)-7-phenylamino-3,4-dihydro-1H-pyrimido[4,5-d]pyrimidin-2-one (Example 10d), (R)-2-Methylsulfanyl-4-(tetrahydro-furan-3-ylamino)-pyrimidine-5-carboxylic acid ethyl ester (Example 11a), (±)-4-[trans-3-(tert-Butyl-dimethyl-silanyloxy)-cyclopentylamino]-2-methylsulfanyl-pyrimidine-5-carbaldehyde (Example 13a), (±)-1-[trans-3-(tert-Butyl-dimethyl-silanyloxy)-cyclopentyl]-3-(4-methoxy-phenyl)-7-methylsulfanyl-3,4-dihydro-1H-pyrimido[4,5-d]pyrimidin-2-one (Example 13b), (±)-[3-trans-(tert-Butyl-dimethyl-silanyloxy)-cyclopentyl]-{5-[(2-fluoro-4-methoxyphenylamino)-methyl]-2-methylsulfanyl-pyrimidin-4-yl}-amine (Example 14b), (±)-1-[trans-3-(tert-Butyl-dimethyl-silanyloxy)-cyclopentyl]-3-(4-methoxy-phenyl)-7-methylsulfanyl-3,4-dihydro-1H-pyrimido[4,5-d]pyrimidin-2-one (Example 14c), (S)-1-[2-(tert-Butyl-diphenyl-silanyloxy)-1-methyl-ethyl]-7-chloro-3-(4-methoxy-phenyl)-3,4-dihydro-1H-pyrimido[4,5-d]pyrimidin-2-one (Example 15c), 1-[trans-4-(tert-Butyl-dimethyl-silanyloxy)-cyclohexyl]-7-chloro-3-(2-fluoro-4-methoxy-phenyl)-3,4-dihydro-1H-pyrimido[4,5-d]pyrimidin-2-one (Example 17c), 1-[trans-4-(tert-Butyl-dimethyl-silanyloxy)-cyclohexyl]-7-chloro-3-(4-methoxy-phenyl)-3,4-dihydro-1H-pyrimido[4,5-d]pyrimidin-2-one (Example 19a), 1-[trans-4-(tert-Butyl-dimethyl-silanyloxy)-cyclohexyl]-3-(4-methoxy-phenyl)-7-(3,4-dimethoxy-phenylamino)-3,4-dihydro-1H-pyrimido[4,5-d]pyrimidin-2-one (Example 19b), 1-[trans-4-(tert-Butyl-dimethyl-silanyloxy)-cyclohexyl]-3-(4-methoxy-phenyl)-7-(4-methoxy-phenylamino)-3,4-dihydro-1H-pyrimido[4,5-d]pyrimidin-2-one (Example 20a), (S)-1-[2-(tert-Butyl-diphenyl-silanyloxy)-1-methyl-ethyl]-7-chloro-3-(2-fluoro-4-methoxy-phenyl)-3,4-dihydro-1H-pyrimido[4,5-d]pyrimidin-2-one (Example 21a), (R)-1-[2-(tert-Butyl-diphenyl-silanyloxy)-1-methyl-ethyl]-7-chloro-3-(4-methoxy-phenyl)-3,4-dihydro-1H-pyrimido[4,5-d]pyrimidin-2-one (Example 23c), 3-(4-Methoxy-phenyl)-7-phenylamino-3,4-dihydro-1H-pyrimido[4,5-d]pyrimidine-2-one (Example 24a), (+)-(1R,3R)-4-[3-(tert-Butyl-dimethyl-silanyloxy)-cyclopentylamino]-2-methylsulfanyl-pyrimidine-5-carboxylic acid ethyl ester (Example 27d), (−)-(1R,3R)-1-[3-(tert-Butyl-dimethyl-silanyloxy)-cyclopentyl]-3-(4-methoxy-phenyl)-7-phenylamino-3,4-dihydro-1H-pyrimido[4,5-d]pyrimidin-2-one (Example 27e), (R)-1-[2-(tert-Butyl-diphenyl-silanyloxy)-propyl]-7-chloro-3-(4-methoxy-phenyl)-3,4-dihydro-1H-pyrimido[4,5-d]pyrimidin-2-one (Example 28c), (−)-(1S,3S)-4-[3-(tert-Butyl-dimethyl-silanyloxy)-cyclopentylamino]-2-methylsulfanyl-pyrimidine-5-carboxylic acid ethyl ester (Example 29d), (−)-(1S,3S)-4-[3-(tert-Butyl-dimethyl-silanyloxy)-cyclopentylamino]-2-methylsulfanyl-pyrimidine-5-carbaldehyde (Example 29e), (−)-(1S,3S)-1-[3-(tert-Butyl-dimethyl-silanyloxy)-cyclopentyl]-3-(4-methoxy-phenyl)-7-methylsulfanyl-3,4-dihydro-1H-pyrimido[4,5-d]pyrimidin-2-one (Example 29f),
(−)-(1S,3S)-1-[3-(tert-Butyl-dimethyl-silanyloxy)-cyclopentyl]-3-(4-methoxy-phenyl)-7-phenylamino-3,4-dihydro-1H-pyrimido[4,5-d]pyrimidin-2-one (Example 29g),
(S)-1-[2-(tert-Butyl-diphenyl-silanyloxy)-propyl]-7-chloro-3-(4-methoxy-phenyl)-3,4-dihydro-1H-pyrimido[4,5-d]pyrimidin-2-one (Example 31c),
1-[cis-3,5-Bis-(tert-butyl-diphenyl-silanyloxy)-cyclohexyl]-7-chloro-3-(2-fluoro-4-methoxy-phenyl)-3,4-dihydro-1H-pyrimido[4,5-d]pyrimidin-2-one (Example 32d),
1-[cis-3,5-Bis-(tert-butyl-diphenyl-silanyloxy)-cyclohexyl]-3-(2-fluoro-4-methoxy-phenyl)-7-(4-methoxy-phenylamino)-3,4-dihydro-1H-pyrimido[4,5-d]pyrimidin-2-one (Example 32e),
1-[cis-3,5-Bis-(tert-butyl-diphenyl-silanyloxy)-cyclohexyl]-7-chloro-3-(4-methoxy-phenyl)-3,4-dihydro-1H-pyrimido[4,5-d]pyrimidin-2-one (Example 33a),
1-[cis-3,5-Bis-(tert-butyl-diphenyl-silanyloxy)-cyclohexyl]-3-(4-methoxy-phenyl)-7-(4-methoxy-phenylamino)-3,4-dihydro-1H-pyrimido[4,5-d]pyrimidin-2-one (Example 33b),
1-[cis-3,5-Bis-(tert-butyl-diphenyl-silanyloxy)-cyclohexyl]-3-(4-methoxy-phenyl)-7-(4-fluoro-3-methoxy-phenylamino)-3,4-dihydro-1H-pyrimido[4,5-d]pyrimidin-2-one (Example 34e),
1-[cis-3,5-Bis-(tert-butyl-diphenyl-silanyloxy)-cyclohexyl]-3-(4-methoxy-phenyl)-7-phenylamino-3,4-dihydro-1H-pyrimido[4,5-d]pyrimidin-2-one (Example 35a),
1-[cis-3,5-Bis-(tert-butyl-diphenyl-silanyloxy)-cyclohexyl]-3-(2-fluoro-4-methoxy-phenyl)-7-phenylamino-3,4-dihydro-1H-pyrimido[4,5-d]pyrimidin-2-one (Example 36a),
1-[cis-3,5-Bis-(tert-butyl-diphenyl-silanyloxy)-cyclohexyl]-3-(2-fluoro-4-methoxy-phenyl)-7-(4-fluoro-3-methoxy-phenylamino)-3,4-dihydro-1H-pyrimido[4,5-d]pyrimidin-2-one (Example 37a),
(2,4-Dichloro-pyrimidin-5-ylmethyl)-(4-ethyl-phenyl)-amine (Example 38c),
(R)-3-[2-(tert-Butyl-dimethyl-silanyloxy)-1-methyl-ethyl]-1-(2,4-dichloro-pyrimidin-5-ylmethyl)-1-(4-ethyl-phenyl)-urea (Example 38d),
(R)-1-[2-(tert-Butyl-dimethyl-silanyloxy)-1-methyl-ethyl]-7-chloro-3-(4-ethyl-phenyl)-3,4-dihydro-1H-pyrimido[4,5-d]pyrimidin-2-one (Example 38e),
(R)-1-[2-(tert-Butyl-dimethyl-silanyloxy)-1-methyl-ethyl]-3-(4-ethyl-phenyl)-7-(4-fluoro-phenylamino)-3,4-dihydro-1H-pyrimido[4,5-d]pyrimidin-2-one (Example 38f),
(±)-[trans-3-(tert-Butyl-dimethyl-silanyloxy)-cyclopentyl]-{2-chloro-5-[(4-ethyl-phenylamino)-methyl]-pyrimidin-4-yl}-amine (Example 39a),
(±)-1-[trans-3-(tert-Butyl-dimethyl-silanyloxy)-cyclopentyl]-7-chloro-3-(4-ethyl-phenyl)-3,4-dihydro-1H-pyrimido[4,5-d]pyrimidin-2-one (Example 39b), and
(±)-1-[trans-3-(tert-Butyl-dimethyl-silanyloxy)-cyclopentyl]-3-(4-ethyl-phenyl)-7-(4-fluoro-phenylamino)-3,4-dihydro-1H-pyrimido[4,5-d]pyrimidin-2-one (Example 39c).

EXAMPLES

The following examples illustrate preferred methods for synthesizing the compounds and formulations of the present invention.

Example 1

Example 1a 5-(Hydroxymethyl)-1,3-dihydropyrimidine-2,4-dione

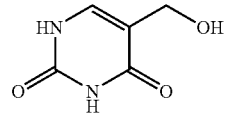

A 2-L, three-necked flask equipped with a mechanical stirrer, thermometer, condenser, and nitrogen-inlet bubbler was charged with uracil (185.0 g, 1650 mmol) (Aldrich), paraformaldehyde (61.50 g, 2050 mmol as formaldehyde) (Aldrich), and a solution of potassium hydroxide (86.9%, 59.95 g, 928.5 mmol) (Aldrich) in water (1.445 L). The mixture was stirred at 50–52° C. for 68 hours. TLC analysis indicated complete reaction. After concentration at 60° C./14 mm Hg to a volume of ca. 500 mL, the residue was diluted with acetone (500 mL). The resulting precipitate was collected by filtration, washed with acetone, and dried by suction, then at 50° C./25 mm Hg to give crude 5-(hydroxymethyl)-1,3-dihydropyrimidine-2,4-dione (250 g) as a white solid. The combined mother liquor and washes were concentrated to a volume of ca. 100 mL and a solution of hydroxylamine hydrochloride (27.52 g, 396.0 mmol, Aldrich) in water (100 mL) was added. The resulting precipitate was collected by filtration, washed with acetone, and dried by suction to give second crop of crude 5-(hydroxymethyl)-1,3-dihydropyrimidine-2,4-dione (34 g) as a white solid. The two lots were combined (244 g, 4% overweight) and used directly in the next step.

Example 1b 2,4-Dichloro-5-(chloromethyl)pyrimidine

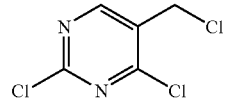

A 1-L, three-necked flask equipped with a mechanical stirrer, addition funnel, thermometer and nitrogen-inlet bubbler was charged with crude 5-(hydroxymethyl)-1,3-dihydropyrimidine-2,4-dione (50.25 g, ca. 340 mmol) (from Example 1a supra), phosphorous oxychloride (164.8 mL, 1768 mmol) (Aldrich), and toluene (100 mL). To this mixture was added N,N-diisopropylethylamine (184.7 mL, 1060 mmol) (Aldrich) over 10 min, while maintaining the temperature of the mixture below 70° C. using a water bath. After completion of the addition, the cooling bath was removed and the mixture was heated to reflux (113–116° C.) for 1 hour. Some of the toluene (ca. 35 mL) was removed by distillation to increase the temperature of the reaction mixture to 120° C. and the mixture was stirred at 120–123° C. for 5 hours. TLC analysis indicated reaction was complete. After the mixture was allowed to cool to room temperature overnight, the mixture was cautiously added, over 67 minutes, to a stirred bi-phasic mixture of water (200 mL) and isopropyl acetate (150 mL), while maintaining the temperature between 17° C. to 21° C. using an ice-water bath. After stirring at 18–21° C. for 80 minutes with occasional ice-water cooling, the mixture was extracted with toluene (4×150 mL). The combined organic layers were dried (sodium sulfate), filtered, then concentrated to dryness under reduced pressure to give crude 2,4-dichloro-5-(chloromethyl)pyrimidine as a white solid, containing polar impurities. (Yield 56.1 g, 83.6% yield from uracil).

Crude 2,4-dichloro-5-(chloromethyl)pyrimidine (70.39 g) was dissolved in dichloromethane (80 mL) and the resulting solution was filtered through a pad of TLC grade silica gel (100 g). The silica gel was then washed with dichloromethane:hexanes (1 L, 7:3), and the combined filtrate and washes were concentrated to dryness under reduced pressure to give 2,4-dichloro-5-(chloromethyl)pyrimidine as a white solid. (Yield 58.77 g, 83.5% recovery, 69.8% overall yield from uracil).

Example 1c 2,4-Dichloro-5-(iodomethyl)pyrimidine

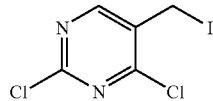

A 500-mL, round-bottom flask equipped with a magnetic stirrer, condenser, and nitrogen-inlet bubbler was charged with sodium iodide (38.5 g, 256.9 mmol) (Aldrich) and acetone (300 mL). After a clear solution was obtained, 2,4-dichloro-5-(chloromethyl)pyrimidine (50.0 g, 253.2 mmol) (from Example 1b supra) was added in one portion. After stirring at room temperature for 20 minutes, the mixture was heated to reflux for 15 minutes. NMR analysis indicated 98% conversion. After cooling to room temperature, the resulting precipitate (sodium chloride) was removed by filtration through a medium-sintered glass funnel and washed with acetone. The combined filtrate and washes were concentrated to a weight of ca. 75 g. The resulting concentrated solution of 2,4-dichloro-5-(iodomethyl)pyrimidine in acetone was diluted with toluene (20 mL). After concentration to a weight of ca. 85 g in order to remove the residual acetone, this concentrated solution of 2,4-dichloro-5-(iodomethyl)pyrimidine in toluene was used directly in the next step.

Example 1d

[(2,4-Dichloropyrimidin-5-yl)methyl](4-methoxyphenyl)amine

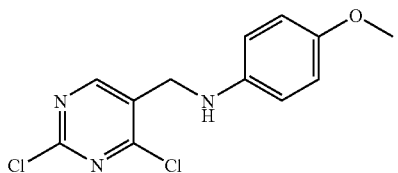

A 500-mL, three-necked flask equipped with a magnetic stirrer, thermometer, and nitrogen-inlet bubbler was charged with a solution of 2,4-dichloro-5-(iodomethyl)pyrimidine (85 g, ca. 253.2 mmol) (from Example 1c supra) in toluene (13.7 mL) from the previous step and toluene (96.3 mL, thus, a total of ca. 110 mL of toluene). After cooling with an ice-water bath, p-anisidine (31.18 g, 253.2 mmol) (Aldrich) was added. After stirring for 30 minutes, a solution of sodium hydroxide (13.54 g, 331.7 mmol) in water (50 mL) was added dropwise over 8 minutes, while maintaining the temperature of the reaction mixture at 10–15° C. hexanes (55 mL) was added and the mixture was stirred at 10–15° C. for 45 minutes, then at room temperature for 22 hours to give a slurry. TLC analysis of the supernatant indicated complete reaction. The slurry was diluted with water (100 mL) and the solid was collected by filtration, washed with cold water and cold (−50° C.) methanol (100 mL), and dried by suction to give [(2,4-dichloropyrimidin-5-yl)methyl](4-methoxyphenyl)amine as an off-white solid, 97% pure by HPLC analysis. (Yield 59.87 g, 83.2%).

Example 1e

1-Cyclohexyl-3-(4-methoxy-phenyl)-7-phenylamino-3,4-dihydro-1H-pyrimido[4,5-d]pyrimidin-2-one

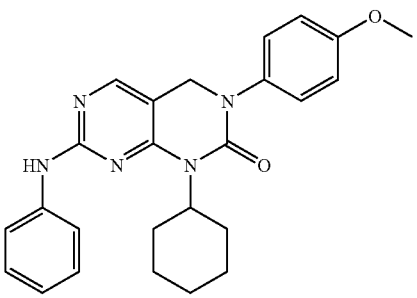

A solution of [(2,4-dichloropyrimidin-5-yl)methyl](4-methoxyphenyl)amine (200 mg, 0.70 mmol) (from Example 1d supra) in anhydrous tetrahydrofuran (24 mL) was treated with n-butyllithium (1.6 M solution in hexanes, 0.53 mL, 0.84 mmol) (Aldrich) at −78° C. This was followed by addition of cyclohexyl isocyanate (90 μL, 88 mg, 0.70 mmol) (Aldrich). The resulting mixture was stirred and slowly warmed up to room temperature within a period of 2 hours. The reaction mixture was then partitioned between ethyl acetate and brine. The organic layer was collected, dried over sodium sulfate, filtered and concentrated to a residue that was purified by chromatography with a silica gel column using a 0–60% ethyl acetate in hexanes gradient. The intermediate that was obtained from this purification was dissolved in aniline (2 mL) (Aldrich), a catalytic amount of 4-(dimethylamino)pyridine (Aldrich) was added and the mixture was then heated at 100° C. After stirring overnight the mixture was cooled, and purified by silica gel column chromatography with a 0–60% ethyl acetate in hexanes gradient. The solid obtained from this purification was dissolved in tetrahydrofuran and then precipitated with excess of pentane to give 1-cyclohexyl-3-(4-methoxy-phenyl)-7-phenylamino-3,4-dihydro-1H-pyrimido[4,5-d]pyrimidin-2-one as a beige solid. (Yield 78 mg, 26%).

HRMS m/z calcd for $C_{25}H_{27}N_5O_2$ [M$^+$]: 429.2165. Found: 429.2165.

Example 2a

4-[3-(4-Methoxy-phenyl)-2-oxo-7-phenylamino-3,4-dihydro-2H-pyrimido[4,5-d]pyrimidin-1-yl]-piperidine-1-carboxylic acid tert-butyl ester

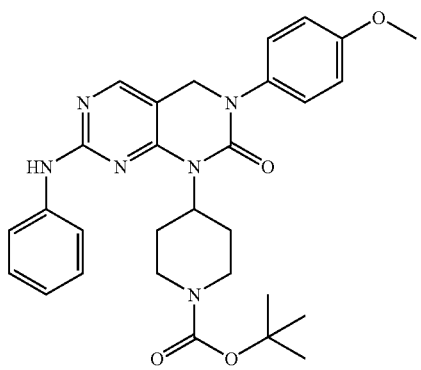

A solution of 1-N-Boc-4-amino piperidine (300 mg, 1.49 mmol) (Astatech) and triethylamine (840 µL, 606 mg, 5.99 mmol) (Aldrich) in anhydrous dichloromethane (10 mL) was treated at 0° C. with a 20% solution of phosgene in toluene (1.47 mL, 2.99 mmol) (Fluka). After stirring for 30 minutes the mixture was partitioned between 0.5 M aqueous hydrochloric acid and dichloromethane. The organic layer was then collected, washed with brine, dried over sodium sulfate and concentrated. The residue was dissolved in diethyl ether (approx. 6 mL) and the resulting solution was filtered and concentrated. The residue was then dissolved in a small volume of anhydrous tetrahydrofuran (approx. 3 mL) and transferred via cannula to a −78° C. solution of [(2,4-dichloropyrimidin-5-yl)methyl](4-methoxyphenyl)amine (300 mg, 1.06 mmol) (from Example 1d supra) and n-butyllithium (2.5 M solution in hexanes, 0.51 mL, 1.27 mmol) in anhydrous tetrahydrofuran (20 mL). The reaction mixture was allowed to slowly warm to room temperature and stirred for 4 hours before it was partitioned between ethyl acetate and brine. The organic layer was then collected, dried over sodium sulfate, filtered, concentrated and the residue was purified by chromatography on a silica gel column with 0–60% ethyl acetate in hexanes. The product from this purification was then dissolved in aniline (2 mL) (Aldrich) and the resulting solution was heated at 80° C. for a period of 12 hours. The reaction mixture was then cooled, and purified by silica gel column chromatography using a 0–70% ethyl acetate in hexanes gradient to afford the product. After a precipitation out of THF with excess of pentane, 4-[3-(4-methoxy-phenyl)-2-oxo-7-phenylamino-3,4-dihydro-2H-pyrimido[4,5-d]pyrimidin-1-yl]-piperidine-1-carboxylic acid tert-butyl ester was isolated as an off white solid. (Yield 74 mg, 13%).

HRMS m/z Calculated for $C_{29}H_{34}N_6O_4$ [M+]: 530.2641. Found: 530.2640.

Example 2b 3-(4-Methoxy-phenyl)-7-phenylamino-1-piperidin-4-yl-3,4-dihydro-1H-pyrimido[4,5-d]pyrimidin-2-one

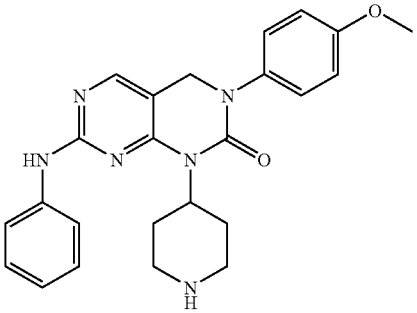

4-[3-(4-Methoxy-phenyl)-2-oxo-7-phenylamino-3,4-dihydro-2H-pyrimido[4,5-d]pyrimidin-1-yl]-piperidine-1-carboxylic acid tert-butyl ester (70 mg, 0.13 mmol) (from Example 2a supra) was dissolved at 0° C. in a 50% solution of trifluoroacetic acid in dichloromethane (6 mL) that contained 100 µL of water. After stirring for 1.5 hours the mixture was partitioned between ethyl acetate and 1 N aqueous sodium hydroxide and the pH of the aqueous layer was adjusted to 12 by the addition of solid sodium hydroxide. The organic layer was then washed with water, dried over sodium sulfate, filtered and concentrated. The crude material was purified by precipitation out of tetrahydrofuran with excess of pentane to give 3-(4-methoxy-phenyl)-7-phenylamino-1-piperidin-4-yl-3,4-dihydro-1H-pyrimido[4,5-d]pyrimidin-2-one as an off white solid. (Yield 42 mg, 75%).

HRMS m/z Calculated for $C_{24}H_{27}N_6O_2$ [(M+H)+]: 431.2190. Found: 431.2190.

Example 3a trans-4-(tert-Butyl-dimethyl-silanyloxy)-cyclohexylamine

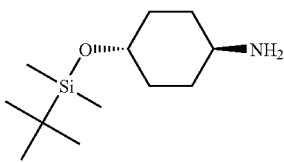

To a solution of trans-4-aminocyclohexanol (5.0 g, 43.4 mmol) (TCI US) in dichloromethane (100 mL) was added imidazole (14.78 g, 0.22 mol) (Aldrich) and tert-butyldimethylsilyl chloride (19.63 g, 0.13 mol) (Avocardo Research Chemicals). The reaction mixture was stirred at room temperature for 1 day and then was concentrated under reduced pressure. The residue was partitioned between ethyl acetate (100 mL) and water (100 mL). The organic layer was washed with 1N sodium hydroxide solution, water and brine, dried over magnesium sulfate, filtered and concentrated to give trans-4-(tert-butyl-dimethyl-silanyloxy)-cyclohexylamine. (Yield 7.62 g, 76.5%).

Example 3b

1-[trans-4-(tert-Butyl-dimethyl-silanyloxy)-cyclohexyl]-3-(4-methyoxy-phenyl)-7-phenylamino-3,4-dihydro-1H-pyrimido[4,5-d]pyrimidin-2-one

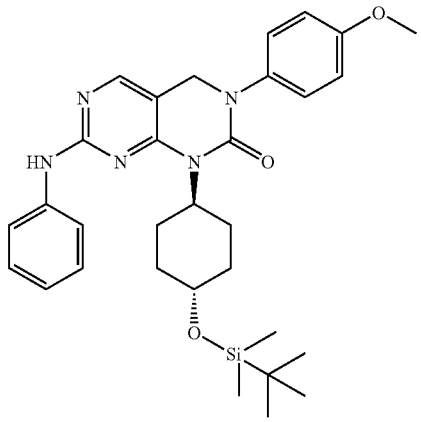

A solution of trans-4-(tert-butyl-dimethyl-silanyloxy)-cyclohexylamine (350 mg, 1.53 mmol) (from Example 3a supra) in dichloromethane (10 mL) was treated with triethylamine (850 µL, 630 mg, 6.10 mmol) (Aldrich) and then at 0° C. with a solution of phosgene in toluene (20%, 1.49 mL, 3.05 mmol) (Fluka). After stirring for 30 minutes the reaction mixture was partitioned between dichloromethane and 0.5 M aqueous hydrochloric acid. The organic layer was separated, washed with brine, dried over sodium sulfate, filtered and concentrated under reduced pressure. The residue was dissolved in diethyl ether and the resulting solution was filtered and concentrated. The residue obtained was then dissolved in a small volume of anhydrous tetrahydrofuran (approx. 3 mL) and transferred via cannula to a −78° C. solution of (2,4-dichloro-pyrimidin-5-yl-methyl)-(4-methoxy-phenyl)-amine (340 mg, 1.19 mmol) (from Example 1d supra) and n-butyllithium (2.5 M solution in hexanes, 0.61 mL, 1.52 mmol) (Aldrich) in anhydrous tetrahydrofuran (25 mL). The reaction mixture was allowed to slowly warm to room temperature and stirred for 2 hours and 15 minutes. The mixture was then partitioned between ethyl acetate and brine. The organic layer was separated, dried over sodium sulfate, filtered, concentrated and the residue was purified by chromatography on a silica gel column with 0–60% ethyl acetate in hexanes gradient. The intermediate from this purification was dissolved in aniline (3 mL) (Aldrich) and the resulting solution was heated at 80° C. for 12 hours. The mixture was then cooled and purified by silica gel column chromatography using a 0–50% ethyl acetate in hexanes gradient to afford the product. After a precipitation out of diethyl ether with excess of pentane 1-[trans-4-(tert-butyl-dimethyl-silanyloxy)-cyclohexyl]-3-(4-methoxy-phenyl)-7-phenylamino-3,4-dihydro-1H-pyrimido[4,5-d]pyrimidin-2-one was isolated as an off-white solid. (Yield 139 mg, 21%).

HRMS m/z Calculated for $C_{31}H_{42}N_5O_3Si$ [(M+H)$^+$]: 560.3052. Found: 560.3056.

Example 3c 1-(trans-4-Hydroxy-cyclohexyl)-3-(4-methoxy-phenyl)-7-phenylamino-3,4-dihydro-1H-pyrimido[4,5-d]pyrimidin-2-one

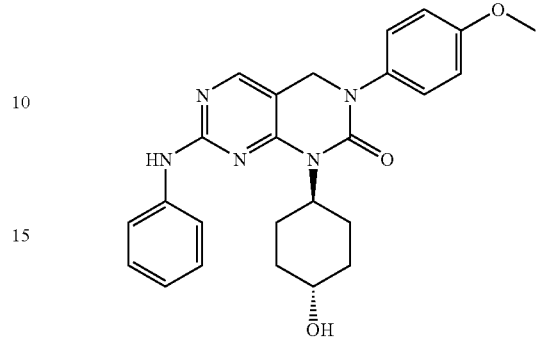

1-[trans-4-(tert-Butyl-dimethyl-silanyloxy)-cyclohexyl]-3-(4-methoxy-phenyl)-7-phenylamino-3,4-dihydro-1H-pyrimido[4,5-d]pyrimidin-2-one (from Example 3b supra) (139 mg, 0.25 mmol) was dissolved at 0° C. in a 50% solution of trifluoroacetic acid in dichloromethane (5 mL) that contained water (330 µL). After stirring for 1.5 hours the reaction mixture was partitioned between ethyl acetate and 1 N aqueous sodium hydroxide and the pH of the aqueous layer was adjusted to 12 by adding solid sodium hydroxide. The organic layer was then washed with water, dried over sodium sulfate, filtered and concentrated to the crude product. Purification by silica gel column chromatography with 0–100% ethyl acetate in hexanes gradient followed by a precipitation out of tetrahydrofuran with excess of pentane afforded 1-(trans-4-hydroxy-cyclohexyl)-3-(4-methoxy-phenyl)-7-phenylamino-3,4-dihydro-1H-pyrimido[4,5-d]pyrimidin-2-one as an off-white solid. (Yield 72 mg, 65%).

HRMS m/z calcd for $C_{25}H_{27}N_5O_3$ [M$^+$]: 445.2114. Found: 445.2122.

Example 4a

3-[3-(4-Methoxyl-phenyl)-2-oxo-7-phenylamino-3,4-dihydro-2H-pyrimido[4,5-d]pyrimidin-1-yl]-piperidine-1-carboxylic acid tert-butyl ester

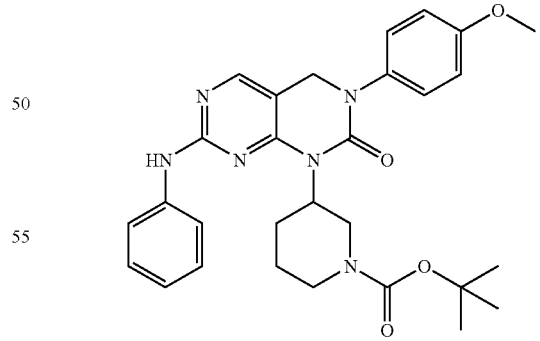

A mixture of 1-N-BOC-3-aminopiperidine (350 mg, 1.75 mmol) (Astatech) and triethylamine (710 mg, 970 µL, 7.00 mmol) (Aldrich) in dichloromethane (10 mL) at 0° C. was treated with a 20% phosgene solution in toluene (1.7 mL, 3.47 mmol) (Fluka). After stirring for 30 minutes the reaction mixture was filtered and the filtrate was concentrated to a small volume. Benzene (5 mL) was added and the resulting mixture was filtered again and concentrated. The residue was dissolved in a small volume of anhydrous tetrahydrofuran (approx. 3 mL) and transferred via cannula to a −78° C. solution of (2,4-dichloro-pyrimidin-5-ylmethyl)-(4-methoxyphenyl)-amine (340 mg, 1.19 mmol) (from Example 1d supra) and n-butyllithium (2.5 M solution of in hexanes, 0.70 mL, 1.75 mmol) (Aldrich) in anhydrous tetrahydrofuran (20 mL). The resulting mixture was allowed to warm up slowly to room temperature and stirred overnight. The next morning the reaction mixture was partitioned between ethyl acetate and water. The organic layer was collected, dried over sodium sulfate, filtered, concentrated and the residue was purified by chromatography on a silica gel column with a 0–70% ethyl acetate in hexanes gradient. The product from this purification was dissolved in aniline (3 mL) and the mixture heated at 80° C. for 12 hours. The mixture was then cooled and purified by silica gel column chromatography using a 0–100% ethyl acetate in hexanes to 0–50% tetrahydrofuran in ethyl acetate gradient to afford the product. After a precipitation out of THF with excess of pentane 3-[3-(4-methoxy-phenyl)-2-oxo-7-phenylamino-3,4-dihydro-2H-pyrimido[4,5-d]pyrimidin-1-yl]-piperidine-1-carboxylic acid tert-butyl ester was isolated as an off-white solid. (Yield 70 mg, 10%).

HRMS m/z calcd for $C_{29}H_{34}N_6O_4$ [(M+H)$^+$]: 531.2715. Found: 531.2725.

Example 4b 3-(4-Methoxy-phenyl)-7-phenylamino-1-piperidin-3-yl-3,4-dihydro-1H-pyrimido[4,5-d]pyrimidin-2-one

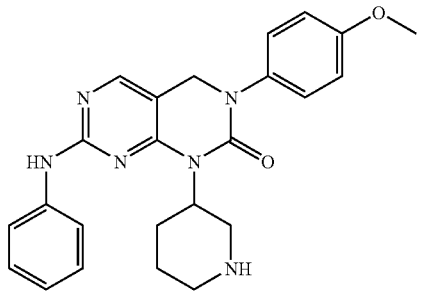

3-[3-(4-Methoxy-phenyl)-2-oxo-7-phenylamino-3,4-dihydro-2H-pyrimido[4,5-d]pyrimidin-1-yl]-piperidine-1-carboxylic acid tert-butyl ester (70 mg, 0.13 mmols) (from Example 4a supra) was dissolved at 0° C. in a 50% trifluoroacetic acid in dichloromethane solution (5 mL) that contained water (300 μL). After stirring for 1.5 hours the reaction mixture was partitioned between ethyl acetate and 1 N aqueous sodium hydroxide and the pH of the aqueous layer was adjusted to 12 by adding solid sodium hydroxide. The organic layer was then washed with water, dried over sodium sulfate, filtered and concentrated to the crude product. This material was dissolved in tetrahydrofuran and precipitated with an excess of pentane to give 3-(4-methoxyphenyl)-7-phenylamino-1-piperidin-3-yl-3,4-dihydro-1H-pyrimido[4,5-d]pyrimidin-2-one as an off-white solid. (Yield 47 mg, 84%).

HRMS m/z calculated for $C_{24}H_{27}N_6O_2$ [(M+H)$^+$]: 431.2190. Found: 431.2193

Example 5

1-Cyclopentyl-3-(4-methoxy-phenyl)-7-phenylamino-3,4-dihydro-1H-pyrimido[4,5-d]pyrimidin-2-one

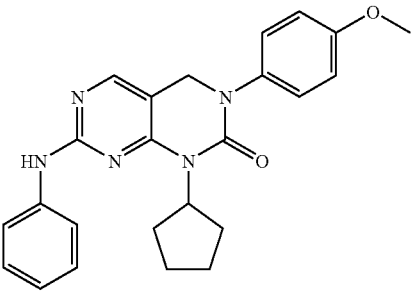

A solution of (2,4-dichloro-pyrimidin-5-yl-methyl)-(4-methoxyphenyl)-amine (350 mg, 1.23 mmol) (from Example 1d supra) in anhydrous tetrahydrofuran (30 mL) was treated with n-butyllithium (2.5 M solution in hexanes, 590 μL, 1.48 mmol) (Aldrich) at −78° C. Then cyclopentyl isocyanate (170 μL, 164 mg, 1.48 mmol) (Aldrich) was added and the solution was allowed to slowly warm up to room temperature and stirred for 5 hours. The reaction mixture was then partitioned between ethyl acetate and brine and the organic layer was collected, dried over sodium sulfate, filtered and concentrated and the residue was purified on a silica gel column with a 0–50% ethyl acetate in hexanes gradient. The intermediate from this purification was dissolved in aniline (3 mL) (Aldrich), a catalytic amount of 4-(dimethylamino)pyridine (Aldrich) was added and the resulting solution stirred at 100° C. for 17 hours. The reaction mixture was then cooled and purified by silica gel column chromatography with a 0–50% ethyl acetate in hexanes gradient to give the product. After a precipitation out of THF with an excess of pentane, 1-cyclopentyl-3-(4-methoxy-phenyl)-7-phenylamino-3,4-dihydro-1H-pyrimido[4,5-d]pyrimidin-2-one was isolated as an off-white solid. (Yield 49 mg, 9%).

HRMS m/z calcd for $C_{24}H_{25}N_5O_2$ [M$^+$]: 415.2008. Found: 415.2014.

Example 6

1-(1,1-Dioxo-tetrahydrothiophen-3-yl)-3-(4-methoxy-phenyl)-7-phenylamino-3,4-dihydro-1H-pyrimido[4,5-d]pyrimidin-2-one

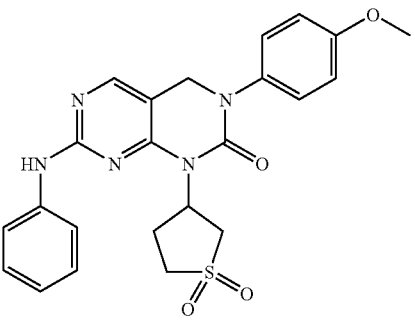

A mixture of 1,1-dioxidotetrahydrothien-3-ylamine (200 mg, 1.48 mmol) (Salor) and triethylamine (590 mg, 820 μL, 5.9 mmol) (Aldrich) in dichloromethane (9 mL) was treated with a 20% phosgene solution in toluene (1.80 mL, 3.70 mmol) (Fluka) at 0° C. After 30 minutes the mixture was filtered and the filtrate was concentrated to a small volume. Benzene (5 mL) was added, the mixture was filtered again and the filtrate was added to a solution of (2,4-dichloro-pyrimidin-5-yl-methyl)-(4-methoxyphenyl)-amine (230 mg, 1.43 mmol) (from Example 1d supra) in benzene (15 mL). The resulting solution was heated at reflux overnight. The next morning the solvent was evaporated under reduced pressure to a residue that was chromatographed with a silica gel column using a 0–100% ethyl acetate in hexanes gradient. The intermediate isolated from this purification was then dissolved in anhydrous tetrahydrofuran (15 mL) and the resulting solution was cooled at −78° C. and treated with n-butyllithium (2.5 M solution in hexanes, 330 μL, 0.82 mmol) (Aldrich). The mixture was allowed to warm up slowly to room temperature, stirred for 5.5 hours, and then partitioned between ethyl acetate and brine. The organic layer was collected, dried over sodium sulfate, filtered, concentrated and the resulting residue was dissolved in aniline (3 mL) (Aldrich). A catalytic amount of 4-(dimethylamino)pyridine (Aldrich) was added, and the mixture was stirred at 75° C. for 14 hours. The mixture was then cooled and purified by silica gel column chromatography using a 0–100% ethyl acetate in hexanes gradient to afford the product. After precipitation out of methylene chloride with excess of pentane the product, 1-(1,1-dioxo-tetrahydrothiophen-3-yl)-3-(4-methoxy-phenyl)-7-phenylamino-3,4-dihydro-1H-pyrimido[4,5-d]pyrimidin-2-one, was isolated as an off-white solid. (Yield 152 mg, 23%).

HRMS m/z calcd for $C_{23}H_{23}N_5O_4S$ [M$^+$]: 465.1471. Found: 465.1477.

Example 7

3-[3-(4-Methoxy-phenyl)-2-oxo-7-phenylamino-3,4-dihydro-2H-pyrimido[4,5-d]pyrimidin-1-yl]piperidine-1-carbaldehyde

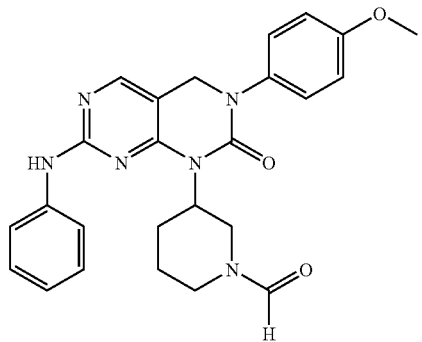

3-(4-Methoxy-phenyl)-7-phenylamino-1-piperidin-3-yl-3,4-dihydro-1H-pyrimido[4,5-d]pyrimidin-2-one (95 mg, 0.22 mmol) (from Example 4b supra) was dissolved at room temperature in methylformate (5 mL) (Aldrich). After stirring overnight the reaction mixture was concentrated to the crude product, which was purified by silica gel column chromatography with a 0–100% ethyl acetate in hexanes and then a 0–20% tetrahydrofuran in ethyl acetate gradient. After a precipitation out of dichloromethane with excess of pentane, 3-[3-(4-methoxy-phenyl)-2-oxo-7-phenylamino-3,4-dihydro-2H-pyrimido[4,5-d]pyrimidin-1-yl]-piperidine-1-carbaldehyde was isolated as an off-white solid. (Yield 90 mg, 89%).

HRMS m/z calcd for $C_{25}H_{26}N_6O_3$ [M$^+$]: 458.2066. Found: 458.2062.

Example 8

3-(4-Methoxy-phenyl)-7-phenylamino-1-(tetrahydro-pyran-4-yl)-3,4-dihydro-1H-pyrimido[4,5-d]pyrimidin-2-one

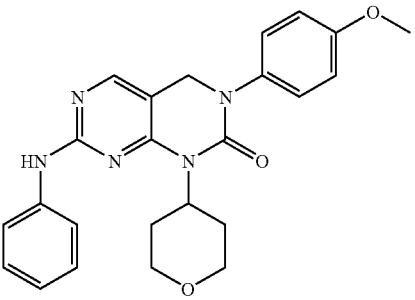

A mixture of 4-aminotetrahydropyran (300 mg, 2.88 mmol) (Combi-Blocks) and triethylamine (1.61 mL, 11.52 mmol) (Aldrich) in dichloromethane (6 mL) was treated with a 20% phosgene solution in toluene (1.4 mL, 5.76 mmol) (Fluka) at 0° C. After stirring for 30 min the mixture was filtered and the filtrate was concentrated to a small volume. Benzene (5 mL) was added and the mixture was filtered again. The filtrate was concentrated and the residue was dissolved in anhydrous tetrahydrofuran (approximately 3 mL) and transferred via a cannula to a −78° C. solution of (2,4-dichloro-pyrimidin-5-yl-methyl)-(4-methoxyphenyl)-amine (300 mg, 1.44 mmol) (from Example 1d supra) and n-butyllithium (2.5 M solution in hexanes, 460 μL, 1.44 mmol) (Aldrich) in tetrahydrofuran (15 mL). The reaction mixture was allowed to warm up slowly to room temperature, stirred overnight and then partitioned between ethyl acetate and brine. The ethyl acetate layer was collected, dried over sodium sulfate, filtered, concentrated and the residue was purified by chromatography with a silica gel column using a 0–70% ethyl acetate in hexanes gradient. The intermediate obtained from this purification was dissolved in aniline (2 mL) (Aldrich). A catalytic amount of 4-(dimethylamino)pyridine was added and the resulting solution stirred at 110° C. for 11 hours. The reaction mixture was then cooled and purified by silica gel column chromatography using a 0–100% ethyl acetate in hexanes gradient to afford the product. After a precipitation out of dichloromethane with excess of pentane the product, 3-(4-methoxy-phenyl)-7-phenylamino-1-(tetrahydropyran-4-yl)-3,4-dihydro-1H-pyrimido[4,5-d]pyrimidin-2-one, was isolated as an off-white solid. (Yield 15 mg, 2%).

HRMS m/z calcd for $C_{24}H_{25}N_5O_3$ [M$^+$]: 431.1957. Found: 431.1948.

Example 9a (±)-cis-3-(tert-Butyl-dimethyl-silanyloxy)-cyclopentanol

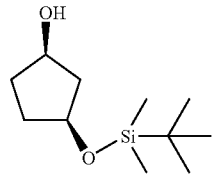

(±)-cis-tert-Butyl-dimethyl-(6-oxa-bicyclo[3.1.0]hex-3-yloxy)-silane (2.15 g, 9.99 mmol) (prepared according to the procedure of Hendrie, S. K., Leonard, J. Tetrahedron, 1987, 43 (14), 3289–3294) was dissolved in ethanol (70 mL). To this solution was added 10% Pd/C (500 mg) (Aldrich) and the mixture was hydrogenated under 1 atmosphere of hydrogen for 24 hours and at 50 psi for another 24 hours. Another portion of 10% Pd/C (500 mg) was added and the mixture was hydrogenated again at 55 psi for 24 hours. The hydrogenation mixture was then filtered, the solids were washed with tetrahydrofuran (approx. 60 mL) and the combined organic layer was concentrated. The residue was purified by chromatography on a silica gel column with 0–100% diethyl ether in hexanes to give (±)-cis-3-(tert-butyl-dimethyl-silanyloxy)-cyclopentanol as a colorless viscous oil. (Yield 1.81 g, 83%).

HRMS m/z calcd for $C_{11}H_{24}O_2Si$ [(M+H)$^+$]: 217.1618. Found: 217.1619.

Example 9b (±)-trans-(3-Azido-cyclopentyloxy)-tert-butyl-dimethyl-silane

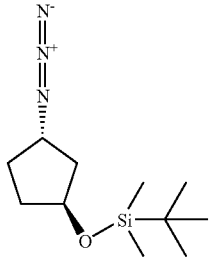

To a mixture of (±)-cis-3-(tert-butyl-dimethyl-silanyloxy)-cyclopentanol (1.5 g, 6.93 mmol) (from Example 9a supra) and triphenylphosphine (1.99 g, 7.63 mmol) (Aldrich) in anhydrous tetrahydrofuran (60 mL) was added dropwise diethyl azodicarboxylate (1.2 mL, 1.32 g, 7.63 mmol) (Aldrich) at 0° C. Then after 2 minutes this was followed by the addition of diphenylphosphoryl azide (1.6 mL, 2.09 g, 7.63 mmol) (Aldrich) and the resulting solution was allowed to slowly warm up to room temperature. After stirring overnight the reaction mixture was partitioned between diethyl ether and water. The organic layer was collected, dried over sodium sulfate, filtered, and concentrated and the residue was purified by chromatography on a silica gel column using a 0–20% diethyl ether in hexanes gradient to give (±)-trans-(3-azido-cyclopentyloxy)-tert-butyl-dimethyl-silane as a colorless liquid. (Yield 1.2 g, 72%).

Example 9c (±)-trans-3-(tert-Butyl-dimethyl-silanyloxy)-cyclopentylamine

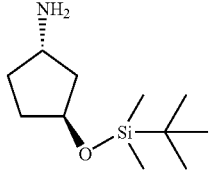

A mixture of (±)-trans-(3-azido-cyclopentyloxy)-tert-butyl-dimethyl-silane (400 mg, 1.66 mmol) (from Example 9b supra) and platinum oxide (38 mg, 0.17 mmol) (Aldrich) in ethanol (6 mL) was stirred under 1 atmosphere of hydrogen pressure for 2 hours. The reaction mixture was then filtered. The solids were washed with tetrahydrofuran (approx. 40 mL) and the combined organic layer was evaporated under reduced pressure to give (±)-trans-3-(tert-butyl-dimethyl-silanyloxy)-cyclopentylamine as a colorless liquid. (Yield 270 mg, 76%).

HRMS m/z calcd for $C_{11}H_{25}NOSi$ [(M+H)$^+$]: 216.1778. Found: 217.1780.

Example 9d (±)-1-(trans-3-Hydroxy-cyclopentyl)-3-(4-methoxy-phenyl)-7-phenylamino-3,4-dihydro-1H-pyrimido[4,5-d]pyrimidin-2-one Racemic

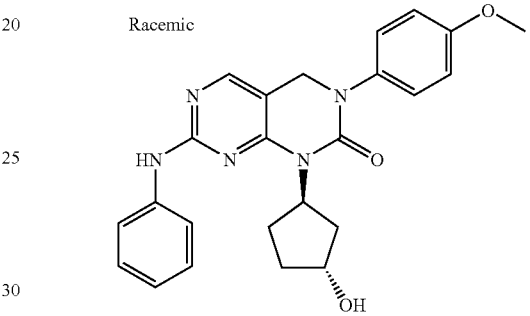

A solution of (±)-trans-3-(tert-butyl-dimethyl-silanyloxy)-cyclopentylamine (270 mg, 1.25 mmol) (from Example 9b supra) and triethylamine (1.15 mL, 840 mg, 8.30 mmol) (Aldrich) in dichloromethane (5 mL) was treated at 0° C. with a 20% solution of phosgene in toluene (2 mL, 4.15 mmol) (Fluka). After stirring for 30 minutes the mixture was filtered and the filtrate was concentrated to a small volume. Benzene (5 mL) was added and the mixture was filtered again. The filtrate was concentrated, the residue was dissolved in a small volume of anhydrous tetrahydrofuran (approx. 3 mL) and then transferred via a cannula to a −78° C. solution of (2,4-dichloro-pyrimidin-5-yl-methyl)-(4-methoxyphenyl)-amine (180 mg, 0.63 mmol) (from Example 1d supra) and n-butyllithium (2.5 M solution in hexanes, 250 µL, 0.63 mmol) (Aldrich) in anhydrous tetrahydrofuran (15 mL). The reaction mixture was allowed to slowly warm up to room temperature, stirred for 5.5 hours and then partitioned between ethyl acetate and water. The organic layer was collected, dried over sodium sulfate, filtered, concentrated and the residue was purified by chromatography on a silica gel column with a 0–40% ethyl acetate in hexanes gradient. The intermediate obtained from this purification was dissolved in aniline (2 mL) (Aldrich), a catalytic amount of 4-(dimethylamino)pyridine (Aldrich) was added and the resulting solution was stirred for 7 hours at 80° C. The mixture was then cooled and purified by silica gel column chromatography using a 0–40% ethyl acetate in hexanes gradient. The product from this purification was dissolved in acetonitrile (3 mL), 5% aqueous hydrofluoric acid (50 µL) was added and the mixture was stirred for 21 hours. The reaction mixture was then concentrated to a small volume and purified by silica gel column chromatography using a 0–100% tetrahydrofuran in hexanes gradient to afford the product. After a precipitation out of dichloromethane with excess of pentane, the product, (±)-1-(trans- 3-hydroxy-cyclopentyl)-3-(4-methoxy-phenyl)-7-phenylamino-3,4-dihydro-1H-pyrimido[4,5-d]pyrimidin-2-one, was isolated as a white solid. (Yield 23 mg, 8%).

HRMS m/z calculated for $C_{24}H_{25}N_5O_3$ $[(M+H)]^+$: 480.1467. Found: 480.1471.

Example 10a (±)-trans-3-(tert-Butyl-dimethyl-silanyloxy)-cyclopentanol

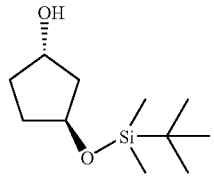

To a mixture of 1,3-cyclopentanediol (5.0 g, 48.9 mmol) (cis/trans mixture, Aldrich) and imidazole (3.3 g, 48.5 mmol) in tetrahydrofuran (100 mL) at 0° C. was added tert-butyldimethylsilyl chloride (5.2 g, 34.3 mmol) (Aldrich) in portions (250 mg every 15 minutes). When all additions were completed the reaction mixture was allowed to slowly warm to room temperature. After stirring overnight the mixture was partitioned between ethyl acetate and water. The organic layer was collected, dried over sodium sulfate, filtered and concentrated. The residue was purified by chromatography on a silica gel column with a 0–20% ethyl acetate in hexanes gradient to give (±)-trans-3-(tert-butyl-dimethyl-silanyloxy)-cyclopentanol as a colorless viscous oil, (Yield 4.23 g, 57%), and (±)-cis-3-(tert-butyl-dimethyl-silanyloxy)-cyclopentanol (Yield 420 mg, 6%).

HRMS m/z calcd for $C_{11}H_{24}O_2Si$ $[M+H]^+$: 217.1618. Found: 217.1621.

Example 10b (±)-cis-2-[3-(tert-Butyl-dimethyl-silanyloxy)-cyclopentyl]-isoindole-1,3-dione

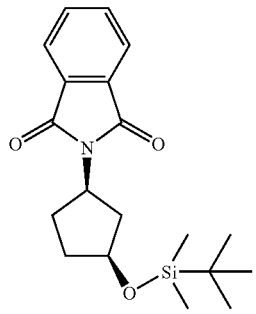

A solution of (±)-trans-3-(tert-butyl-dimethyl-silanyloxy)-cyclopentanol (1.1 g, 5.08 mmol) (from Example 10a supra), triphenylphosphine (3.2 g, 12.20 mmol) (Aldrich) and phthalimide (1.8 g, 12.20 mmol) (Aldrich) in anhydrous tetrahydrofuran (45 mL) was cooled to 0° C. To this was added dropwise diethyl azodicarboxylate (2.1 mL, 2.3 g, 12.20 mmol) (Aldrich) and the resulting solution was allowed to slowly warm to room temperature. After stirring overnight the reaction mixture was partitioned between ethyl acetate and water. The organic layer was collected, dried over sodium sulfate, filtered and concentrated and the residue was purified by chromatography on a silica gel column using a 0–35% ethyl acetate in hexanes gradient to give (±)-cis-2-[3-(tert-butyl-dimethyl-silanyloxy)-cyclopentyl]-isoindole-1,3-dione as a white solid. (Yield 1.52 g, 87%).

HRMS m/z calcd for $C_{19}H_{27}NO_3Si$ $[M—CH_3]^+$: 330.1525. Found: 330.1523.

Example 10c (±)-cis-3-(tert-Butyl-dimethyl-silanyloxy)-cyclopentylamine

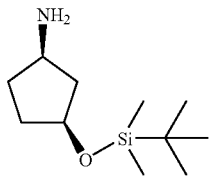

To a mixture of (±)-cis-2-[3-(tert-butyl-dimethyl-silanyloxy)-cyclopentyl]-isoindole-1,3-dione (1.03 g, 2.98 mmol) (from Example 10b supra) in ethanol/tetrahydrofuran (2:1, 20 mL) was added anhydrous hydrazine (1.2 mL, 38.90 mmol) (Aldrich). After stirring overnight the reaction mixture was filtered. The solids were washed with diethyl ether (approx. 30 mL) and the combined filtrate was concentrated. The residue was treated with diethyl ether again (approx. 30 mL) and the resulting mixture was filtered again and concentrated to give (±)-cis-3-(tert-butyl-dimethyl-silanyloxy)-cyclopentylamine as a colorless oil. (Yield 570 mg, 88%).

HRMS m/z calcd for $C_{11}H_{25}NOSi$ $[M+H]^+$: 216.1778. Found: 216.1780.

Example 10d (±)-3-cis-(tert-Butyl-dimethyl-silanyloxy)-cyclopentyl-3-(4-methoxyphenyl)-7-phenylamino-3,4-dihydro-1H-pyrimido[4,5-d]pyrimidin-2-one

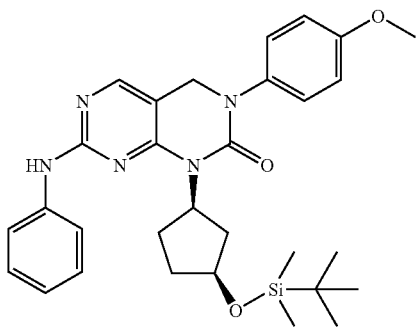

A solution of (±)-cis-3-(tert-butyl-dimethyl-silanyloxy)-cyclopentylamine (500 mg, 2.32 mmol) (from Example 10c supra) and triethylamine (1.62 mL, 1.2 g, 11.64 mmol) (Aldrich) in dichloromethane (15 mL) at 0° C. was treated with a 20% solution of phosgene in toluene (2.8 mL, 5.80 mmol) (Fluka). After stirring for 30 minutes the mixture was filtered and the filtrate was concentrated to a small volume. Benzene (5 mL) was added and this mixture was filtered again. The filtrate was then concentrated, the residue was dissolved in anhydrous tetrahydrofuran (approximately 3 mL) and then transferred via cannula to a −78° C. solution of (2,4-dichloro-pyrimidin-5-yl-methyl)-(4-methoxyphenyl)-amine (330 mg, 1.16 mmol) (from Example 1d supra) and n-butyllithium (2.5 M solution in hexanes, 460 µL, 1.16 mmol) (Aldrich) in anhydrous tetrahydrofuran (25 mL). The reaction mixture was allowed to slowly warm up to room temperature, stirred for 48 hours and then partitioned between ethyl acetate and water. The organic layer was collected, dried over sodium sulfate, filtered and concentrated and the residue was purified by silica gel column chromatography using a 0–30% ethyl acetate in hexanes gradient. The intermediate that was obtained from this purification was dissolved in aniline (2 mL) (Aldrich). A catalytic amount of 4-(dimethyl-amino)pyridine (Aldrich) was added and the resulting solution was stirred for 8 hours at 80° C. The reaction mixture was then cooled and purified by silica gel column chromatography using a 0–100% ethyl acetate in hexanes gradient to give (±)-3-cis-(tert-butyl-dimethyl-silanyloxy)-cyclopentyl-3-(4-methoxy-phenyl)-7-phenylamino-3,4-dihydro-1H-pyrimido[4,5-d]pyrimidin-2-one as a white solid. (Yield 100 mg, 16%).

HRMS m/z calcd for $C_{30}H_{39}N_5O_3Si$ [M+H]$^+$: 546.2895. Found: 546.2901.

Example 10e (±)-cis-1-(3-Hydroxy-cyclopentyl)-3-(4-methoxy-phenyl)-7-phenylamino-3,4-dihydro-1H-pyrimido[4,5-d]pyrimidin-2-one

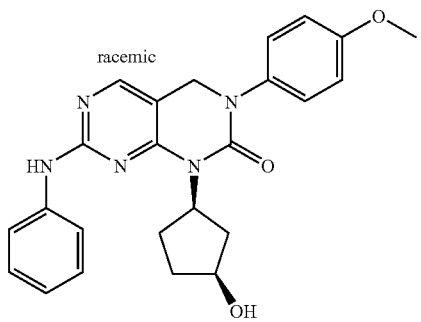

To a solution of (±)-3-cis-(tert-butyl-dimethyl-silanyloxy)-cyclopentyl-3-(4-methoxy-phenyl)-7-phenylamino-3,4-dihydro-1H-pyrimido[4,5-d]pyrimidin-2-one (100 mg, 0.18 mmol) (from Example 10d supra) in acetonitrile (3 mL) was added a 5% aqueous hydrofluoric acid solution (110 µL, 0.275 mmol). After stirring overnight the reaction mixture was concentrated to a small volume (~1 mL) and purified by silica gel column chromatography using a 0–100% ethyl acetate in hexanes gradient. After a precipitation out of methylene chloride with excess of pentane, the product, (±)-cis-1-(3-hydroxy-cyclopentyl)-3-(4-methoxy-phenyl)-7-phenylamino-3,4-dihydro-1H-pyrimido[4,5-d]pyrimidin-2-one, was isolated as a white solid. (Yield 60 mg, 77%).

HRMS m/z calcd for $C_{24}H_{25}N_5O_3$ [M+H]$^+$: 432.2030. Found: 432.2033.

Example 11a (R)-2-Methylsulfanyl-4-(tetrahydrofuran-3-ylamino)-pyrimidine-5-carboxylic acid ethyl ester

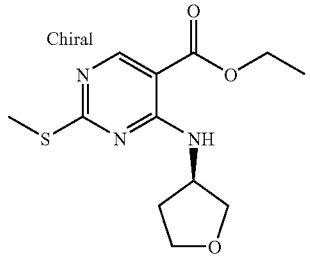

A solution of ethyl 4-chloro-2-methylthio-5-pyrimidinecarboxylate (897 mg, 3.86 mmol) (Aldrich) and triethylamine (1.2 mL, 870 mg, 8.49 mmol) (Aldrich) in dioxane (20 mL) was treated with (R)-3-aminotetrahydrofuran p-toluene-sulfonic acid salt (1.0 g, 3.86 mmol) (Fluka). The mixture was stirred at reflux for 1 hour, then cooled and partitioned between brine and ethyl acetate. The organic layer was dried over sodium sulfate, filtered, concentrated and the residue was purified by chromatography with a silica gel column using a 0–100% ethyl acetate in hexanes gradient to give (R)-2-methylsulfanyl-4-(tetrahydrofuran-3-ylamino)-pyrimidine-5-carboxylic acid ethyl ester as a colorless viscous oil. (Yield 1.0 g, 92%).

HRMS m/z calcd for $C_{12}H_{17}N_3O_3S$ [M$^+$]: 283.0991. Found: 283.0989.

Example 11b (R)-3-(4-Methoxy-phenyl)-7-phenylamino-1-(tetrahydrofuran-3-yl)-3,4-dihydro-1H-pyrimido[4,5-d]pyrimidin-2-one

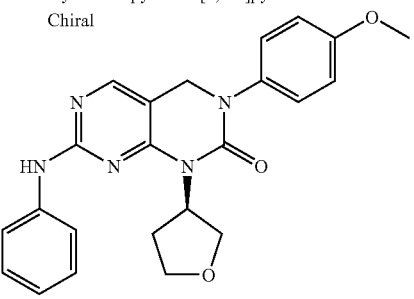

To a solution of (R)-2-methylsulfanyl-4-(tetrahydrofuran-3-ylamino)-pyrimidine-5-carboxylic acid ethyl ester (1.0 g, 3.55 mmol) (from Example 11a supra) at 0° C. in anhydrous tetrahydrofuran (60 mL) was added in portions solid lithium aluminum hydride (400 mg, 10.65 mmol) (Aldrich). The resulting slurry was allowed to slowly warm up to room temperature. After overnight stirring the slurry was poured slowly into a vigorously stirred mixture of ethyl acetate and saturated aqueous potassium sodium tartrate solution. The organic layer was separated, dried over sodium sulfate, filtered and concentrated to give the crude reduction product. This crude intermediate was dissolved in dichloromethane (30 mL) and treated with manganese dioxide (2.9 g, 34.27 mmol) (Aldrich). After stirring for 2 hours the solids were filtered, washed with tetrahydrofuran (approx. 30 mL), the combined filtrate was concentrated and the residue was dissolved in toluene (40 mL). The solution was then treated with p-anisidine (470 mg, 3.77 mmol) (Aldrich), a catalytic amount of p-toluenesulfonic acid monohydrate (Aldrich) was added and the mixture was heated at reflux using a Dean-Stark apparatus for 3 hours. The mixture was then cooled and partitioned between ethyl acetate and saturated aqueous potassium carbonate. The ethyl acetate layer was collected, dried over sodium sulfate, filtered, and concentrated to a residue that was then dissolved in tetrahydrofuran (40 mL). The resulting solution was treated at 0° C. with lithium aluminum hydride (390 mg, 10.28 mmol) (Aldrich). The slurry was allowed to slowly warm to room temperature and after stirring for 13.5 hours was poured slowly into a vigorously stirred mixture of ethyl acetate and saturated aqueous potassium sodium tartrate solution. The organic layer was separated, dried over sodium sulfate, filtered, concentrated and the resulting residue was purified by silica gel column chromatography using a 0–70% ethyl acetate in hexanes gradient. The intermediate isolated from this purification was dissolved in tetrahydrofuran (50 mL). Triethylamine (1 mL) (Aldrich) was added and the solution was cooled to 0° C. Followed a dropwise addition of 20% phosgene in toluene solution (1.3 mL, 2.71 mmol) (Fluka) and stirring at 0° C. for 1.5 hours. The mixture was then partitioned between ethyl acetate and water. The organic layer was collected, dried over sodium sulfate, filtered and concentrated to a residue that was purified by chromatography on a silica gel column with a 0–40% ethyl acetate in hexanes gradient. The intermediate isolated from this purification was dissolved in tetrahydrofuran (50 mL) and the resulting solution was cooled at 0° C. and treated with 3-chloroperoxybenzoic acid (75%, 1.13 g, 4.93 mmol) (Aldrich). The reaction mixture was allowed to slowly warm up to room temperature and after stirring overnight was partitioned between ethyl acetate and water. The organic layer was collected, dried over sodium sulfate, filtered and concentrated. The residue was dissolved in aniline (10 mL) (Aldrich), a catalytic amount of aniline hydrochloride (Aldrich) was added and the resulting solution was stirred for 4.5 hours at 95° C. The mixture was then cooled and purified by silica gel column chromatography using a 0–100% ethyl acetate in hexanes gradient to afford the product. Trituration with pentane yielded (R)-3-(4-methoxy-phenyl)-7-phenylamino-1-(tetrahydrofuran-3-yl)-3,4-dihydro-1H-pyrimido[4,5-d]pyrimidin-2-one as an off-white solid. (Yield 740 mg, 50%).

HRMS m/z calcd for $C_{23}H_{23}N_5O_3[M+H^+]$: 418.1874. Found: 418.1877.

Example 12

A solution of (R)-1-N-Boc-3-aminopyrrolidine (350 mg, 1.88 mmol) (AstaTech Inc.) and triethylamine (1.31 mL, 0.95 g, 9.4 mmol) (Aldrich) in dichloromethane (6 mL) at 0° C. was treated with 20% phosgene in toluene solution (1.84 mL, 3.76 mmol) (Fluka). After stirring for 30 minutes the reaction mixture was filtered and concentrated to a small volume. Benzene (5 mL) was added and the mixture was filtered again. The filtrate was concentrated, dissolved in a small volume of anhydrous tetrahydrofuran (approx. 3 mL) and transferred via cannula to a −78° C. solution of (2,4-dichloro-pyrimidin-5-yl-methyl)-(4-methoxyphenyl)-amine (270 mg, 0.94 mmol) (from Example 1d supra) and n-butyllithium (2.5 M solution in hexanes, 380 μL, 0.94 mmol) (Aldrich) in anhydrous tetrahydrofuran (12 mL). The reaction mixture was allowed to slowly warm up to room temperature stirred overnight and then partitioned between ethyl acetate and water. The organic layer was collected, dried over sodium sulfate, filtered, concentrated and the resulting residue was purified by chromatography on a silica gel column using a 0–70% ethyl acetate in hexanes gradient. The intermediate obtained from that purification was then dissolved in aniline (2 mL) (Aldrich), a catalytic amount of aniline hydrochloride (Aldrich) was added and the solution was stirred at 85° C. for 8 hours. The mixture was then cooled and purified by silica gel column chromatography with a 0–70% ethyl acetate in hexanes gradient. The product from that purification was then dissolved at 0° C. in a 50% trifluoroacetic acid in dichloromethane solution (6 mL) that contained water (300 μL) and stirred for 1.5 hours. The reaction mixture was then partitioned between ethyl acetate and 0.5 N aqueous sodium hydroxide. The pH of the aqueous layer was adjusted to 12 by adding solid sodium hydroxide. The organic layer was then collected, dried over sodium sulfate, filtered and concentrated to the crude product which was purified by chromatography with a silica gel column using a 0–100% methanol in tetrahydrofuran to 0–20% triethylamine in methanol gradient. The fractions containing the product were concentrated to a solid that was then dissolved in dichloromethane (approximately 5 mL). That solution was filtered and treated with excess of pentane to precipitate (R)-3-(4-methoxy-phenyl)-7-phenylamino-1-pyrrolidin-3-yl-3,4-dihydro-1H-pyrimido[4,5-d]pyrimidin-2-one as an off-white solid. (Yield 14 mg, 2%).

HRMS m/z calcd for $C_{23}H_{24}N_6O_2$ [M+H$^+$]: 417.2034. Found: 417.2038.

Example 13a (R)-3-(4-Methoxy-phenyl)-7-phenylamino-1-prrrolidin-3-yl-3,4-dihydro-1H-pyrimido[4,5-d]pyrimidin-2-one

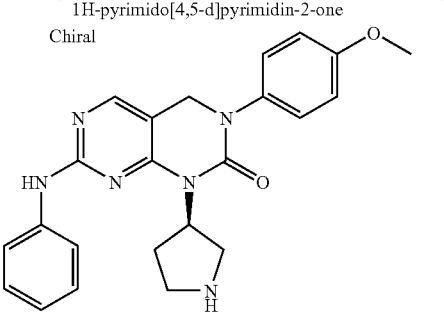

(±)-4-[trans-3-(tert-Butyl-dimethyl-silanyloxy)-cyclopentylamino]-2-methylsulfanyl-pyrimidine-5-carbaldehyde

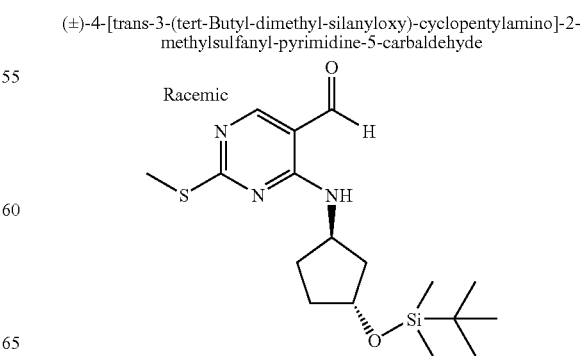

A solution of 4-chloro-2-methylthio-5-pyrimidinecarboxylate (900 mg, 3.87 mmol) (Aldrich) and triethylamine (1.1 mL, 870 mg, 7.74 mmol) (Aldrich) in dioxane (50 mL) was treated with (±)-trans-3-(tert-butyl-dimethyl-silanyloxy)-cyclopentylamine (840 mg, 3.87 mmol) (from Example 9c supra). The mixture was stirred at reflux for 1 hour, then cooled and partitioned between brine and ethyl acetate. The organic layer was collected, dried over sodium sulfate, filtered and concentrated to a residue that was purified by silica gel column chromatography using a 0–20% ethyl acetate in hexanes gradient. The product isolated from this purification was then dissolved in anhydrous tetrahydrofuran (80 mL) and the resulting solution was cooled to 0° C. Followed addition in-portions of lithium aluminum hydride (440 mg, 11.61 mmol) (Aldrich) and the resulting mixture was allowed to warm to room temperature. After overnight stirring the reaction mixture was poured slowly into a vigorously stirred mixture of ethyl acetate and saturated aqueous potassium sodium tartrate solution. The organic layer was collected, dried over sodium sulfate, filtered and concentrated to an off white solid. This intermediate was then dissolved in dichloromethane (80 mL) and the resulting solution was treated with manganese dioxide (3.36 g, 38.70 mmol) (Aldrich). After overnight stirring the solids were filtered off, washed with tetrahydrofuran (approximately 30 mL) and the combined organic layer was concentrated to a residue that upon a silica gel column purification with 0–50% diethyl ether in hexanes gradient gave (±)-4-[trans-3-(tert-butyl-dimethyl-silanyloxy)-cyclopentylamino]-2-methylsulfanyl-pyrimidine-5-carbaldehyde as a viscous colorless oil. (Yield 888 mg, 62%).

HRMS m/z calcd for $C_{17}H_{29}N_3O_2SSi$ $[M+H]^+$: 368.1823. Found: 368.1826.

Example 13b (±)-1-[trans-3-(tert-Butyl-dimethyl-silanyloxy)-cyclopentyl]-3-(4-methoxy-phenyl)-7-methylsulfanyl-3,4-dihydro-1H-pyrimido[4,5-d]pyrimidin-2-one

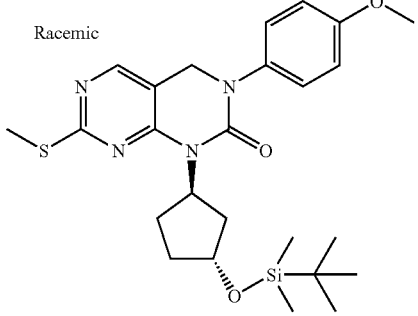

A mixture of (±)-4-[trans-3-(tert-butyl-dimethyl-silanyloxy)-cyclopentyl-amino]-2-methylsulfanyl-pyrimidine-5-carbaldehyde (700 mg, 1.90 mmol) (from Example 13a supra), p-anisidine (230 mg, 1.90 mmol) (Aldrich) and p-toluenesulfonic acid mono-hydrate (50 mg) (Aldrich) in benzene was refluxed using a Dean-Stark apparatus for 6 hours. The mixture was then cooled and partitioned between ethyl acetate and saturated aqueous potassium carbonate. The organic layer was collected, dried over sodium sulfate, filtered and concentrated. The residue was then dissolved in anhydrous tetrahydrofuran (60 mL) and to this solution at 0° C. was added in small portions lithium aluminum hydride (216 mg, 5.70 mmol) (Aldrich). The slurry that formed was allowed to slowly warm up to room temperature and after overnight stirring was poured slowly into a vigorously stirred mixture of ethyl acetate and saturated aqueous potassium sodium tartrate solution. The organic layer was collected, dried over sodium sulfate, filtered and concentrated. The residue was purified by HPLC using 50% diethyl ether in hexanes as the elution solvent. The intermediate obtained from this purification was dissolved in dichloromethane (100 mL), followed by addition of triethylamine (500 µL, 660 mg, 6.52 mmol) (Aldrich) and cooled at 0° C. A 20% phosgene in toluene solution (640 µL, 1.31 mmol) (Fluka) was then added dropwise and the resulting mixture was stirred for 30 minutes at 0° C. and 1 hour at room temperature. The mixture was then partitioned between ethyl acetate and water. The organic layer was separated, dried over sodium sulfate, filtered and concentrated to a residue that was purified by chromatography on a silica gel column with a 0–60% ethyl acetate in hexanes gradient to give (±)-1-[trans-3-(tert-butyl-dimethyl-silanyloxy)-cyclopentyl]-3-(4-methoxy-phenyl)-7-methylsulfanyl-3,4-dihydro-1H-pyrimido[4,5-d]pyrimidin-2-one as a white solid. (Yield 543 mg, 57%).

HRMS m/z calcd for $C_{25}H_{36}N_4O_3SSi$ $[M+H]^+$: 501.2350. Found: 501.2353.

Example 13c (±)-7-(4-Fluoro-phenylamino)-1-(trans-3-hydroxy-cyclopentyl)-3-(4-methoxy-phenyl)-3,4-dihydro-1H-pyrimido[4,5-d]pyrimidin-2-one

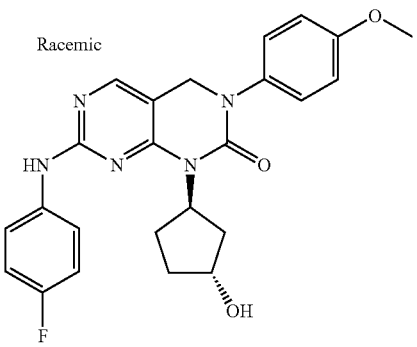

A solution of (±)-1-[trans-3-(tert-butyl-dimethyl-silanyloxy)-cyclopentyl]-3-(4-methoxy-phenyl)-7-methylsulfanyl-3,4-dihydro-1H-pyrimido[4,5-d]pyrimidin-2-one (40 mg, 0.08 mmol) (from Example 13b supra) in tetrahydrofuran (6 mL) was treated with 3-chloroperoxybenzoic acid (75%, 39 mg, 0.17 mmol) (Aldrich) at room temperature. After stirring for 3 hours the reaction mixture was partitioned between ethyl acetate and saturated aqueous potassium carbonate. The organic layer was separated, dried over sodium sulfate, filtered and concentrated. The residue was dissolved in 4-fluoroaniline (3 mL) (Aldrich) and the solution was stirred for 8 hours at 107° C. The reaction mixture was then cooled and purified by silica gel column chromatography using a 0–70% ethyl acetate in hexanes gradient. The product isolated from this purification was dissolved at 0° C. in a 20% trifluoroacetic acid in dichloromethane solution (5 mL) that contained water (500 µL). After stirring for 30 minutes the reaction mixture was partitioned between ethyl acetate and aqueous 1N sodium hydroxide solution. The pH of the aqueous layer was adjusted to 12 via the addition of solid sodium hydroxide. The organic layer was separated, dried over sodium sulfate, filtered and concentrated. The residue was purified by chromatography with a silica gel column using a 0–100% ethyl acetate in hexanes gradient to afford the product. After a precipitation out of methylene chloride with excess of pentane (±)-7-(4-fluorophenylamino)-1-(trans-3-hydroxy-cyclopentyl)-3-(4-methoxy-phenyl)-3,4-dihydro-1H-pyrimido[4,5-d]pyrimidin-2-one was isolated as a white solid. (Yield 25 mg, 69%).

HRMS m/z calcd for $C_{24}H_{24}FN_5O_3$ [M+H]$^+$: 450.1936. Found: 450.1940.

Example 14a

2-Fluoro-4-methoxyaniline

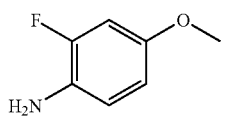

3-Fluoro-4-nitrophenol (10.17 g, 64.7 mmol) (Aldrich) was dissolved in dimethylformamide (210 mL). Potassium carbonate (45 g, 323 mmol) and methyl iodide (5 mL, 77.64 mmol) (Aldrich) were added and the reaction mixture was stirred at room temperature overnight. (TLC: 20% ethyl acetate in hexanes showed complete conversion). The reaction mixture was filtered through a bed of Celite®, and concentrated under reduced pressure. The crude material was triturated with ether and insoluble materials were removed by filtration. The filtrate was concentrated under reduce pressure to afford an orange solid. This material (11.43 g) was dissolved in methanol (150 mL) and hydrogenated for 1.5 hours in a Parr apparatus at 50 psi, in the presence of 10% palladium on carbon (1.5 g) (Aldrich). (TLC: 20% ethyl acetate in hexanes showed complete conversion). The reaction mixture was filtered through Celite® washed with ethyl acetate, then concentrated under reduced pressure to afford 2-fluoro-4-methoxyaniline as a solid. (Yield 3.81 g, 26.99 mmol).

Example 14b (±)-[3-trans-(tert-Butyl-dimethyl-silanyloxy)-cyclopentyl]-{5-[(2-fluoro-4-methoxy-phenylamino)-methyl]-2-methylsulfanyl-pyrimidin-4-yl}-amine Racemic

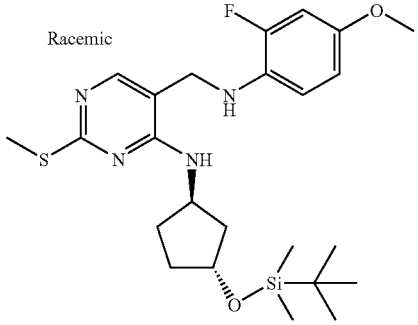

A mixture of (±)-4-[trans-3-(tert-butyl-dimethyl-silanyloxy)-cyclopentyl-amino]-2-methylsulfanyl-pyrimidine-5-carbaldehyde (171 mg, 0.46 mmol) (from Example 13a supra), p-toluenesulfonic acid mono-hydrate (10 mg) (Aldrich) and 2-fluoro-4-methoxyaniline (79 mg, 0.56 mmol) (from Example 14a supra) in benzene (30 mL) was refluxed in a Dean-Stark apparatus for 8 hours. The mixture was then cooled and partitioned between ethyl acetate and saturated aqueous potassium carbonate. The organic layer was collected, dried over sodium sulfate, filtered and concentrated. The residue was dissolved in anhydrous tetrahydrofuran (50 mL) and to this solution was added in small portions lithium aluminum hydride (53 mg, 1.40 mmol) (Aldrich) at 0° C. The slurry was allowed to slowly warm up to room temperature and after overnight stirring was poured slowly into a vigorously stirred mixture of ethyl acetate and saturated aqueous potassium sodium tartrate solution. The organic layer was collected, dried over sodium sulfate, filtered and concentrated to a residue that upon purification by silica gel column chromatography with a 0–60% ethyl acetate in hexanes gradient gave (±)-[3-trans-(tert-butyl-dimethyl-silanyloxy)-cyclopentyl]-{5-[(2-fluoro-4-methoxy-phenylamino)-methyl]-2-methylsulfanyl-pyrimidin-4-yl}-amine as a colorless viscous oil. (Yield 187 mg, 83%).

HRMS m/z calculated for $C_{24}H_{37}FN_4O_2SSi$ [M+H]$^+$: 493.2464. Found: 493.2472.

Example 14c (±)-1-[trans-3-(tert-Butyl-dimethyl-silanyloxy)-cyclopentyl]-3-(4-methoxy-phenyl)-7-methylsulfanyl-3,4-dihydro-1H-pyrimido[4,5-d]pyrimidin-2-one Racemic

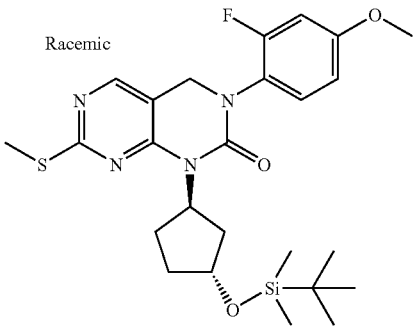

To a mixture of (±)-[3-trans-(tert-butyl-dimethyl-silanyloxy)-cyclopentyl]-{5-[(2-fluoro-4-methoxy-phenylamino)-methyl]-2-methylsulfanyl-pyrimidin-4-yl}-amine (179 mg, 0.36 mmol) (from Example 14b supra) and triethylamine (152 μL, 110 mg, 1.08 mmol) (Aldrich) in dichloromethane (30 mL) cooled to 0° C. was added dropwise a 20% phosgene in toluene solution (265 μL, 0.54 mmol) (Fluka). The resulting mixture was allowed to slowly warm to room temperature and stirred for 4.5 hours. The mixture was then partitioned between ethyl acetate and water. The organic layer was collected, dried over sodium sulfate, filtered and concentrated to a residue that was purified by chromatography on a silica gel column with a 0–10% diethyl ether in toluene gradient to give (±)-1-[trans-3-(tert-butyl-dimethyl-silanyloxy)-cyclopentyl]-3-(4-methoxy-phenyl)-7-methylsulfanyl-3,4-dihydro-1H-pyrimido[4,5-d]pyrimidin-2-one as an off white foamy solid. (Yield 84 mg, 45%).

HRMS m/z calcd for $C_{25}H_{35}FN_4O_3SSi$ [M+H]$^+$: 519.2256. Found: 519.2263.

Example 14d (±)-3-(2-Fluoro-4-methoxy-phenyl)-1-(trans-3-hydroxy-cyclopentyl)-7-phenylamino-3,4-dihydro-1H-pyrimido[4,5-d]pyrimidin-2-one

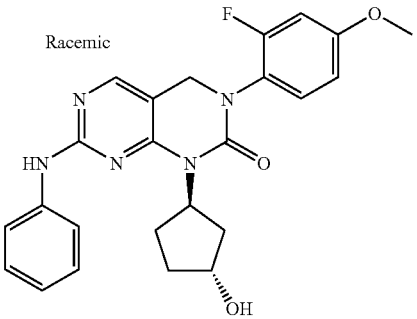

To a solution of (±)-1-[trans-3-(tert-butyl-dimethyl-silanyloxy)-cyclopentyl]-3-(4-methoxy-phenyl)-7-methylsulfanyl-3,4-dihydro-1H-pyrimido[4,5-d]pyrimidin-2-one (80 mg, 0.15 mmol) (from Example 14c supra) in dichloromethane (15 mL) was added 3-chloroperoxybenzoic acid (75%, 75 mg, 0.32 mmol) (Aldrich). The reaction mixture was stirred for 5.5 hours and then partitioned between ethyl acetate and saturated aqueous solution of potassium carbonate. The organic layer was separated, dried over sodium sulfate, filtered, concentrated and the residue that resulted was dissolved in aniline (2 mL) (Aldrich). This solution was stirred for 8 hours at 90° C. then cooled and purified by silica gel column chromatography using a 0–50% ethyl acetate in hexanes gradient. This was dissolved at 0° C. in a 20% trifluoroacetic acid in dichloromethane solution (5 mL) that contained water (300 μL). After stirring for 25 minutes the mixture was partitioned between ethyl acetate and 0.5N aqueous sodium hydroxide solution. The pH of the aqueous layer was adjusted to 12 by adding solid sodium hydroxide. The organic layer was then separated, dried over sodium sulfate, filtered and concentrated to the crude product. After purification by silica gel column chromatography with a 0–100% ethyl acetate in hexanes and a precipitation out of methylene chloride with excess of pentane the product, (±)-3-(2-fluoro-4-methoxy-phenyl)-1-(trans-3-hydroxy-cyclopentyl)-7-phenylamino-3,4-dihydro-1H-pyrimido[4,5-d]pyrimidin-2-one was isolated as a white solid. (Yield 45 mg, 65%).

HRMS m/z calculated for $C_{24}H_{24}FN_5O_3$ [M+H]$^+$: 450.1935. Found: 450.1941.

Example 15a (S)-3-(tert-Butyl-diphenyl-silanyloxy)-2-methylpropionic acid

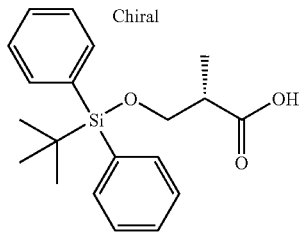

Methyl (S)-(±)-3-hydroxy-2-methylpropionate (1.06 g, 8.99 mmol) (Aldrich) was dissolved in dichloromethane (10 mL, dried over molecular sieves). Imidazole (0.85 g, 12.41 mmol) (Aldrich) and tert-butyldiphenylsilyl chloride (2.30 mL, 8.85 mmol) (Aldrich) were added and the mixture was stirred at ambient temperature for three hours. The reaction was diluted with additional dichloromethane, washed with water and brine, dried over anhydrous sodium sulfate and concentrated to yield methyl (S)-3-(tert-butyl-diphenyl-silanyloxy)-2-methyl-propionate as an oil. (Yield 3.17 g, 98.8%).

This ester (3.15 g, 8.85 mmol) was dissolved in 3:1 tetrahydrofuran-methanol (30 mL) and saponified with aqueous sodium hydroxide (1.0 N, 10.0 mL, 10.0 mmol) overnight at ambient temperature. After concentration, the residue was partitioned between ethyl acetate and water and then acidified (to pH 4–5) with 0.5N aqueous hydrochloric acid. The organic phase was washed with water and brine, dried over anhydrous sodium sulfate and concentrated. Purification was carried out with multiple flash chromatography runs using the Biotage system. Pure fractions from each run were combined and concentrated to yield (S)-3-(tert-butyl-diphenyl-silanyloxy)-2-methylpropionic acid as an oil that solidified to a tacky white solid in the cold. (Yield 2.10 g, 69.2%).

Example 15b (S)-tert-Butyl-2-isocyanato-propoxydiphenylsilane

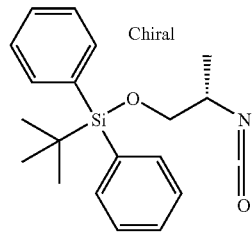

(S)-3-(tert-Butyl-diphenyl-silanyloxy)-2-methylpropionic acid (0.44 g, 1.20 mmol) (from Example 15a supra) was dissolved in dichloromethane (3 mL, dried over molecular sieves). Triethylamine (0.36 mL, 2.58 mmol) (Aldrich) was added and the solution was cooled in an ice-water bath. Ethyl chloroformate (0.16 mL, 1.67 mmol) (Aldrich) was added dropwise and the mixture was stirred in the cold for 1 hour. The mixture was then diluted with additional dichloromethane, washed with water and brine, dried over anhydrous sodium sulfate, and concentrated to give the crude mixed anhydride.

To a solution of the mixed anhydride intermediate in acetone (4 mL) was added a solution of sodium azide (0.25 g, 3.85 mmol) in water (4 mL). The mixture was stirred for 10 minutes and then diluted with dichloromethane and water. The organic phase was washed with brine, dried over magnesium sulfate, and concentrated to give (S)-3-(tert-butyl-diphenyl-silanyloxy)-2-methylpropionyl azide.

The azide was dissolved in toluene (2 mL) and heated in an oil bath at 120° C. Vigorous nitrogen gas evolution quickly resulted yielding the desired (S)-tert-butyl-2-isocyanato-propoxy-diphenylsilane by the Curtius rearrangement.

Example 15c (S)-1-[2-(tert-Butyl-diphenyl-silanyloxy)-1-methyl-ethyl]-7-chloro-3-(4-methoxy-phenyl)-3,4-dihydro-1H-pyrimido[4,5-d]pyrimidin-2-one

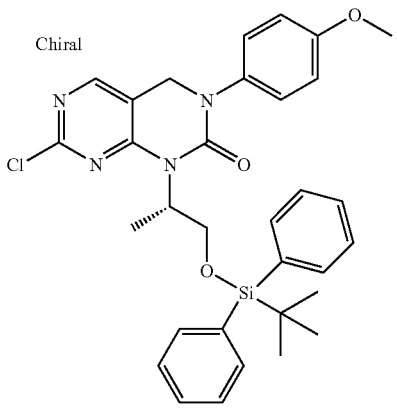

(S)-tert-Butyl-2-isocyanato-propoxy-diphenylsilane (generated in situ from 0.55 g, 1.61 mmol of (S)-3-(tert-butyl-diphenyl-silanyloxy)-2-methylpropionic acid) (from Example 15b supra) in hot toluene (2.5 mL) at 120° C. was treated with [(2,4-dichloropyrimidin-5-yl)methyl](4-methoxy-phenyl)amine (0.41 g, 1.45 mmol) (from Example 1d supra). The solution was heated at 120° C. for 35 minutes and then cooled to room temperature and concentrated to give an intermediate urea.

This intermediate urea was dissolved in anhydrous tetrahydrofuran (5 mL) and cooled in an ice-water bath. Potassium tert-butoxide (1.0 M in tetrahydrofuran, 1.5 mL, 1.50 mmol) was added dropwise and stirring continued in the cold for 15 minutes. The mixture was filtered through a bed of silica gel and eluted with ethyl acetate. Further purification by flash chromatography (Biotage 40 M, 25:75 ethyl acetate-hexanes) gave (S)-1-[2-(tert-butyl-diphenyl-silanyloxy)-1-methyl-ethyl]-7-chloro-3-(4-methoxy-phenyl)-4-methyl-3,4-dihydro-1H-pyrimido[4,5-d]pyrimidin-2-one along with the uncyclized intermediate, (S)-3-[2-tert-butyl-diphenyl-silanyloxy-1-methyl-ethyl]-1-(2,4-dichloropyrimidin-5-yl-methyl)-1-(4-methoxyphenyl)-urea, in ~2:1 ratio of the product to intermediate urea.

This mixture (0.66 g) was dissolved in anhydrous tetrahydrofuran (5 mL) and cooled in an ice-water bath. To this solution was added potassium tert-butoxide (1.0 M in tetrahydrofuran, 1.0 mL, 1.00 mmol). The mixture was stirred in the cold for 15 minutes and then the bath was removed and stirring continued for another 5 minutes. The mixture was filtered through a bed of silica gel and eluted with ethyl acetate. Purification by flash chromatography (Biotage 40 M, 40:60 ethyl acetate-hexanes) gave (S)-1-[2-(tert-butyl-diphenyl-silanyloxy)-1-methyl-ethyl]-7-chloro-3-(4-methoxy-phenyl)-3,4-dihydro-1H-pyrimido[4,5-d]pyrimidin-2-one. (Yield 0.38 g, 40.2%).

Example 15d (S)-(+)-1-(2-Hydroxy-1-methyl-ethyl)-3-(4-methoxy-phenyl)-7-phenylamino-3,4-dihydro-1H-pyrimido[4,5-d]pyrimidin-2-one

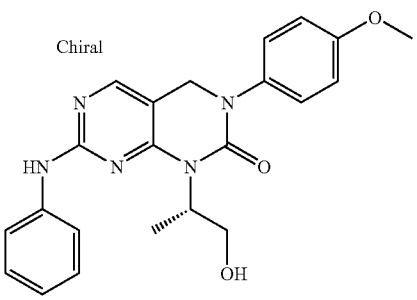

(S)-1-[2-(tert-Butyl-diphenyl-silanyloxy)-1-methyl-ethyl]-7-chloro-3-(4-methoxy-phenyl)-3,4-dihydro-1H-pyrimido[4,5-d]pyrimidin-2-one (0.50 g, 0.85 mmol) (from Example 15c supra) was combined with aniline (0.50 mL, 5.49 mmol) (Aldrich) and heated in an oil bath at 85° C. for 3 hours. The mixture was cooled to room temperature, diluted with ethyl acetate and washed with water and brine. The organic phase was dried over anhydrous sodium sulfate and concentrated. Purification by flash chromatography (Biotage 40S, ethyl acetate-hexanes gradient [20–40% ethyl acetate]) gave (S)-1-(2-tert-butyl-diphenyl-silanyloxy-1-methyl-ethyl)-3-(4-methoxy-phenyl)-7-phenylamino-3,4-dihydro-1H-pyrimido[4,5-d]pyrimidin-2-one. (Yield 0.44 g, 76.1%).

The silyl-protected product (0.43 g, 0.67 mmol) was dissolved in anhydrous tetrahydrofuran (5 mL) and treated with tetrabutylammonium fluoride (1.0 M in tetrahydrofuran, 2.70 mL, 2.70 mmol) (Aldrich) at room temperature for 5 hours. The reaction was then concentrated. The residue was redissolved in ethyl acetate and washed with water and brine. The organic phase was dried over anhydrous sodium sulfate and concentrated. Purification by flash chromatography (Biotage 40S, ethyl acetate-hexanes gradient [75–90% ethyl acetate]) followed by crystallization from ethyl acetate-hexanes gave (S)-(+)-1-(2-hydroxy-1-methyl-ethyl)-3-(4-methoxy-phenyl)-7-phenylamino-3,4-dihydro-1H-pyrimido[4,5-d]pyrimidin-2-one. (Yield 0.209 g, 77.2%). Melting Point: 140–147° C.

HR-MS (ES$^+$) m/z Calculated for $C_{22}H_{23}N_5O_3$ [M+H]$^+$: 406.1874. Found: 406.1878.

Example 16

(S)-(+)-7-(4-Fluoro-phenylamino)-1-(2-hydroxy-1-methyl-ethyl)-3-(4-methoxy-phenyl)-3,4-dihydro-1H-pyrimido[4,5-d]pyrimidin-2-one

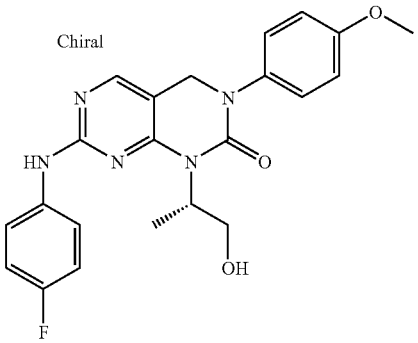

(S)-1-[2-(tert-Butyl-diphenyl-silanyloxy)-1-methyl-ethyl]-7-chloro-3-(4-methoxy-phenyl)-3,4-dihydro-1H-pyrimido[4,5-d]pyrimidin-2-one (0.38 g, 0.64 mmol) (from Example 15c supra) was combined with 4-fluoroaniline (0.30 mL, 3.20 mmol) (Aldrich) and heated in an oil bath at 95° C. for 4.5 hours. The mixture was cooled to room temperature and triturated with hexanes. The oily residue was dissolved in ethyl acetate and washed with water and brine. The organic phase was dried over anhydrous sodium sulfate and concentrated. Purification by flash chromatography (Biotage 40M, ethyl acetate-hexanes gradient [35–45% ethyl acetate]) gave (S)-7-(4-fluoro-phenylamino)-1-(2-tert-butyl-diphenyl-silanyloxy-1-methyl-ethyl)-3-(4-methoxy-phenyl)-3,4-dihydro-1H-pyrimido[4,5-d]pyrimidin-2-one. (Yield 0.306 g, 72.3%).

(S)-7-(4-Fluoro-phenylamino)-1-(2-tert-butyl-diphenyl-silanyloxy-1-methyl-ethyl)-3-(4-methoxy-phenyl)-3,4-dihydro-1H-pyrimido[4,5-d]pyrimidin-2-one (0.30 g, 0.45 mmol) was dissolved in anhydrous tetrahydrofuran (3.5 mL) and treated with tetrabutylammonium fluoride (1.0 M in tetrahydrofuran, 1.80 mL, 1.80 mmol) (Aldrich) at room temperature for 6 hours. The reaction was then concentrated. The residue was redissolved in ethyl acetate and washed with water and brine. The organic phase was dried over anhydrous sodium sulfate and concentrated. Purification by flash chromatography (Biotage 40S, ethyl acetate-hexanes gradient [60–100% ethyl acetate]) followed by crystallization from ethyl acetate-hexanes gave (S)-(+)-1-(2-hydroxy-1-methyl-ethyl)-3-(2-fluoro-4-methoxy-phenyl)-7-phenylamino-3,4-dihydro-1H-pyrimido[4,5-d]pyrimidin-2-one. (Yield 0.13 g, 66.2%). Melting Point: 188–198° C.

HR-MS (ES+) m/z Calculated for $C_{22}H_{22}FN_5O$ [M+H]+: 424.1780. Found: 424.1783.

[(2,4-Dichloropyrimidin-5-yl)methyl]-(4-methoxyphenyl)-amine
Example 17a

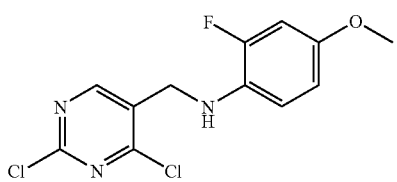

A mixture of 2,4-dichloro-5-chloromethyl-pyrimidine (3.70 g, 18.7 mmol) (from Example 1b supra), 2-fluoro-4-methoxy-phenylamine (2.40 g, 17.0 mmol) (from Example 14a supra) and potassium carbonate (4.70 g, 34.0 mmol) in acetone (100 mL) was stirred at room temperature for 18 hours. The precipitate was filtered off and the solution was concentrated under reduced pressure. The residue was diluted with ethyl acetate and washed with water and brine, dried over magnesium sulfate, filtered and concentrated under reduced pressure. This residue was purified by flash chromatography eluting with ethyl acetate-hexanes (1:4) to give [(2,4-dichloropyrimidin-5-yl)methyl]-(4-methoxyphenyl)-amine. (Yield 3.99 g, 78%).

Example 17b tert-Butyl-(trans-4-isocyanato-cyclohexyloxy)-dimethyl-silane

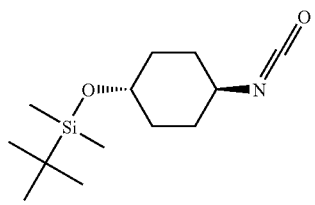

To a solution of trans-4-(tert-butyl-dimethyl-silanyloxy)-cyclohexylamine (1.0 g, 4.36 mmol) (from Example 3a supra) and triethylamine (3.04 mL, 21.8 mmol) (Burdick & Jackson) in dichloromethane (30 mL) at 0° C. was added phosgene (~20% in toluene, 6.4 mL, 13.1 mmol) (Fluka) in one portion. The reaction mixture was stirred at 0° C. for 40 minutes, followed by addition of 0.5N aqueous hydrochloric acid (50 mL). The organic phase was washed with brine, dried over magnesium sulfate, filtered and concentrated under reduced pressure. The residue was purified by flash chromatography eluting with ethyl acetate-hexanes (1:9) to give tert-butyl-(trans-4-isocyanato-cyclohexyloxy)-dimethyl-silane. (Yield 0.90 g, 81%).

Example 17c

1-[trans-4-(tert-Butyl-dimethyl-silanyloxy)-cyclohexyl]-7-chloro-3-(2-fluoro-4-methoxy-phenyl)-3,4-dihydro-1H-pyrimido[4,5-d]pyrimidin-2-one

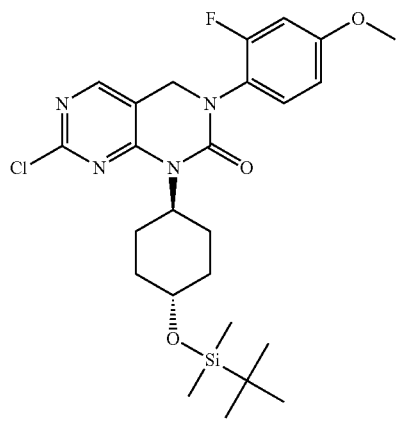

To a solution of (2,4-dichloro-pyrimidin-5-yl-methyl)-(2-fluoro-4-methoxy-phenyl)amine (1.1 g, 3.64 mmol) (from Example 17a supra) in tetrahydrofuran (50 mL) at −78° C.

was added n-butyllithium (2.5 M in hexanes, 1.75 mL, 4.37 mmol) (Aldrich). After stirring at −78° C. for 40 minutes, tert-butyl-(trans-4-isocyanato-cyclohexyloxy)-dimethyl-silane (1.12 g, 4.37 mmol) (from Example 17b supra) was added. The mixture was stirred at −70° C. for 1 hour and then at room temperature for 3 hours. It was diluted with ethyl acetate, washed with brine, dried over magnesium sulfate, filtered and concentrated under reduced pressure. The residue was purified by flash chromatography eluting with ethyl acetate-hexanes (3:7 then 2:3) to give 1-[trans-4-(tert-butyl-dimethyl-silanyloxy)-cyclohexyl]-7-chloro-3-(2-fluoro-4-methoxy-phenyl)-3,4-dihydro-1H-pyrimido[4,5-d]pyrimidin-2-one. (Yield 0.60 g, 33%).

Example 17d 3-(2-Fluoro-4-methoxy-phenyl)-1-(trans-4-hydroxy-cyclohexyl)-7-(4-methoxy-phenylamino)-3,4-dihydro-1H-pyrimido[4,5-d]pyrimidin-2-one

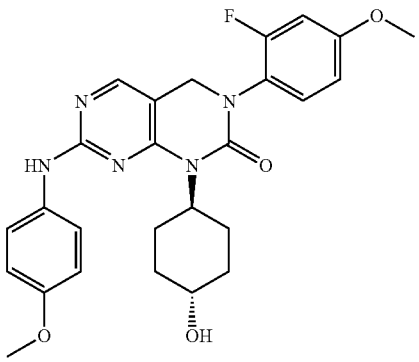

A mixture of 1-[trans-4-(tert-butyl-dimethyl-silanyloxy)-cyclohexyl]-7-chloro-3-(2-fluoro-4-methoxy-phenyl)-3,4-dihydro-1H-pyrimido[4,5-d]pyrimidin-2-one (0.20 g, 0.38 mmol) (from Example 17c supra), p-anisidine (61.5 mg, 0.50 mmol) (Aldrich) and p-toluenesulfonic acid monohydrate (95.1 mg, 0.50 mmol) (Aldrich) in 2-propanol (4 mL) was placed in a microwave reactor (SmithSynthesizer™). The reaction mixture was heated at 160° C. for 15 minutes. After cooling, it was concentrated under reduced pressure and purified by RP-HPLC (C-18, eluted with acetonitrile-water) to give 3-(2-fluoro-4-methoxy-phenyl)-1-(trans-4-hydroxy-cyclohexyl)-7-(4-methoxy-phenylamino)-3,4-dihydro-1H-pyrimido[4,5-d]pyrimidin-2-one. (Yield 0.12 g, 61%).

HRMS m/z Calculated for $C_{26}H_{28}FN_5O_4$ [(M+H)$^+$]: 494.2198. Found: 494.2206.

Example 18

3-(2-Fluoro-4-methoxy-phenyl)-1-(trans-4-hydroxy-cyclohexyl)-7-(3,4-dimethoxy-phenylamino)-3,4-dihydro-1H-pyrimido[4,5-d]pyrimidin-2-one

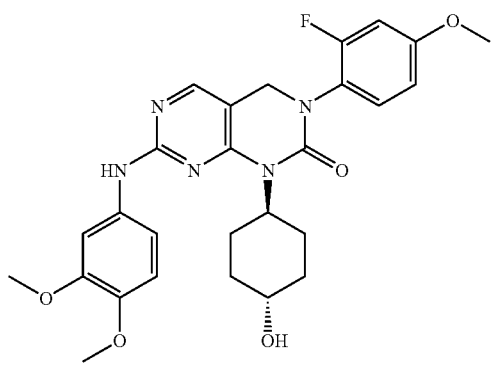

A mixture of 1-[trans-4-(tert-butyl-dimethyl-silanyloxy)-cyclohexyl]-7-chloro-3-(2-fluoro-4-methoxy-phenyl)-3,4-dihydro-1H-pyrimido[4,5-d]pyrimidin-2-one (0.20 g, 0.38 mmol) (from Example 17c supra), 4-amino-veratrole (76.6 mg, 0.50 mmol) (Aldrich) and p-toluenesulfonic acid monohydrate (95.1 mg, 0.50 mmol) (Aldrich) in 2-propanol (4 mL) was placed in a microwave reactor (SmithSynthesizer™). The reaction mixture was heated at 160° C. for 15 minutes. After cooling, it was concentrated under reduced pressure and purified by RP-HPLC (C-18, eluted with acetonitrile-water) to give 3-(2-fluoro-4-methoxy-phenyl)-1-(trans-4-hydroxy-cyclohexyl)-7-(3,4-dimethoxy-phenylamino)-3,4-dihydro-1H-pyrimido[4,5-d]pyrimidin-2-one. (Yield 0.13 g, 63%).

HRMS m/z Calculated for $C_{27}H_{30}FN_5O_5$ [(M+H)$^+$]: 524.2304. Found: 524.2311.

Example 19a

1-[trans-4-(tert-Butyl-dimethyl-silanyloxy)-cyclohexyl]-7-chloro-3-(4-methoxy-phenyl)-3,4-dihydro-1H-pyrimido[4,5-d]pyrimidin-2-one

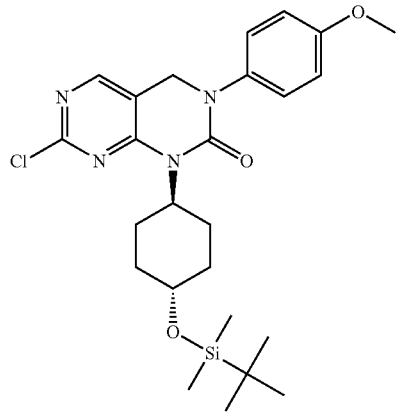

To a solution of [(2,4-dichloropyrimidin-5-yl)methyl](4-methoxy-phenyl)amine (1.0 g, 3.52 mmol) (from Example 1d supra) in tetrahydrofuran (50 mL) at −78° C. was added n-butyllithium (2.5 M in hexanes, 1.7 mL, 4.22 mmol) (Aldrich). After stirring at −78° C. for 20 minutes, tert-butyl-(trans-4-isocyanato-cyclohexyloxy)-dimethyl-silane (1.1 g, 4.22 mmol) (from Example 17b supra) was added. The mixture was stirred at −70° C. for 1 hour and then at room temperature for 3 hours. The reaction mixture was diluted with ethyl acetate, washed with brine, dried over magnesium sulfate, filtered and concentrated under reduced pressure. The residue was purified by flash chromatography eluting with ethyl acetate-hexanes (3:7 then 2:3) to give 1-[trans-4-(tert-butyl-dimethyl-silanyloxy)-cyclohexyl]-7-chloro-3-(4-methoxy-phenyl)-3,4-dihydro-1H-pyrimido[4,5-d]pyrimidin-2-one. (Yield 0.61 g, 34%).

Example 19b

1-[trans-4-(tert-Butyl-dimethyl-silanyloxy)-cyclohexyl]-3-(4-methoxy-phenyl)-7-(3,4-dimethoxy-phenylamino)-3,4-dihydro-1H-pyrimido[4,5-d]pyrimidin-2-one

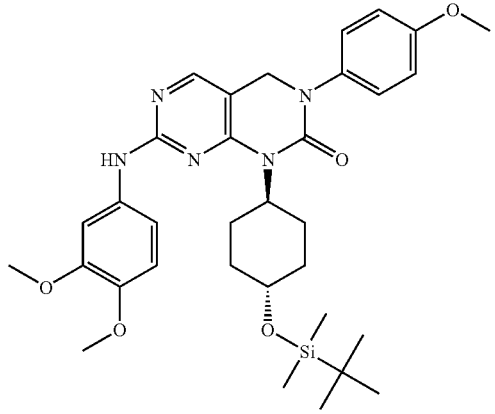

A mixture of 1-[trans-4-(tert-butyl-dimethyl-silanyloxy)-cyclohexyl]-7-chloro-3-(4-methoxy-phenyl)-3,4-dihydro-1H-pyrimido[4,5-d]pyrimidin-2-one (0.20 g, 0.40 mmol) (from Example 19a supra) and 4-amino-veratrole (80.0 mg, 0.52 mmol) (Aldrich) in 2-propanol (4 mL) was placed in a microwave reactor (SmithSynthesizer™). The reaction mixture was heated at 160° C. for 10 minutes. After cooling, it was concentrated under reduced pressure. The residue was purified by flash chromatography eluting with ethyl acetate-hexanes (3:7 then 2:3) to give 1-[trans-4-(tert-butyl-dimethyl-silanyloxy)-cyclohexyl]-3-(4-methoxy-phenyl)-7-(3,4-dimethoxy-phenylamino)-3,4-dihydro-1H-pyrimido[4,5-d]pyrimidin-2-one. (Yield 0.09 g, 36%).

Example 19c 3-(4-Methoxy-phenyl)-1-(trans-4-hydroxy-cyclohexyl)-7-(3,4-dimethoxy-phenylamino)-3,4-dihydro-1H-pyrimido[4,5-d]pyrimidin-2-one

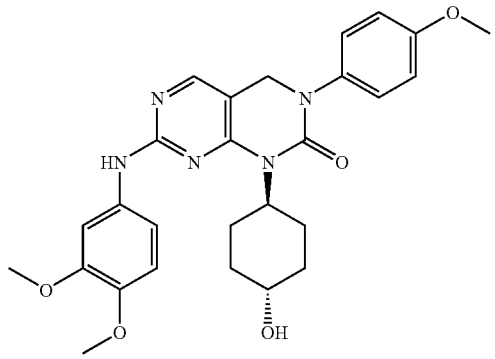

To a solution of 1-[trans-4-(tert-butyl-dimethyl-silanyloxy)-cyclohexyl]-3-(4-methoxy-phenyl)-7-(3,4-dimethoxy-phenylamino)-3,4-dihydro-1H-pyrimido[4,5-d]pyrimidin-2-one (90 mg, 0.24 mmol) (from Example 19b supra) in dichloromethane (5 mL) was added trifluoroacetic acid (2.0 mL) (Aldrich) at 0° C. The mixture was stirred at 0° C. for 2 hours. The reaction mixture was diluted with ethyl acetate (15 mL) and washed with saturated aqueous sodium bicarbonate solution and brine, dried over magnesium sulfate, filtered and concentrated under reduced pressure. The residue was purified by flash chromatography eluting with ethyl acetate to give crude product which was recrystallized from ethyl acetate-hexanes to give 3-(4-methoxy-phenyl)-1-(trans-4-hydroxy-cyclohexyl)-7-(3,4-dimethoxy-phenylamino)-3,4-dihydro-1H-pyrimido[4,5-d]pyrimidin-2-one. (Yield 41 mg, 59%).

HRMS m/z Calculated for $C_{27}H_{31}N_5O_5$ $[(M+H)^+]$: 506.2398. Found: 506.2404.

Example 20a

1-[trans-4-(tert-Butyl-dimethyl-silanloxy)-cyclohexyl]-3-(4-methoxy-phenyl)-7-(4-methoxy-phenylamino)-3,4-dihydro-1H-pyrimido[4,5-d]pyrimidin-2-one

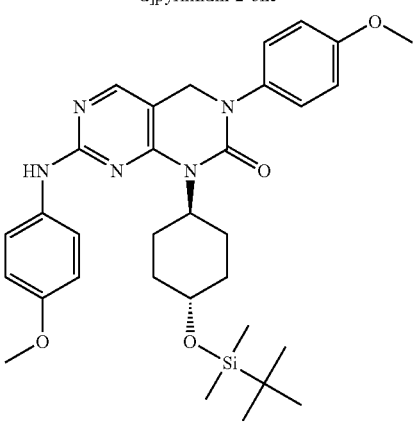

A mixture of 1-[trans-4-(tert-butyl-dimethyl-silanyloxy)-cyclohexyl]-7-chloro-3-(4-methoxy-phenyl)-3,4-dihydro-1H-pyrimido[4,5-d]pyrimidin-2-one (0.20 g, 0.40 mmol) (from Example 19a supra) and p-anisidine (63.6 mg, 0.52 mmol) (Aldrich) in 2-propanol (4 mL) was placed in a microwave reactor (SmithSynthesizer™). The reaction mixture was heated at 160° C. for 10 minutes. After cooling, it was concentrated under reduced pressure. The residue was purified by flash chromatography eluting with ethyl acetate-hexanes (3:7 then 2:3) to give 1-[trans-4-(tert-butyl-dimethyl-silanyloxy)-cyclohexyl]-3-(4-methoxy-phenyl)-7-(4-methoxy-phenylamino)-3,4-dihydro-1H-pyrimido[4,5-d]pyrimidin-2-one. (Yield 0.14 g, 58%).

Example 20b 3-(4-Methoxy-phenyl)-1-(trans-4-hydroxy-cyclohexyl)-7-(4-methoxy-phenylamino)-3,4-dihydro-1H-pyrimido[4,5-d]pyrimidin-2-one

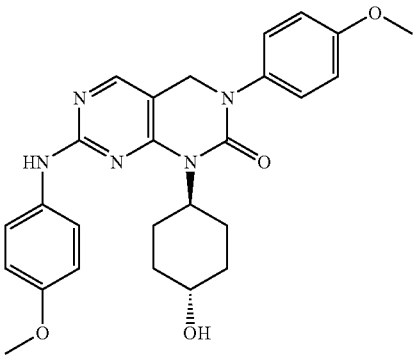

To a solution of 1-[trans-4-(tert-butyl-dimethyl-silanyloxy)-cyclohexyl]-3-(4-methoxy-phenyl)-7-(4-methoxy-phenylamino)-3,4-dihydro-1H-pyrimido[4,5-d]pyrimidin-2-one (0.14 g, 0.15 mmol) (from Example 20a supra) in dichloromethane (5 mL) was added trifluoroacetic acid (2.5 mL) at 0° C. The mixture was stirred at 0° C. for 2 hours. The reaction mixture was diluted with ethyl acetate (15 mL) and washed with saturated aqueous sodium bicarbonate solution and brine, dried over magnesium sulfate, filtered and concentrated under reduced pressure. The residue was purified by flash chromatography eluting with ethyl acetate to give crude product which was recrystallized from ethyl acetate-hexanes to give 3-(4-methoxy-phenyl)-1-(trans-4-hydroxy-cyclohexyl)-7-(4-methoxy-phenylamino)-3,4-dihydro-1H-pyrimido[4,5-d]pyrimidin-2-one. (Yield 61 mg, 55%).

HRMS m/z Calculated for $C_{26}H_{29}N_5O_4$ [(M+H)$^+$]: 476.2293. Found: 476.2299.

Example 21a (S)-1-[2-(tert-Butyl-diphenyl-silanyloxy)-1-methyl-ethyl]-7-chloro-3-(2-fluoro-4-methoxy-phenyl)-3,4-dihydro-1H-pyrimido[4,5-d]pyrimidin-2-one

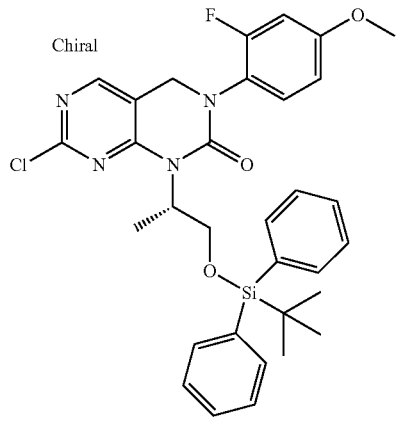

(S)-tert-Butyl-2-isocyanato-propoxy-diphenylsilane [generated in situ from 1.05 g, 3.07 mmol of (S)-3-(tert-butyl-diphenyl-silanyloxy)-2-methylpropionic acid) (from Example 15b supra)] in hot toluene (5 mL) at 120° C. was treated with (2,4-dichloro-pyrimidin-5-ylmethyl)-(2-fluoro-4-methoxy-phenyl)-amine (0.84 g, 2.77 mmol) (from Example 17a supra). The solution was heated at 120° C. for 40 minutes and then cooled to room temperature and concentrated to give crude (S)-3-[2-tert-butyl-diphenyl-silanyloxy-1-methyl-ethyl]-1-(2,4-dichloropyrimidin-5-yl-methyl)-1-(2-fluoro-4-methoxyphenyl)-urea. This urea was dissolved in anhydrous tetrahydrofuran (10 mL) and cooled in an ice-water bath. Potassium tert-butoxide (1.0 M in tetrahydrofuran, 3.2 mL, 3.20 mmol) (Aldrich) was added dropwise. The mixture was stirred in the cold for 15 minutes and then the bath was removed and stirring continued for another 5 minutes. The mixture was filtered through a bed of silica gel and eluted with ethyl acetate. The NMR of the crude product showed ~2:1 ratio of product to the uncyclized intermediate (S)-3-[2-tert-butyl-diphenyl-silanyloxy-1-methyl-ethyl]-1-(2,4-dichloropyrimidin-5-yl-methyl)-1-(2-fluoro-4-methoxyphenyl)-urea.

The crude mixture was redissolved in anhydrous tetrahydrofuran (10 mL) and cooled in an ice-water bath. Potassium tert-butoxide (1.0 M in tetrahydrofuran, 1.5 mL, 1.50 mmol) (Aldrich) was added and mixture stirred in the cold for 15 minutes. The cooling bath was removed and stirring continued for an additional 5 minutes. The mixture was filtered through a bed of silica gel and eluted with ethyl acetate. Purification by flash chromatography (Biotage 40S, ethyl acetate-hexanes gradient [25–38% ethyl acetate]) gave (S)-1-[2-(tert-butyl-diphenyl-silanyloxy)-1-methyl-ethyl]-7-chloro-3-(2-fluoro-4-methoxy-phenyl)-3,4-dihydro-1H-pyrimido[4,5-d]pyrimidin-2-one. (Yield 0.53 g, 31.7%).

A portion of (S)-1-[2-(tert-butyl-diphenyl-silanyloxy)-1-methyl-ethyl]-7-chloro-3-(2-fluoro-4-methoxy-phenyl)-3,4-dihydro-1H-pyrimido[4,5-d]pyrimidin-2-one still contained about 20% of the intermediate urea. This material was cycled through another treatment with potassium tert-butoxide (1.0 M in tetrahydrofuran, 0.65 mL, 0.65 mmol) to give (S)-1-[2-(tert-butyl-diphenyl-silanyloxy)-1-methyl-ethyl]-7-chloro-3-(2-fluoro-4-methoxy-phenyl)-3,4-dihydro-1H-pyrimido[4,5-d]pyrimidin-2-one. (Yield 0.19 g, 11.2%).

Example 21b (S)-(+)-3-(2-Fluoro-4-methoxy-phenyl)-7-(4-fluoro-phenylamino)-1-(2-hydroxy-1-methyl-ethyl)-3,4-dihydro-1H-pyrimido[4,5-d]pyrimidin-2-one

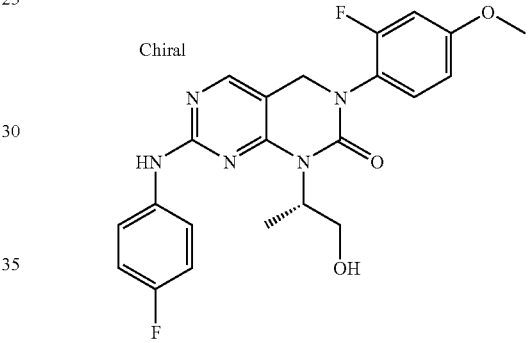

(S)-1-[2-(tert-Butyl-diphenyl-silanyloxy)-1-methyl-ethyl]-7-chloro-3-(2-fluoro-4-methoxy-phenyl)-3,4-dihydro-1H-pyrimido[4,5-d]pyrimidin-2-one (0.40 g, 0.66 mmol) (from Example 21a supra) was combined with 4-fluoroaniline (0.50 mL, 5.28 mmol) (Aldrich) and heated in an oil bath at 105° C. for 2 hours. The mixture was cooled to room temperature and triturated with hexanes. The insoluble residue was then taken up in ethyl acetate and the aniline hydrochloride was filtered off. The filtrate was purified by flash chromatography (Biotage 40S, 30:70 ethyl acetate-hexanes). The impure fractions were recycled through another flash chromatography. This purified material was still contaminated with a small amount of the 4-fluoroaniline. This was removed by another trituration with hexanes to give (S)-3-(2-fluoro-4-methoxy-phenyl)-7-(4-fluoro-phenylamino)-1-(2-tert-butyl-diphenyl-silanyloxy-1-methyl-ethyl)-3,4-dihydro-1H-pyrimido[4,5-d]pyrimidin-2-one. (Yield 0.34 g, 71.8%).

(S)-3-(2-Fluoro-4-methoxy-phenyl)-7-(4-fluoro-phenylamino)-1-(2-tert-butyl-diphenyl-silanyloxy-1-methyl-ethyl)-3,4-dihydro-1H-pyrimido[4,5-d]pyrimidin-2-one (0.33 g, 0.46 mmol) was dissolved in anhydrous tetrahydrofuran (3.5 mL) and treated with tetrabutylammonium fluoride (1.0 M in tetrahydrofuran, 1.90 mL, 1.90 mmol) (Aldrich). The reaction was stirred in a water bath that was maintained in the 25–35° C. range. The reaction was complete after 4 hours and was concentrated. The residue was redissolved in ethyl acetate and washed with water and brine. The organic phase was dried over anhydrous sodium sulfate and concentrated. Purification by flash chromatography (Biotage 40S, 75:25 ethyl acetate-hexanes) followed by crystallization from ethyl acetate-hexanes gave (S)-(+)-3-(2-fluoro-4-methoxy-phenyl)-7-(4-fluoro-phenylamino)-1-(2-hydroxy-1-methyl-ethyl)-3,4-dihydro-1H-pyrimido[4,5-d]pyrimidin-2-one as a white solid. (Yield 0.18 g, 83.5%). Melting Point: 173–177° C.

HR-MS (ES$^+$) m/z Calculated for $C_{22}H_{21}F_2N_5O_3$ [M+H]$^+$: 442.1685. Found: 442.1691.

Example 22

(S)-(+)-3-(2-Fluoro-4-methoxy-phenyl)-1-(2-hydroxy-1-methyl-ethyl)-7-(4-methoxy-phenylamino)-3,4-dihydro-1H-pyrimido[4,5-d]pyrimidin-2-one

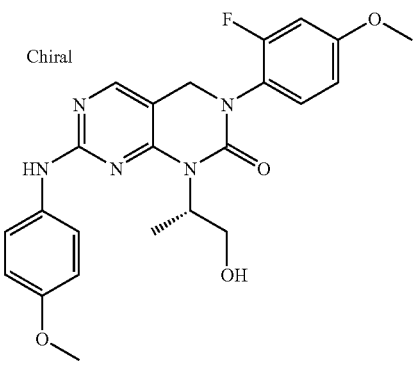

(S)-1-[2-(tert-Butyl-diphenyl-silanyloxy)-1-methyl-ethyl]-7-chloro-3-(2-fluoro-4-methoxy-phenyl)-3,4-dihydro-1H-pyrimido[4,5-d]pyrimidin-2-one (0.30 g, 0.50 mmol) (from Example 21a supra) was dissolved in toluene (0.5 mL) and treated with p-anisidine (0.15 g, 1.19 mmol) in an oil bath at 105° C. After two hours, a significant amount of starting material was still present. Additional p-anisidine (0.11 g, 0.92 mmol) was added and heating continued for another two hours. The mixture was then cooled to room temperature and triturated with hexanes to remove excess p-anisidine. The insoluble residue was purified by flash chromatography (Biotage 40M, ethyl acetate-hexanes gradient [25–40% ethyl acetate]). This purified material was still contaminated with a small amount of p-anisidine. This was removed by another trituration with hexanes to give (S)-3-(2-fluoro-4-methoxy-phenyl)-1-(2-tert-butyl-diphenyl-silanyloxy-1-methyl-ethyl)-7-(4-methoxy-phenylamino)-3,4-dihydro-1H-pyrimido[4,5-d]pyrimidin-2-one. (Yield 0.26 g, 72.2%).

(S)-3-(2-Fluoro-4-methoxy-phenyl)-1-(2-tert-butyl-diphenyl-silanyloxy-1-methyl-ethyl)-7-(4-methoxy-phenylamino)-3,4-dihydro-1H-pyrimido[4,5-d]pyrimidin-2-one (0.25 g, 0.35 mmol) was dissolved in anhydrous tetrahydrofuran (2.5 mL) and treated with tetrabutylammonium fluoride (1.0 M in tetrahydrofuran, 1.40 mL, 1.400 mmol). The reaction was stirred in a water bath that was maintained in the 30–40° C. range. The reaction was complete after 4 hours and was concentrated. This residue was redissolved in ethyl acetate and washed with water and brine. The organic phase was dried over anhydrous sodium sulfate, concentrated and then purified by flash chromatography (Biotage 40S, 75:25 ethyl acetate-hexanes) to give (S)-(+)-3-(2-fluoro-4-methoxy-phenyl)-1-(2-hydroxy-1-methyl-ethyl)-7-(4-methoxy-phenylamino)-3,4-dihydro-1H-pyrimido[4,5-d]pyrimidin-2-one as a pale yellow foam. (Yield 0.14 g, 85.1%).

HR-MS (ES$^+$) m/z Calculated for $C_{23}H_{24}FN_5O_4$ [M+H]$^+$: 454.1885. Found: 454.1890.

Example 23a (R)-3-(tert-Butyl-diphenyl-silanyloxy)-2-methylpropionic acid

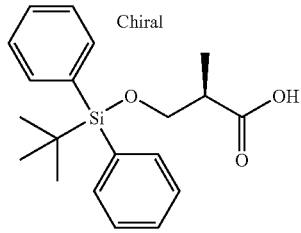

Methyl (R)-(−)-3-hydroxy-2-methylpropionate (0.82 g, 6.92 mmol) (Aldrich) was dissolved in dichloromethane (8 mL, dried over molecular sieves). Imidazole (0.67 g, 9.68 mmol) (Aldrich) was added. When all had dissolved, tert-butyldiphenysilyl chloride (1.80 mL, 6.92 mmol) (Aldrich) was added and the mixture was stirred at ambient temperature for 3 hours. The reaction was diluted with additional dichloromethane, washed with water and brine, dried over anhydrous sodium sulfate and concentrated to give methyl (R)-3-(tert-butyl-diphenyl-silanyloxy)-2-methyl-propionate as an oil. (Yield 2.42 g, 98%).

Methyl (R)-3-(tert-butyl-diphenyl-silanyloxy)-2-methylpropionate (2.42 g, 7.05 mmol) was dissolved in 3:1 tetrahydrofuran-methanol (24 mL) and saponified with aqueous sodium hydroxide (1.0 N, 7.9 mL, 7.90 mmol) at 40° C. for 3 hours and then overnight at ambient temperature. The reaction mixture was concentrated. The residue was dissolved in ethyl acetate and then acidified with 1.0 N aqueous hydrochloric acid (~8 mL). The organic phase was washed with brine (3×), dried over anhydrous sodium sulfate and concentrated. Purification by flash chromatography (Biotage 40L, 20:80 ethyl acetate-hexanes) gave (R)-3-(tert-butyl-diphenyl-silanyloxy)-2-methylpropionic acid as an oil that solidified to a tacky white solid. (Yield 1.60 g, 67.6%).

Example 23b (R)-tert-Butyl-2-isocyanato-propoxydiphenylsilane

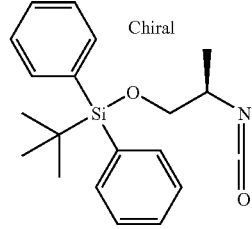

(R)-3-(tert-Butyl-diphenyl-silanyloxy)-2-methylpropionic acid (0.51 g, 1.48 mmol) (from Example 23a supra) was dissolved in dichloromethane (4 mL, dried over molecular sieves). Triethylamine (0.42 mL, 2.98 mmol) (Aldrich) was added and the solution was cooled in an ice-water bath. Ethyl chloroformate (0.17 mL, 1.78 mmol) (Aldrich) was added dropwise and the mixture was stirred in the cold for 50 minutes. The reaction mixture was diluted with additional dichloromethane and washed with water and then brine. The organic phase was dried over sodium sulfate and concentrated to give the mixed anhydride.

To a solution of this mixed anhydride in acetone (5 mL) was added a solution of sodium azide (0.29 g, 4.41 mmol) (Aldrich) in water (5 mL). The mixture was stirred at room temperature for 10 minutes and then diluted with additional dichloromethane and water. The organic phase was washed with brine, dried over magnesium sulfate and concentrated to give (R)-3-(tert-butyl-diphenyl-silanyloxy)-2-methylpropionyl azide.

(R)-3-(tert-Butyl-diphenyl-silanyloxy)-2-methylpropionyl azide was dissolved in toluene (~5 mL, dried over 4A molecular sieves) and heated in an oil bath at 120° C. Vigorous nitrogen gas evolution quickly resulted to give (R)-tert-butyl-2-isocyanato-propoxy-diphenylsilane by the Curtius rearrangement. This was used without further purification.

Example 23c (R)-1-[2-(tert-Butyl-diphenyl-silanyloxy)-1-methyl-ethyl]-7-chloro-3-(4-methoxy-phenyl)-3,4-dihydro-1H-pyrimido[4,5-d]pyrimidin-2-one

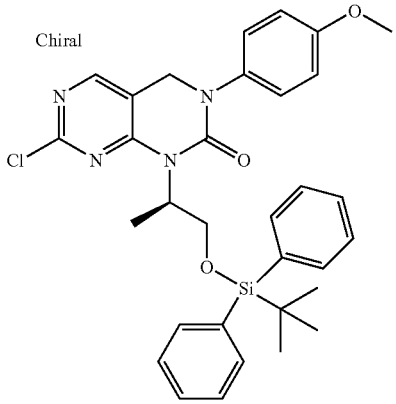

(R)-tert-Butyl-2-isocyanato-propoxy-diphenylsilane [generated in situ from 0.51 g, 1.48 mmol of (R)-3-(tert-butyl-diphenyl-silanyloxy)-2-methylpropionic acid)] in hot toluene (~5 mL) (from Example 23b supra) at 120° C. was treated with [(2,4-dichloropyrimidin-5-yl)methyl](4-methoxyphenyl)amine (0.38 g, 1.34 mmol) (from Example 1 d supra). The solution was heated at 120° C. for 45–50 minutes and then cooled to room temperature and concentrated to give the intermediate urea.

The crude urea intermediate was dissolved in anhydrous tetrahydrofuran (5 mL) and cooled in an ice-water bath. Potassium tert-butoxide (1.0 M in tetrahydrofuran, 1.4 mL, 1.4 mmol) (Aldrich) was added dropwise over about 5 minutes. The mixture was stirred in the cold for 15 minutes and then the bath was removed and stirring continued for an additional 3–4 minutes. The mixture was filtered through a silica gel plug and eluted with ethyl acetate. The crude product was purified by flash chromatography (Biotage 40M, ethyl acetate-hexanes gradient [30–40% ethyl acetate]) to give (R)-1-[2-(tert-butyl-diphenyl-silanyloxy)-1-methyl-ethyl]-7-chloro-3-(4-methoxy-phenyl)-3,4-dihydro-1H-pyrimido[4,5-d]pyrimidin-2-one as a foam. (Yield 0.57 g, 62.4%).

Example 23d (R)-(-)-1-(2-Hydroxy-1-methyl-ethyl)-3-(4-methoxy-phenyl)-7-phenylamino-3,4-dihydro-1H-pyrimido[4,5-d]pyrimidin-2-one

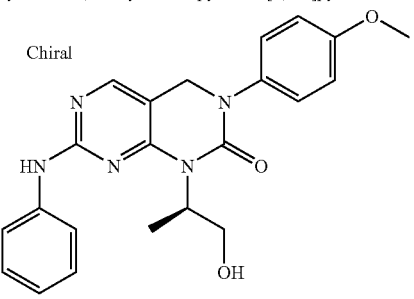

1-[2-(tert-Butyl-diphenyl-silanyloxy)-1-methyl-ethyl]-7-chloro-3-(4-methoxy-phenyl)-3,4-dihydro-1H-pyrimido[4,5-d]pyrimidin-2-one (0.56 g, 0.92 mmol) (from Example 23c supra) was combined with aniline (0.50 mL, 5.49 mmol) (Aldrich) and heated in an oil bath at 110° C. for 1.5 hours. The mixture was cooled to room temperature and triturated with hexanes. The residue was dissolved in ethyl acetate and filtered to remove the insoluble aniline hydrochloride. The filtrate was purified by flash chromatography (Biotage 40M, 40:60 ethyl acetate-hexanes). The product was still contaminated with a small amount of aniline. This was removed with another trituration with hexanes to give (R)-1-(2-tert-butyl-diphenyl-silanyloxy-1-methyl-ethyl)-3-(4-methoxy-phenyl)-7-phenylamino-3,4-dihydro-1H-pyrimido[4,5-d]pyrimidin-2-one. (Yield 0.55 g, 89.1%).

(R)-1-(2-tert-Butyl-diphenyl-silanyloxy-1-methyl-ethyl)-3-(4-methoxy-phenyl)-7-phenylamino-3,4-dihydro-1H-pyrimido[4,5-d]pyrimidin-2-one (0.55 g, 0.80 mmol) was dissolved in anhydrous tetrahydrofuran (6 mL) and treated with tetrabutylammonium fluoride (1.0 M in tetrahydrofuran, 3.2 mL, 3.20 mmol) (Aldrich) at 40° C. for 3 hours and then at room temperature for 2 hours. The reaction was concentrated. The residue was redissolved in ethyl acetate and washed with water and brine. The organic phase was dried over anhydrous sodium sulfate and concentrated. Purification by flash chromatography (Biotage 40M, ethyl acetate-hexanes gradient [75–85% ethyl acetate]) followed by crystallization from ethyl acetate-hexanes gave (R)-(-)-1-(2-hydroxy-1-methyl-ethyl)-3-(4-methoxy-phenyl)-7-phenylamino-3,4-dihydro-1H-pyrimido[4,5-d]pyrimidin-2-one as a white solid. (Yield 0.26 g, 79.9%). Melting Point: 156–163° C.

HR-MS (ES$^+$) m/z Calculated for $C_{22}H_{23}N_5O_3$ [M+H]$^+$: 406.1874. Found: 406.1878.

Example 24a 3-(4-Methoxy-phenyl)-7-phenylamino-3,4-dihydro-1H-pyrimido[4,5-d]pyrimidine-2-one

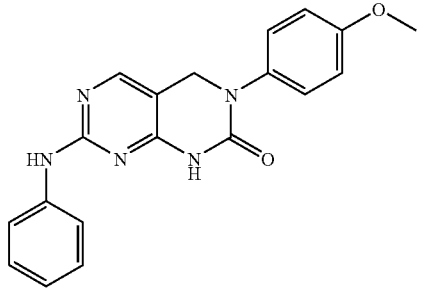

To a suspension of [(2,4-dichloropyrimidin-5-yl)methyl](4-methoxy-phenyl)amine (2.84 g, 10.0 mmol) (from Example 1d supra) in tert-butyl methyl ether (30 mL) was added benzoyl isocyanate (90%, 1.80 g, 11.0 mmol) (Aldrich) and the reaction mixture was heated at reflux overnight. The reaction mixture was concentrated under reduced pressure to give the crude urea derivative which was dissolved in dry tetrahydrofuran (20 mL) and the solution was cooled to 0° C. To this solution was added potassium tert-butoxide (1.0 M in tetrahydrofuran, 10 mL, 10.0 mmol) (Aldrich) and the reaction mixture was stirred at room temperature for 4 hours. The reaction mixture was then diluted with ethyl acetate (150 mL) and successively washed with saturated aqueous ammonium chloride solution (50 mL), water (30 mL) and brine(30 mL), dried over anhydrous sodium sulfate, filtered, and concentrated under reduced pressure. The residue was purified by flash column to give the mono-chloride as a white solid. (Yield 1.15 g, 29.1%, 2 steps).

A mixture of this mono chloride (0.40 g, 1.0 mmol) and aniline (0.28 g, 3.0 mmol) (Aldrich) was heated at 120° C. for 10 min. The reaction mixture was then diluted with ethyl acetate (50 mL) and water (30 mL). The suspension thus obtained was filtered and the solid was collected and washed with acetone, ethyl acetate and diethyl ether to give 3-(4-methoxy-phenyl)-7-phenylamino-3,4-dihydro-1H-pyrimido[4,5-d]pyrimidine-2-one as a white solid. (Yield 201 mg, 57.9%). The filtrate was concentrated partially under reduced pressure and filtered to give 1-benzoyl-3-(4-methoxy-phenyl)-7-phenylamino-3,4-dihydro-1H-pyrimido[4,5-d]pyrimidine-2-one as a white solid. (Yield 86.0 mg, 19.0%).

Example 24b 3-(4-Methoxy-phenyl)-1-methyl-7-phenylamino-3,4-dihydro-1H-pyrimido[4,5-d]pyrimidine-2-one

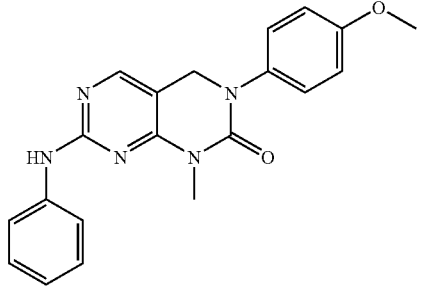

Method A:

To the suspension of 3-(4-methoxy-phenyl)-7-phenylamino-3,4-dihydro-1H-pyrimido[4,5-d]pyrimidin-2-one (34.7 mg, 0.1 mmol) (from Example 24a supra) in tetrahydrofuran (5 mL) was added sodium hydride (60%, 10 mg, 0.25 mmol) (Aldrich) followed by methyl iodide (0.032 mL, 0.5 mmol) (Aldrich) in one portion. The reaction mixture was stirred at room temperature overnight and then heated under reflux for 5 hours. The reaction was then quenched with saturated aqueous ammonium chloride solution and extracted with ethyl acetate (3×50 mL). The combined organic extracts were filtered to give 3-(4-methoxy-phenyl)-1-methyl-7-phenylamino-3,4-dihydro-1H-pyrimido[4,5-d]pyrimidine-2-one as a white solid. (Yield 20.9 mg, 57.9%).

Method B:

To a solution of [(2,4-dichloropyrimidin-5-yl)methyl](4-methoxy-phenyl)amine (198 mg, 0.7 mmol) (from Example 1d supra) in n-butanol (5 mL) was added methyl amine (20% solution in methanol, 0.7 mL, 1.4 mmol) (Aldrich) followed by N,N-diisopropyethylamine (130 mg) (Aldrich) in one portion. The reaction mixture was stirred at room temperature overnight, and then quenched with water and extracted with ethyl acetate (3×50 mL). The combined organic extracts were successively washed with water (10 mL) and brine (10 mL), dried over anhydrous sodium sulfate, filtered, and concentrated under reduced pressure to give the crude mono chloride as a colorless oil which was used in the next step without further purification.

To a solution of this crude mono chloride (195 mg, 0.7 mmol) in dichloromethane (20 mL) was added triethylamine (0.3 mL, 2.1 mmol) (Aldrich) followed by phosgene in toluene (20% solution, 0.5 mL, 0.98 mmol) (Fluka) dropwise. The reaction mixture was stirred at room temperature for 15 minutes. The reaction mixture was then poured into ice-cold water (50 mL) and extracted with ethyl acetate (3×50 mL). The combined organic extracts were successively washed with water (10 mL) and brine (10 mL), dried over anhydrous sodium sulfate, filtered, and concentrated under reduced pressure to give the crude intermediate which was dissolved again in dichloromethane (5 mL) and heated under reflux in the presence of 4-(dimethylamino)pyridine (20 mg) (Aldrich) overnight. The reaction mixture was quenched with water and extracted with ethyl acetate (3×50 mL). The combined organic extracts were successively washed with water (10 mL) and brine (10 mL), dried over anhydrous sodium sulfate, filtered, and concentrated under reduced pressure to give the crude product which was purified by preparative thin layer chromatography to give 7-chloro-3-(4-methoxy-phenyl)-1-methyl-3,4-dihydro-1H-pyrimido[4,5-d]pyrimidine-2-one. (Yield 79 mg, 37%, 3 steps).

The mixture of 7-chloro-3-(4-methoxy-phenyl)-1-methyl-3,4-dihydro-1H-pyrimido[4,5-d]pyrimidine-2-one (65 mg, 0.21 mmol) in aniline (1.0 mL) (Aldrich) was heated to 120° C. for 1 hour. After cooling, the reaction mixture was washed with hexanes (100 mL×4) and the crude product was re-crystallized from ethyl acetate-hexanes to give 3-(4-methoxy-phenyl)-1-methyl-7-phenylamino-3,4-dihydro-1H-pyrimido[4,5-d]pyrimidine-2-one as an off-white solid. (Yield 76.0 mg, 98.7%).

Example 25

1-(2-methoxy-ethoxymethyl)-3-(4-methoxy-phenyl)-7-phenylamino-3,4-dihydro-1H-pyrimido[4,5-d]pyrimidin-2-one

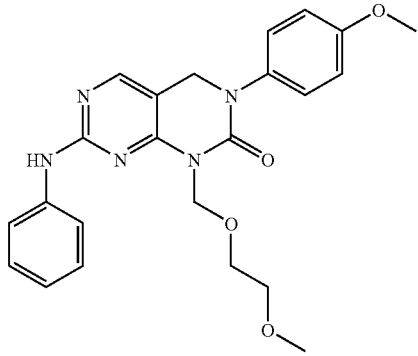

To the suspension of 3-(4-methoxy-phenyl)-7-phenylamino-3,4-dihydro-1H-pyrimido[4,5-d]pyrimidin-2-one (70 mg, 0.2 mmol) (from Example 24a supra) in tetrahydrofuran (10 mL) was added sodium hydride (60%, 20 mg, 0.5 mmol) (Aldrich) followed by 2-methoxyethoxymethyl chloride (0.032 mL, 2.4 mmol) (Aldrich) in one portion. The reaction mixture was heated at reflux for 5 hours to give a yellow solution. The reaction was then quenched with saturated aqueous ammonium chloride solution and extracted with ethyl acetate (3×50 mL). The combined organic extracts were filtered to give the starting material as a white solid (33.1 mg, 47.1%) and the filtrate was successively washed with water (10 mL) and brine (10 mL), dried over anhydrous sodium sulfate, filtered, and concentrated under reduced pressure to give the crude product which was purified by preparative thin layer chromatography to give 1-(2-methoxy-ethoxymethyl)-3-(4-methoxy-phenyl)-7-phenylamino-3,4-dihydro-1H-pyrimido[4,5-d]pyrimidin-2-one as a white amorphous solid. (Yield 30.5 mg, 35.0%).

Example 26

3-[-3-(4-Methoxy-phenyl)-2-oxo-7-phenylamino-3,4-dihydro-1H-pyrimido[4,5-d]pyrimidin-1-yl]-propionitrile

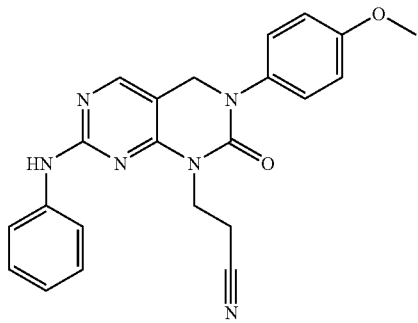

To the solution of [(2,4-dichloropyrimidin-5-yl)methyl](4-methoxyphenyl)amine (198 mg, 0.7 mmol) (from Example 1d supra) in n-butanol (5 mL) was added 3-aminopropionitrile (98 mg, 1.4 mmol) (Fluorochem Ltd.) followed by addition of N,N-diisopropylethylamine (0.13 mL) (Aldrich) in one portion. The reaction mixture was stirred at room temperature overnight, and then quenched with water and extracted with ethyl acetate (3×50 mL). The combined organic extracts were successively washed with water (10 mL) and brine (10 mL), dried over anhydrous sodium sulfate, filtered, and concentrated under reduced pressure to give the crude mono chloride as a colorless oil (Yield 220 mg) which was used in the next step without further purification.

To a solution of this crude mono chloride (212 mg) in dichloromethane (20 mL) at 0° C. was added triethylamine (0.29 mL, 2.1 mmol) (Aldrich) followed by phosgene in toluene (20% solution, 1.44 mL, 2.94 mmol) (Fluka) dropwise. The reaction mixture was stirred at 0° C. for 10 minutes and then at room temperature for 1.5 hours. The reaction mixture was then poured into ice-cold water (50 mL) and extracted with ethyl acetate (3×50 mL). The combined organic extracts were successively washed with water (10 mL) and brine (10 mL), dried over anhydrous sodium sulfate, filtered, and concentrated under reduced pressure to give a crude intermediate. This intermediate was dissolved in dichloromethane (5 mL) and heated under reflux in the presence of 4-(dimethylamino)pyridine (120 mg, 0.98 mmol) (Aldrich) for 1.5 hours. The reaction mixture was quenched with water and extracted with ethyl acetate (3×50 mL). The combined organic extracts were successively washed with water (10 mL) and brine (10 mL), dried over anhydrous sodium sulfate, filtered, and concentrated under reduced pressure to give the crude product which was purified by preparative thin layer chromatography to give 7-chloro-1-cyclopropylmethyl-3-(4-methoxyphenyl)-3,4-dihydro-1H-pyrimido[4,5-d]pyrimidine-2-one. (Yield 104 mg, 43.2%, 3 steps).

A mixture of 7-chloro-1-cyclopropylmethyl-3-(4-methoxy-phenyl)-3,4-dihydro-1H-pyrimido[4,5-d]pyrimidine-2-one (104 mg, 0.30 mmol) in aniline (2.0 mL) (Aldrich) was heated to 120° C. for 1.5 hours. After cooling, the reaction mixture was washed with hexanes (4×100 mL) and the crude product was purified by recrystallization from methanol-ethyl acetate to give 3-[-3-(4-methoxy-phenyl)-2-oxo-7-phenylamino-3,4-dihydro-1H-pyrimido[4,5-d]pyrimidin-1-yl]-propionitrile as a white solid. (Yield 111 mg, 91.7%).

Example 27a (-)-(1R,4S)-4-(tert-Butyl-dimethyl-silanyloxy)-cyclopent-2-enol

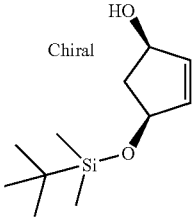

To a solution of (1R,3S)-(+)-4-cyclopentene-1,3-diol 1-acetate (1.0 g, 7.03 mmol) (Aldrich) and imidazole (960 mg, 14.06 mmol) (Aldrich) in tetrahydrofuran (35 mL) was added tert-butyldimethylsilyl chloride (1.27 g, 8.44 mmol) (Aldrich). The mixture was allowed to warm slowly to room temperature, stirred overnight and then partitioned between ethyl acetate and water. The organic layer was collected, dried over sodium sulfate, filtered and concentrated to a residue that was dissolved in methanol (45 mL). To this solution was added potassium carbonate (1.17 g, 8.44 mmol) and the mixture stirred overnight. The next morning the reaction mixture was partitioned between ethyl acetate and water. The organic layer was collected, dried over sodium sulfate, filtered and concentrated to a residue that was purified by silica gel column chromatography with a 0–30% diethyl ether in hexanes gradient to give (−)-(1R,4S)-4-(tert-butyl-dimethyl-silanyloxy)-cyclopent-2-enol as a colorless oil. (Yield 1.29 g, 85%).

HRMS m/z calcd for $C_{11}H_{22}O_2Si$ [M+Na]$^+$: 237.1281. Found: 237.1284.

Example 27b (−)-(1S,3R)-3-(tert-Butyl-dimethyl-silanyloxy)-cyclopentanol

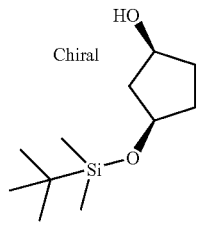

A solution of (−)-(1R,4S)-4-(tert-butyl-dimethyl-silanyloxy)-cyclopent-2-enol (1.2 g, 5.6 mmol) (from Example 27a supra) and Wilkinson's catalyst (520 mg, 0.56 mmol) (Aldrich) in toluene (50 mL) was subjected to hydrogenation at atmospheric pressure for 16 hours. The reaction mixture was filtered and partitioned between ethyl acetate and water. The organic layer was collected, dried over sodium sulfate, filtered and concentrated. The resulting residue was purified by chromatography on a silica gel column using a 0–30% diethyl ether in hexanes gradient to give (−)-(1S,3R)-3-(tert-butyl-dimethyl-silanyloxy)-cyclopentanol as a colorless oil. (Yield 790 mg, 65%).

HRMS m/z calculated for $C_{11}H_{24}O_2Si$ [M+Na]$^+$: 239.1438. Found: 239.1441.

Example 27c (−)-(1R,3R)-(3-Azido-cyclopentyloxy)-tert-butyl-dimethyl-silane

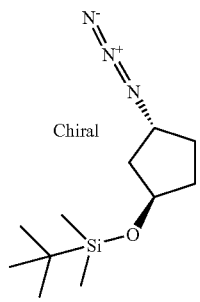

To a mixture of (−)-(1S,3R)-3-(tert-butyl-dimethyl-silanyloxy)-cyclopentanol (670 mg, 3.09 mmol) (from Example 27b supra) and triphenyl phosphine (1.06 g, 4.02 mmol) (Aldrich) in anhydrous tetrahydrofuran (60 mL) cooled at 0° C. was added dropwise diethyl azodicarboxylate (640 μL, 0.70 g, 4.02 mmol) (Aldrich). After 2 to 3 minutes, followed a dropwise addition of diphenylphosphoryl azide (860 μL, 1.1 g, 4.02 mmol) (Aldrich). The mixture was allowed to slowly warm up to room temperature and after overnight stirring was partitioned between ethyl acetate and water. The organic layer was collected, dried over sodium sulfate filtered and concentrated to a residue that was purified by chromatography with a silica gel column using a 0–20% diethyl ether in hexanes gradient to give (−)-(1R,3R)-(3-azido-cyclopentyloxy)-tert-butyl-dimethyl-silane as a colorless liquid. (Yield 540 mg, 72%).

Example 27d (+)-(1R,3R)-4-[3-(tert-Butyl-dimethyl-silanyloxy)-cyclopentylamino]-2-methylsulfanyl-pyrimidine-5-carboxylic acid ethyl ester

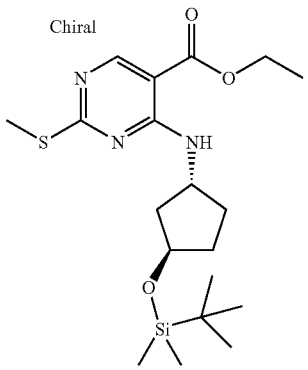

To a solution of (−)-(1R,3R)-(3-azido-cyclopentyloxy)-tert-butyl-dimethyl-silane (540 mg, 2.24 mmol) (from Example 27c supra) in ethanol (30 mL) was added platinum oxide (51 mg, 0.22 mmol) (Aldrich) and the mixture was hydrogenated under 1 atmosphere of hydrogen overnight. The mixture was then filtered, the solids were washed with tetrahydrofuran (approximately 25 mL) and the combined filtrate was concentrated to a residue that was dissolved in dioxane (50 mL). To that solution was added triethylamine (620 μL, 450 mg, 4.48 mmol) (Aldrich) and ethyl 4-chloro-2-methylthio-5-pyrimidinecarboxylate (520 mg, 2.24 mmol) (Aldrich) and the mixture was stirred at reflux for 1 hour. The reaction mixture was then cooled and partitioned between ethyl acetate and water. The ethyl acetate layer was collected, dried over sodium sulfate and concentrated to a residue that was purified by silica gel column chromatography with a 0–20% ethyl acetate in hexanes gradient to give (+)-(1R,3R)-4-[3-(tert-butyl-dimethyl-silanyloxy)-cyclopentylamino]-2-methylsulfanyl-pyrimidine-5-carboxylic acid ethyl ester as a colorless viscous oil. (Yield 710 mg, 77%).

Example 27e (−)-(1R,3R)-1-[3-(tert-Butyl-dimethyl-silanyloxy)-cyclopentyl]-3-(4-methoxy-phenyl)-7-phenylamino-3,4-dihydro-1H-pyrimido[4,5-d]pyrimidin-2-one

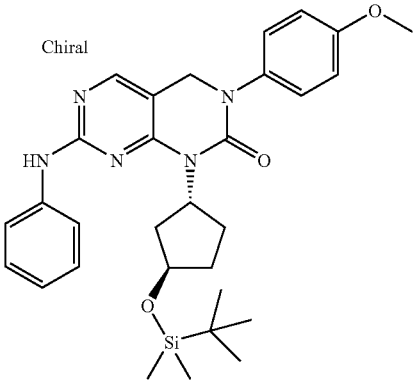

To a mixture of (+)-(1R,3R)-4-[3-(tert-butyl-dimethyl-silanyloxy)-cyclopentylamino]-2-methylsulfanyl-pyrimidine-5-carboxylic acid ethyl ester (710 mg, 1.73 mmol) (from Example 27d supra) in anhydrous tetrahydrofuran (50 mL) at 0° C. was added in portions lithium aluminum hydride (196 mg, 5.19 mmol) (Aldrich). The slurry that resulted was allowed to slowly warm up to room temperature and after stirring for 5.5 hours was poured in portions to a vigorously stirred mixture of ethyl acetate and saturated aqueous potassium sodium tartrate solution. The organic layer was then collected, dried over sodium sulfate, filtered and concentrated to a solid residue that was dissolved in dichloromethane (50 mL). To this solution was added manganese dioxide (1.5 g, 17.30 mmol) (Aldrich) and the resulting slurry was stirred for 3.5 hours and then filtered. The solids were washed with tetrahydrofuran (approximately 30 mL) and the combined filtrate was concentrated to a residue that was dissolved in benzene (60 mL). That solution was treated with p-anisidine (180 mg, 1.49 mmol) (Aldrich) and p-toluenesulfonic acid mono-hydrate (25 mg) (Aldrich) and refluxed using a Dean Stark apparatus overnight. The mixture was then cooled, partitioned between ethyl acetate and water and the organic layer was collected, dried over sodium sulfate, filtered and concentrated. The residue was dissolved in anhydrous tetrahydrofuran (50 mL) and the solution that resulted was cooled at 0° C. To this solution was added lithium aluminum hydride (150 mg, 4.08 mmol) in small portions and the slurry that formed was allowed to slowly warm up to room temperature. After stirring overnight the slurry was poured in portions into a mixture of ethyl acetate and saturated aqueous potassium sodium tartrate solution. The organic layer was collected, dried over sodium sulfate, filtered and concentrated and the residue was purified by chromatography on a silica gel column with a 0–30% ethyl acetate in hexanes gradient. The intermediate obtained from that purification was then dissolved in dichloromethane (80 mL) and that solution was treated with triethylamine (490 μL, 0.35 g, 3.47 mmol) (Aldrich) and cooled at 0° C. This was followed by a dropwise addition of a 20% phosgene in toluene solution (570 μL, 1.16 mmol) (Fluka). The reaction mixture was stirred at 0° C. for 20 minutes and at room temperature for 1 hour and then partitioned between ethyl acetate and water. The organic layer was collected, dried over sodium sulfate, filtered and concentrated. The residue was purified by chromatography on a silica gel column with a 0–30% ethyl acetate in hexanes gradient. The intermediate from this purification was dissolved in tetrahydrofuran (50 mL). This solution was then treated with 3-chloroperoxy-benzoic acid (75%, 320 mg, 1.43 mmol) (Aldrich) stirred overnight and partitioned between ethyl acetate and saturated aqueous potassium carbonate solution. The organic layer was collected, dried over sodium sulfate, filtered and concentrated to a solid residue. This residue was dissolved in aniline (3 mL) (Aldrich) and stirred at 75° C. for 16.5 hours. The mixture was then cooled, and purified by silica gel column chromatography with a 0–20% diethyl ether in toluene gradient to give (−)-(1R,3R)-1-[3-(tert-butyl-dimethyl-silanyloxy)-cyclopentyl]-3-(4-methoxy-phenyl)-7-phenylamino-3,4-dihydro-1H-pyrimido[4,5-d]pyrimidin-2-one as an off-white solid. (Yield 152 mg, 68%).

HRMS m/z calcd for $C_{30}H_{39}N_5O_3Si$ [M+H]$^+$: 546.2895. Found: 546.2901.

Example 27f (+)-(1R,3R)-1-(3-Hydroxy-cyclopentyl)-3-(4-methoxy-phenyl)-7-phenylamino-3,4-dihydro-1H-pyrimido[4,5-d]pyrimidin-2-one

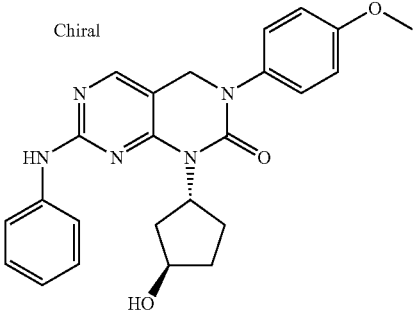

(−)-(1R,3R)-1-[3-(tert-Butyl-dimethyl-silanyloxy)-cyclopentyl]-3-(4-methoxy-phenyl)-7-phenylamino-3,4-dihydro-1H-pyrimido[4,5-d]pyrimidin-2-one (148 mg, 0.27 mmol) (from Example 27e supra) was dissolved at 0° C. in a 25% trifluoroacetic acid in dichloromethane solution (5 mL) that contained water (300 μL). After stirring for 30 minutes the reaction mixture was partitioned between ethyl acetate and 0.5 N aqueous sodium hydroxide. The pH of the aqueous layer was adjusted to 12 via the addition of solid sodium hydroxide. The organic layer was then collected, dried over sodium sulfate, filtered and concentrated to give the crude product. Purification by silica gel column chromatography using a 0–100% ethyl acetate in hexanes to 0–40% tetrahydrofuran in ethyl acetate gradient followed by a precipitation out of dichloromethane with excess pentane afforded (+)-(1R,3R)-1-(3-hydroxy-cyclopentyl)-3-(4-methoxy-phenyl)-7-phenylamino-3,4-dihydro-1H-pyrimido[4,5-d]pyrimidin-2-one as a white solid. (Yield 92 mg, 86%).

HRMS m/z calcd for $C_{24}H_{25}N_5O_3$ [M+H]$^+$: 432.2030. Found: 432.2035.

Example 28a (R)-3-(tert-Butyl-diphenyl-silanyloxy)-butyric acid

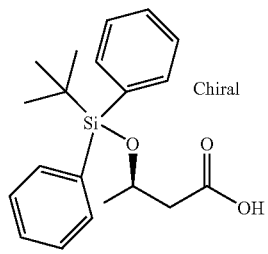

Methyl (R)-(−)-3-hydroxybutyrate (0.31 g, 2.61 mmol) (Aldrich) was dissolved in dichloromethane (3.5 mL, dried over molecular sieves). Imidazole (0.25 g, 3.66 mmol) (Aldrich) was added. When all had dissolved, tert-butyl-diphenylsilyl chloride (0.69 mL, 2.63 mmol) (Aldrich) was added dropwise and the mixture was stirred at room temperature for 4.5 hours. The reaction mixture was diluted with additional dichloromethane, washed with water (2×) and brine, dried over anhydrous sodium sulfate, filtered and concentrated. Purification by flash chromatography (Biotage 40M, 5:95 ethyl acetate-hexanes) gave (R)-3-(tert-butyl-diphenyl-silanyloxy)-butyric acid methyl ester. (Yield 0.85 g, 91.2%).

The protected ester (0.84 g, 2.36 mmol) was dissolved in 3:1 tetrahydrofuran-methanol and treated with aqueous sodium hydroxide (1.0 N, 3.0 mL, 3.00 mmol) at ~42° C. overnight. The reaction was concentrated. The residue was partitioned between ethyl acetate and water and acidified with 1 N aqueous hydrochloric acid. The organic phase was washed with brine, dried over anhydrous sodium sulfate, filtered and concentrated. Purification by flash chromatography (Biotage 40M, 20:80 ethyl acetate-hexanes) gave (R)-3-(tert-butyl-diphenyl-silanyloxy)-butyric acid. (Yield 0.63 g, 69.9%).

Example 28b (R)-tert-Butyl-(2-isocyanato-1-methyl-ethoxy)-diphenyl-silane

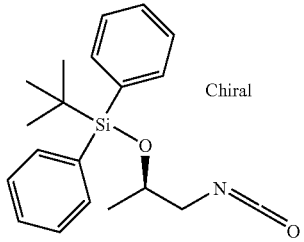

(R)-3-(tert-Butyl-diphenyl-silanyloxy)-butyric acid (0.81 g, 2.25 mmol) (from Example 28a supra) was dissolved in dichloromethane (8 mL, dried over molecular sieves). Triethylamine (0.63 mL, 4.52 mmol) (Aldrich) was added and the resulting solution was cooled in an ice-water bath. Ethyl chloroformate (0.26 mL, 2.72 mmol) (Aldrich) was then added dropwise and the mixture was stirred in the cold for 50 minutes. The reaction mixture was diluted with additional dichloromethane and washed with water and brine. The organic phase was dried over anhydrous sodium sulfate, filtered and concentrated to give the intermediate mixed anhydride.

The intermediate mixed anhydride was dissolved in acetone (8 mL) and treated with a solution of sodium azide (0.44 g, 6.76 mmol) (Aldrich). After stirring at room temperature for 10 minutes, the reaction was diluted with dichloromethane and water. The organic phase was washed with brine, dried over magnesium sulfate, filtered and concentrated to give (R)-3-(tert-butyl-diphenyl-silanyloxy)-butyryl azide. This crude azide was dissolved in toluene (6 mL) and heated in an oil bath at 120° C. Vigorous nitrogen gas evolution quickly resulted yielding the desired (R)-tert-butyl-(2-isocyanato-1-methyl-ethoxy)-diphenyl-silane by the Curtius rearrangement. This material was used as is in the next step.

Example 28c (R)-1-[2-(tert-Butyl-diphenyl-silanyloxy)-propyl]-7-chloro-3-(4-methoxy-phenyl)-3,4-dihydro-1H-pyrimido[4,5-d]pyrimidin-2-one

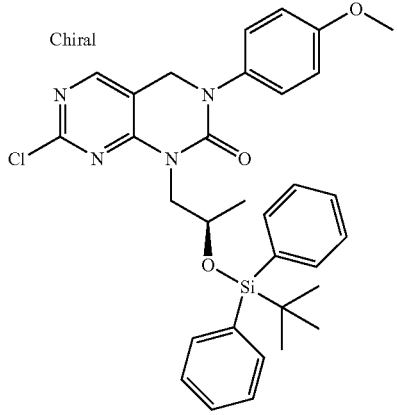

(R)-tert-Butyl-(2-isocyanato-1-methyl-ethoxy)-diphenyl-silane (generated in situ from 0.81 g, 2.25 mmol of (R)-3-(tert-butyl-diphenyl-silanyloxy)-butyric acid) (from Example 28b supra) in hot toluene (6 mL) was treated with [(2,4-dichloropyrimidin-5-yl)methyl](4-methoxyphenyl)amine (0.57 g, 2.02 mmol) (from Example 1d supra). The solution was heated at 120° C. for 45 minutes and then cooled to room temperature and concentrated to give the intermediate urea.

This urea was dissolved in anhydrous tetrahydrofuran (7.5 mL) and cooled in an ice-brine bath. Potassium tert-butoxide (1.0 N in tetrahydrofuran, 2.15 mL, 2.15 mmol) (Aldrich) was added dropwise. The mixture was stirred in the cold for 15 minutes and then the bath was removed and stirring continued for another 5 minutes. The reaction mixture was filtered through a bed of silica gel and eluted with ethyl acetate. Purification by flash chromatography (Biotage 40M, ethyl acetate-hexanes gradient [20–40% ethyl acetate]) gave the desired intermediate, contaminated with the uncyclized urea intermediate.

The purified mixture (1.02 g) was dissolved in anhydrous tetrahydrofuran (6 mL) and treated again with potassium tert-butoxide (1.4 mL, 1.40 mmol) as above. Purification (Biotage 40M, ethyl acetate-hexanes gradient (30–40% ethyl acetate) gave (R)-1-[2-(tert-butyl-diphenyl-silanyloxy)-propyl]-7-chloro-3-(4-methoxy-phenyl)-3,4-dihydro-1H-pyrimido[4,5-d]pyrimidin-2-one. (Yield 0.78 g, 65.0%).

Example 28d (R)-1-(2-Hydroxy-propyl)-3-(4-methoxy-phenyl)-7-phenylamino-3,4-dihydro-1H-pyrimido[4,5-d]pyrimidin-2-one

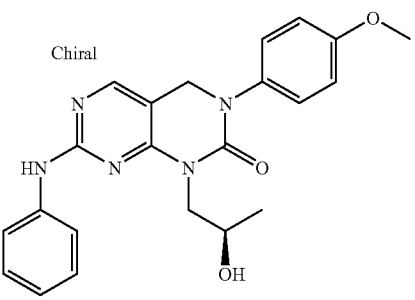

(R)-1-[2-(tert-Butyl-diphenyl-silanyloxy)-propyl]-7-chloro-3-(4-methoxy-phenyl)-3,4-dihydro-1H-pyrimido[4, 5-d]pyrimidin-2-one (0.71 g, 1.15 mmol) (from Example 28c supra) was combined with aniline (1.00 mL, 10.97 mmol) (Aldrich) and heated in an oil bath at 110° C. for 75 minutes. Upon cooling to room temperature, the residue was triturated with hexanes. The supernatant was discarded and the residue was dissolved in ethyl acetate, washed with water and brine, dried over anhydrous sodium sulfate, filtered and concentrated. Purification by flash chromatography (Biotage 40M, ethyl acetate-hexanes gradient [20–40% ethyl acetate]) gave the intermediate (R)-1-(2-tert-butyl-diphenyl-silanyloxy-propyl)-3-(4-methoxy-phenyl)-7-phenylamino-3,4-dihydro-1H-pyrimido[4,5-d]pyrimidin-2-one. (Yield 0.73 g, 91.9%).

(R)-1-(2-tert-Butyl-diphenyl-silanyloxy-propyl)-3-(4-methoxy-phenyl)-7-phenylamino-3,4-dihydro-1H-pyrimido[4,5-d]pyrimidin-2-one was dissolved in anhydrous tetrahydrofuran (7 mL) and treated with tetrabutylammonium fluoride (1.0 M in tetrahydrofuran, 4.2 mL, 4.20 mmol) (Aldrich) in an oil bath at 45° C. overnight. The reaction mixture was concentrated and the residue dissolved in ethyl acetate and washed with water and brine. The organic phase was dried over anhydrous sodium sulfate, filtered and concentrated. The crude material was purified by flash chromatography (Biotage 40M, 80:20 ethyl acetate-hexanes) and crystallized from ethyl acetate-hexanes to give (R)-(−)-1-(2-hydroxy-propyl)-3-(4-methoxy-phenyl)-7-phenylamino-3,4-dihydro-1H-pyrimido[4,5-d]pyrimidin-2-one. (Yield 0.25 g, 58.9%). Melting Point: 189–193° C.

HR-MS (ES$^+$) m/z Calculated for $C_{22}H_{23}N_5O_3$ [M+H]$^+$: 406.1874. Found: 406.1878.

Example 29a (+)-(1S,4R)-4-(tert-Butyl-dimethyl-silanyloxy)-cyclopent-2-enol

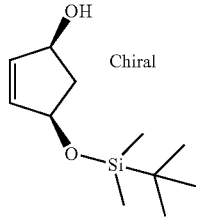

To a solution of (1R,4S)-4-acetoxy-2-cyclopenten-1-ol (1.0 g, 7.03 mmol) (Fluka) and imidazole (960 mg, 14.06 mmol) (Aldrich) in tetrahydrofuran (65 mL) at 0° C. was added tert-butyldimethylsilyl chloride (1.27 g, 8.44 mmol) (Aldrich). The mixture was allowed to warm slowly to room temperature, stirred overnight and then partitioned between ethyl acetate and water. The organic layer was collected, dried over sodium sulfate, filtered and concentrated to a residue that was dissolved in methanol (approximately 45 mL). To this solution was added potassium carbonate (1.17 g, 8.44 mmol) and the mixture stirred overnight. The reaction mixture was then partitioned between ethyl acetate and water. The organic layer was collected, dried over sodium sulfate, filtered and concentrated to a residue that was purified by silica gel column chromatography with a 0–30% diethyl ether in hexanes gradient to give (+)-(1S,4R)-4-(tert-butyl-dimethyl-silanyloxy)-cyclopent-2-enol as a colorless oil. (Yield 1.43 g, 95%).

Example 29b (+)-(1R,3S)-3-(tert-Butyl-dimethyl-silanyloxy)-cyclopentanol

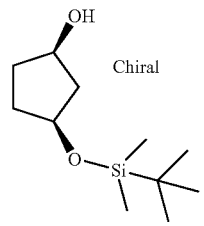

A solution of (+)-(1S,4R)-4-(tert-butyl-dimethyl-silanyloxy)-cyclopent-2-enol (1.43 g, 6.67 mmol) (from Example 29a supra) and Wilkinson's catalyst (1.23 g, 1.33 mmol) (Aldrich) in toluene (55 mL) was subjected to atmospheric pressure hydrogenation for 16.5 hours. The reaction mixture was then filtered, concentrated to a small volume, and purified by silica gel column chromatography with a 0–25% ethyl acetate in hexanes gradient to give (+)-(1R,3S)-3-(tert-butyl-dimethyl-silanyloxy)-cyclopentanol as a colorless oil. (Yield 745 mg, 61%).

Example 29c (+)-(1S,3S)-(3-Azido-cyclopentyloxy)-tert-butyl-dimethyl-silane

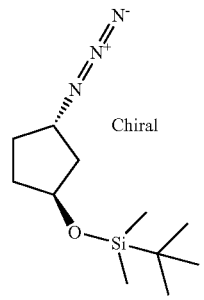

To a 0° C. solution of (+)-(1R,3S)-3-(tert-butyl-dimethyl-silanyloxy)-cyclopentanol (745 mg, 3.44 mmol) (from Example 29b supra) and triphenyl phosphine (1.17 g, 4.47 mmol) (Aldrich) in anhydrous tetrahydrofuran (60 mL) was added dropwise diethyl azodicarboxylate (710 µL, 780 mg, 4.47 mmol) (Aldrich). After 2 to 3 minutes followed a dropwise addition of diphenylphosphoryl azide (950 µL, 1.23 g, 4.47 mmol) (Aldrich). The mixture was allowed to warm up slowly to room temperature stirred overnight and then partitioned between ethyl acetate and water. The organic layer was collected, dried over sodium sulfate, filtered, concentrated and the resulting residue was chromatographed on a silica gel column with a 0–20% diethyl ether in hexanes gradient to give (+)-(1S,3S)-(3-azido-cyclopentyloxy)-tert-butyl-dimethyl-silane as a colorless liquid. (Yield 589 mg, 70%).

HRMS m/z calcd for $C_{11}H_{23}N_3OSi$ [M]$^+$: 241.1610. Found: 241.1613.

Example 29d (-)-(1S,3S)-4-[3-(tert-Butyl-dimethyl-silanyloxy)-cyclopentylamino]-2-methylsulfanyl-pyrimidine-5-carboxylic acid ethyl ester

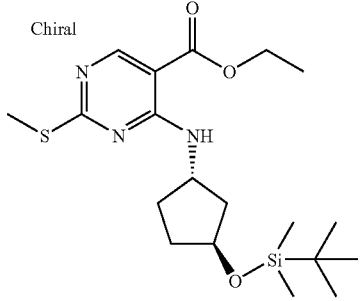

To a solution of (+)-(1S,3S)-(3-azido-cyclopentyloxy)-tert-butyl-dimethyl-silane (580 mg, 2.40 mmol) (from Example 29c supra) in ethanol (30 mL) was added platinum oxide (55 mg, 0.24 mmol) (Aldrich). The mixture was hydrogenated under 1 atmosphere of hydrogen overnight. The reaction mixture was then filtered, the solids were washed with tetrahydrofuran (approximately 30 mL) and the combined filtrate was concentrated to a residue that was dissolved in dioxane (50 mL). To this solution was added triethylamine (970 µL, 705 mg, 6.96 mmol) (Aldrich) and ethyl 4-chloro-2-methylthio-5-pyrimidinecarboxylate (594 mg, 2.55 mmol) (Aldrich) and the mixture was heated at reflux for 45 minutes then cooled and partitioned between ethyl acetate and water. The organic layer was collected, dried over sodium sulfate, filtered and concentrated to a residue that was purified by chromatography on a silica gel column with a 0–20% ethyl acetate in hexanes gradient to give (−)-(1S,3S)-4-[3-(tert-butyl-dimethyl-silanyloxy)-cyclopentylamino]-2-methylsulfanyl-pyrimidine-5-carboxylic acid ethyl ester as a colorless viscous oil. (Yield 910 mg, 95%).

HRMS m/z calcd for $C_{19}H_{33}N_3O_3SSi$ [M+H]$^+$: 412.2085. Found: 412.2088.

Example 29e (-)-(1S,3S)-4-[3-(tert-Butyl-dimethyl-silanyloxy)-cyclopentylamino]-2-methylsulfanyl-pyrimidine-5-carbaldehyde

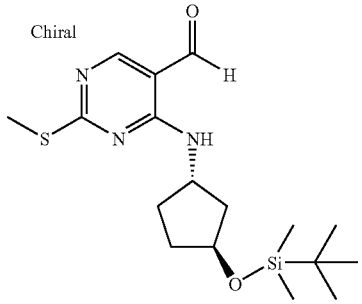

To a solution of (−)-(1S,3S)-4-[3-(tert-butyl-dimethyl-silanyloxy)-cyclopentylamino]-2-methylsulfanyl-pyrimidine-5-carboxylic acid ethyl ester (910 mg, 2.21 mmol) (from Example 29d supra) in tetrahydrofuran (55 mL) at 0° C. was added in portions lithium aluminum hydride (250 mg, 6.63 mmol) (Aldrich). The reaction mixture was allowed to slowly warm up to room temperature. After stirring overnight the reaction mixture was poured in portions into a vigorously stirred mixture of ethyl acetate and saturated aqueous potassium sodium tartrate solution. The organic layer was collected, dried over sodium sulfate, filtered and concentrated to a solid that was then dissolved in dichloromethane (55 mL). To this solution was added manganese dioxide (1.92 g, 22.11 mmol) (Aldrich) and the mixture was stirred overnight. The slurry was filtered, the solids were washed with tetrahydrofuran (approximately 25 mL) and the combined organic layer was evaporated to a residue that was purified by chromatography on a silica gel column with a 0–50% diethyl ether in hexanes gradient to give (−)-(1S,3S)-4-[3-(tert-butyl-dimethyl-silanyloxy)-cyclopentylamino]-2-methylsulfanyl-pyrimidine-5-carbaldehyde as a viscous colorless oil. (Yield 615 mg, 76%).

HRMS m/z calcd for $C_{17}H_{29}N_3O_2SSi$ [M+H]$^+$: 368.1823. Found: 368.1825.

Example 29f (-)-(1S,3S)-1-[3-(tert-Butyl-dimethyl-silanyloxy)-cyclopentyl]-3-(4-methoxy-phenyl)-7-methylsulfanyl-3,4-dihydro-1H-pyrimido[4,5-d]pyrimidin-2-one

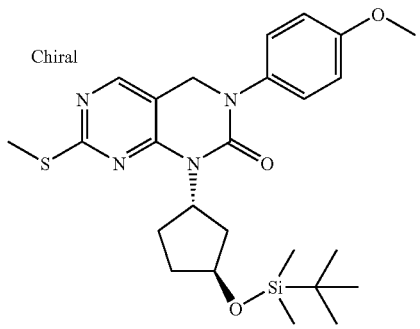

A mixture of (−)-(1S,3S)-4-[3-(tert-butyl-dimethyl-silanyloxy)-cyclopentylamino]-2-methylsulfanyl-pyrimidine-5-carbaldehyde (596 mg, 1.62 mmol) (from Example 29e supra), p-anisidine (210 mg, 1.70 mmol) (Aldrich) and a catalytic amount of p-toluenesulfonic acid mono-hydrate (25 mg) (Aldrich) was heated at reflux using a Dean Stark apparatus for 16 hours. The mixture was then cooled and partitioned between ethyl acetate and water. The organic layer was collected, dried over sodium sulfate, filtered and concentrated. The residue was dissolved in anhydrous tetrahydrofuran (60 mL) and the solution that resulted was cooled to 0° C. This was followed by the addition of lithium aluminum hydride (184 mg, 4.87 mmol) in portions and the slurry formed was allowed to slowly warm up to room temperature. After stirring overnight the reaction mixture was added in portions to a vigorously stirred mixture of ethyl acetate and saturated aqueous potassium sodium tartrate solution. The organic layer was collected, dried over sodium sulfate, filtered, concentrated and the residue was purified by chromatography with a silica gel column using a 0–30% ethyl acetate in hexanes gradient. The product from this purification was dissolved in dichloromethane (50 mL). To this solution was added triethylamine (910 µL, 0.66 g, 6.54 mmol) (Aldrich) and the mixture was cooled to 0° C. Followed a dropwise addition of a 20% phosgene in toluene solution (670 µL, 1.37 mmol) (Fluka). After stirring for 20 minutes at 0° C. and 1 hour at room temperature the reaction mixture was partitioned between ethyl acetate and water. The organic layer was collected, dried over sodium sulfate, filtered and concentrated to a residue that was purified by chromatography on a silica gel column with 0–30% ethyl acetate in hexanes gradient to give (−)-(1S,3S)-1-[3-(tert-butyl-dimethyl-silanyloxy)-cyclopentyl]-3-(4-methoxy-phenyl)-7-methylsulfanyl-3,4-dihydro-1H-pyrimido[4,5-d]pyrimidin-2-one as an off-white foamy solid. (Yield 620 mg, 76%).

HRMS m/z calcd for $C_{25}H_{36}N_4O_3SSi$ $[M+H]^+$: 501.2350. Found: 501.2358.

Example 29g (−)-(1S,3S)-1-[3-(tert-Butyl-dimethyl-silanyloxy)-cyclopentyl]-3-(4-methoxy-phenyl)-7-phenylamino-3,4-dihydro-1H-pyrimido[4,5-d]pyrimidin-2-one

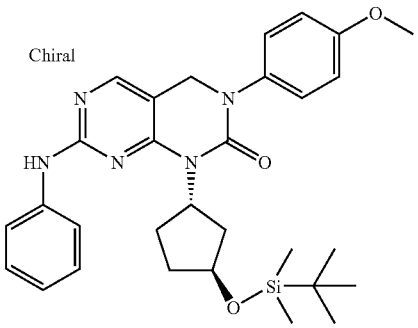

A solution of (−)-(1S,3S)-1-[3-(tert-butyl-dimethyl-silanyloxy)-cyclopentyl]-3-(4-methoxy-phenyl)-7-methylsulfanyl-3,4-dihydro-1H-pyrimido[4,5-d]pyrimidin-2-one (610 mg, 1.22 mmol) (from Example 29f supra) in dichloromethane (50 mL) was treated with 3-chloroperoxybenzoic acid (75%, 590 mg, 2.56 mmol) (Aldrich). After stirring overnight the mixture was partitioned between ethyl acetate and saturated aqueous potassium carbonate solution. The organic layer was collected, dried over sodium sulfate, filtered and concentrated to a solid that was dissolved in aniline (7 mL) (Aldrich). This solution was stirred at 95° C. for 6 hours then cooled and chromatographed with a silica gel column using a 0–20% diethyl ether in toluene gradient to give (−)-(1S,3S)-1-[3-(tert-butyl-dimethyl-silanyloxy)-cyclopentyl]-3-(4-methoxy-phenyl)-7-phenylamino-3,4-dihydro-1H-pyrimido[4,5-d]pyrimidin-2-one as a white solid. (Yield 450 mg, 68%).

HRMS m/z calculated for $C_{30}H_{39}N_5O_3Si$ $[M+H]^+$: 546.2895. Found: 546.2902.

Example 29h (−)-(1S,3S)-1-(3-Hydroxy-cyclopentyl)-3-(4-methoxy-phenyl)-7-phenylamino-3,4-dihydro-1H-pyrimido[4,5-d]pyrimidin-2-one

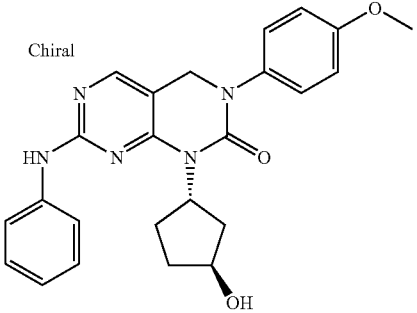

(−)-(1S,3S)-1-[3-(tert-Butyl-dimethyl-silanyloxy)-cyclopentyl]-3-(4-methoxy-phenyl)-7-phenylamino-3,4-dihydro-1H-pyrimido[4,5-d]pyrimidin-2-one (445 mg, 0.82 mmol) (from Example 29g supra) was dissolved in a 25% trifluoroacetic acid in dichloromethane solution (5 mL) and water (300 µL) at 0° C. After stirring for 30 minutes the mixture was partitioned between ethyl acetate and 1 N aqueous sodium hydroxide and the pH of the aqueous layer was adjusted to 12 via the addition of solid sodium hydroxide. The organic layer was collected, dried over sodium sulfate, filtered and concentrated to a residue that was purified by chromatography with a silica gel column and a 0–100 ethyl acetate in hexanes to 0–40% tetrahydrofuran in ethyl acetate gradient to give (−)-(1S,3S)-1-(3-hydroxy-cyclopentyl)-3-(4-methoxy-phenyl)-7-phenylamino-3,4-dihydro-1H-pyrimido[4,5-d]pyrimidin-2-one as a white solid. (Yield 307 mg, 86%).

HRMS m/z calcd for $C_{24}H_{25}N_5O_3$ $[M+H]^+$: 432.2030. Found: 432.2036.

Example 30

3-[-3-(4-Methoxy-phenyl)-2-oxo-7-phenylamino-3,4-dihydro-1H-pyrimido[4,5-d]pyrimidin-1-yl]-propionamide

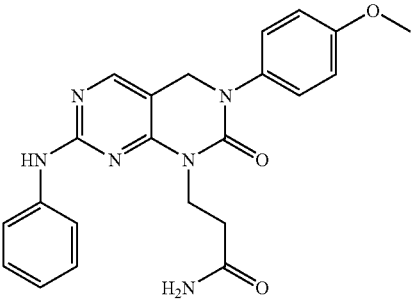

To the solution of 3-[-3-(4-methoxy-phenyl)-2-oxo-7-phenylamino-3,4-dihydro-1H-pyrimido[4,5-d]pyrimidin-1-yl]-propionitrile (60 mg, 0.15 mmol) (from Example 26 supra) in dimethyl sulfoxide (2 mL) at 0 C was added 1.0 N aqueous sodium hydroxide solution (0.42 mL, 0.42 mmol) followed by 35% aqueous hydrogen peroxide (0.35 mL) (Fisher). The reaction mixture was stirred at 0° C. for 2 hours and then at room temperature overnight. The reaction was diluted with ethyl acetate (50 mL) and washed with water (3×20 mL). The organic layer was washed with brine (10 mL) and dried over anhydrous sodium sulfate, filtered, and concentrated under reduced pressure to give the crude solid (71 mg) which was purified by recrystallization from hexanes-ethyl acetate to give 3-[-3-(4-methoxy-phenyl)-2-oxo-7-phenylamino-3,4-dihydro-1H-pyrimido[4,5-d]pyrimidin-1-yl]-propionamide as a gray solid. (Yield 28.3 mg, 45.1%).

Example 31a (S)-3-(tert-Butyl-diphenyl-silanyloxy)-butyric acid

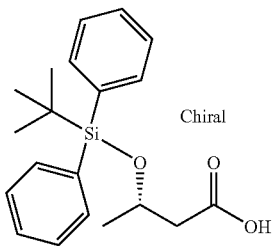

Methyl (S)-(+)-3-hydroxybutyrate (0.48 g, 4.04 mmol) (Aldrich) was dissolved in dichloromethane (6 mL, dried over molecular sieves). Imidazole (0.39 g, 5.65 mmol) (Aldrich) was added. When all had dissolved, tert-butyldiphenylsilyl chloride (1.05 mL, 4.04 mmol) was added dropwise and the mixture was stirred at room temperature for 4.5 hours. The reaction mixture was diluted with additional dichloromethane, washed with water (2×) and brine, dried over anhydrous sodium sulfate, filtered and concentrated. Purification by flash chromatography (Biotage 40M, 5:95 ethyl acetate-hexanes) gave (S)-3-(tert-butyl-diphenyl-silanyloxy)-butyric acid methyl ester. (Yield 1.33 g, 92.4%).

The methyl ester (1.33 g, 3.73 mmol) was dissolved in 3:1 tetrahydrofuran-methanol (12 mL) and treated with aqueous sodium hydroxide (1 N, 4.3 mL, 4.30 mmol) at 45° C. overnight. The reaction mixture was concentrated after 17 hours. The residue was partitioned between ethyl acetate and water and acidified with 1 N aqueous hydrochloric acid. The organic phase was washed with brine, dried over anhydrous sodium sulfate and concentrated. Purification by flash chromatography (Biotage 40M, 20:80 ethyl acetate-hexanes) gave (S)-3-(tert-butyl-diphenyl-silanyloxy)-butyric acid. (Yield 0.89 g, 62.2%).

Example 31b (S)-tert-Butyl-(2-isocyanato-1-methyl-ethoxy)-diphenyl-silane

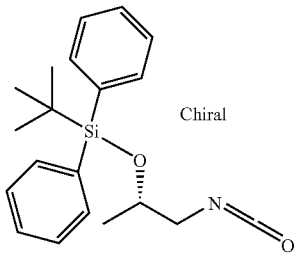

(S)-3-(tert-Butyl-diphenyl-silanyloxy)-butyric acid (0.88 g, 2.51 mmol) (from Example 31a supra) was dissolved in dichloromethane (8 mL, dried over molecular sieves). Triethylamine (0.71 mL, 5.06 mmol) (Aldrich) was added and the resulting solution was cooled in an ice-water bath. Ethyl chloroformate (0.29 mL, 3.03 mmol) (Aldrich) was added dropwise and the mixture was stirred in the cold for 50 minutes. The reaction mixture was diluted with additional dichloromethane and washed with water and brine. The organic phase was dried over anhydrous sodium sulfate, filtered and concentrated to give the crude mixed anhydride.

The intermediate mixed anhydride was dissolved in acetone (10 mL) and treated with a solution of sodium azide (0.50 g, 7.53 mmol) (Aldrich). After stirring at room temperature for 15 minutes, the reaction was diluted with dichloromethane and water. The organic phase was washed with brine, dried over magnesium sulfate, filtered, concentrated and dried briefly under high vacuum to give (S)-3-(tert-butyl-diphenyl-silanyloxy)-butyryl azide.

The crude azide was dissolved in toluene (7 mL) and heated in an oil bath at 115–120° C. for 70 minutes. Vigorous nitrogen gas evolution quickly resulted to give (S)-tert-butyl-(2-isocyanato-1-methyl-ethoxy)-diphenyl-silane by the Curtius rearrangement. This material was used without further treatment in the next step.

Example 31c (S)-1-[2-(tert-Butyl-diphenyl-silanyloxy)-propyl]-7-chloro-3-(4-methoxyphenyl)-3,4-dihydro-1H-pyrimido[4,5-d]pyrimidin-2-one

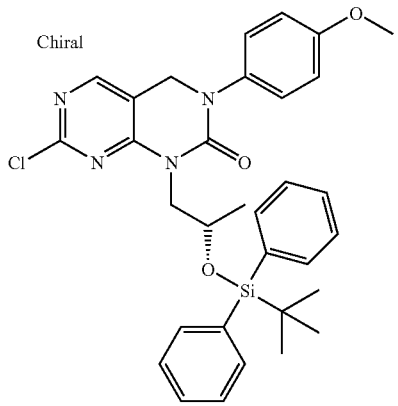

(S)-tert-Butyl-(2-isocyanato-1-methyl-ethoxy)-diphenyl-silane (generated in situ from 0.88 g, 2.51 mmol of (S)-3-(tert-butyl-diphenyl-silanyloxy)-butyric acid) (from Example 31b supra) in hot toluene (7 mL) was treated with [(2,4-dichloropyrimidin-5-yl)methyl](4-methoxyphenyl)amine (0.63 g, 2.23 mmol) (from Example 1d supra). The solution was heated at 120° C. for 50 minutes and then cooled to room temperature. The reaction mixture was purified by flash chromatography (Biotage 40M, 30:70 ethyl acetate-hexanes) to give the urea intermediate.

The purified urea intermediate (1.32 g) was dissolved in anhydrous tetrahydrofuran (5 mL), cooled in an ice-brine bath and treated with potassium tert-butoxide (1.0 M in tetrahydrofuran, 2.1 mL, 2.1 mmol) (Aldrich). The mixture was stirred in the cold for 15 minutes and then the bath was removed and stirring continued for an additional 5 minutes. The mixture was filtered through a bed of silica gel and eluted with ethyl acetate. Purification [Biotage 40M, ethyl acetate-hexanes gradient (30–35% ethyl acetate)] gave (S)-1-[2-(tert-butyl-diphenyl-silanyloxy)-propyl]-7-chloro-3-

(4-methoxy-phenyl)-3,4-dihydro-1H-pyrimido[4,5-d]pyrimidin-2-one. (Yield 0.97 g, 59.4%).

Example 31d (S)-(+)-1-(2-Hydroxy-propyl-3-(4-methoxy-phenyl)-7-phenylamino-3,4-dihydro-1H-pyrimido[4,5-d]pyrimidin-2-one

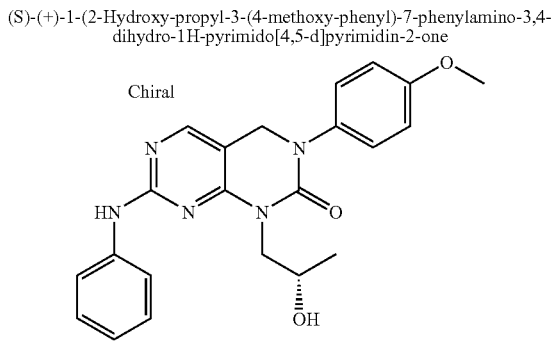

(S)-1-[2-(tert-Butyl-diphenyl-silanyloxy)-propyl]-7-chloro-3-(4-methoxy-phenyl)-3,4-dihydro-1H-pyrimido[4,5-d]pyrimidin-2-one (0.97 g,1.65 mmol) (from Example 31c supra) was combined with aniline (1.00 mL, 10.97 mmol) (Aldrich) and heated in an oil bath at 110° C. After 75 minutes, the reaction mixture was cooled to room temperature, diluted with ethyl acetate and washed with water and brine. The organic phase was dried over anhydrous sodium sulfate, filtered and concentrated. The crude material was combined with material from another experiment. The combined lot was purified by flash chromatography (Biotage 40M, ethyl acetate-hexanes gradient [20–35% ethyl acetate]) and then crystallized from ethyl acetate-hexanes to give the intermediate (S)-1-(2-tert-butyl-diphenyl-silanyloxy-propyl)-3-(4-methoxy-phenyl)-7-phenylamino-3,4-dihydro-1H-pyrimido[4,5-d]pyrimidin-2-one. (Yield 0.70 g, 59.1%).

The intermediate (S)-1-(2-tert-butyl-diphenyl-silanyloxy-propyl)-3-(4-methoxy-phenyl)-7-phenylamino-3,4-dihydro-1H-pyrimido[4,5-d]pyrimidin-2-one (0.69 g, 1.08 mmol) was dissolved in anhydrous tetrahydrofuran (7 mL). Tetrabutylammonium fluoride (1.0 M in tetrahydrofuran, 4.3 mL, 4.30 mmol) (Aldrich) was added and the reaction mixture was heated in an oil bath at 43–50° C. overnight. After cooling to room temperature, the reaction was concentrated. The residue was then taken up in ethyl acetate and washed with water and brine. The organic phase was dried over anhydrous sodium acetate. The material was purified by flash chromatography (Biotage 40M, 80:20 ethyl acetate-hexanes) and crystallized from ethyl acetate-hexanes. The product was still contaminated with a more polar impurity. This material was combined with comparable material from another reaction and recrystallized from ethyl acetate to give (S)-(+)-1-(2-hydroxy-propyl)-3-(4-methoxy-phenyl)-7-phenylamino-3,4-dihydro-1H-pyrimido[4,5-d]pyrimidin-2-one as a white solid. (Yield 0.19 g, 28.1%). Melting Point: 188–193° C.

HR-MS (ES$^+$) m/z Calculated for $C_{22}H_{23}N_5O_3$ [M+H]$^+$: 406.1874. Found: 406.1878.

Example 32a cis-3,5-Bis-(tert-butyl-diphenyl-silanyloxy)-cyclohexanecarboxylic acid methyl ester

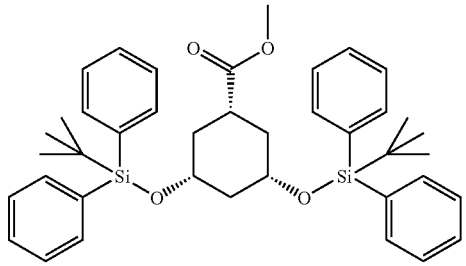

To a solution of cis-3,5-dihydroxy-cyclohexanecarboxylic acid methyl ester (1.0 g, 5.74 mmol) (prepared according to J. C. Pascal et al., U.S. Pat. No. 6,191,292, Feb. 20, 2001) in dimethylformamide (5 mL) was added imidazole (1.02 g, 14.92 mmol) (Aldrich) and tert-butyl-diphenylsilyl chloride (3.58 mL, 13.8 mmol) (Hüls America). The reaction mixture was stirred at room temperature for 1 day then diluted with ethyl acetate (20 mL) and water (20 mL). The aqueous phase was extracted with ethyl acetate (3×10 mL). The combined ethyl acetate layer was washed with water, and brine, dried over magnesium sulfate, filtered and concentrated under reduced pressure. The residue was purified by flash chromatography eluting with ethyl acetate-hexanes (5:95) to give cis-3,5-bis-(tert-butyl-diphenyl-silanyloxy)-cyclohexanecarboxylic acid methyl ester. (Yield 3.75 g, 100%).

Example 32b cis-3,5-Bis-(tert-butyl-diphenyl-silanyloxy)-cyclohexanecarboxylic acid

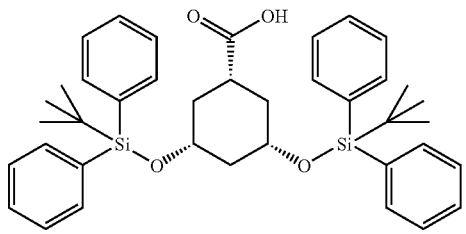

cis-3,5-Bis-(tert-butyl-diphenyl-silanyloxy)-cyclohexanecarboxylic acid methyl ester (2.65 g, 4.07 mmol) (from Example 32a supra) was dissolved in a mixture of methanol (13 mL), tetrahydrofuran (13 mL) and water (4 mL). Aqueous sodium hydroxide solution (2.5 N, 1.8 mL, 4.5 mmol) was added. The mixture was stirred at room temperature for 3 days then concentrate under reduced pressure. The residue was diluted with water and dichloromethane. The aqueous phase was acidified with conc. hydrochloric acid to pH 2 and extracted with dichloromethane (2×20 mL). The combined organic layer was washed with brine, dried over magnesium sulfate, filtered and concentrated under reduced pressure to give cis-3,5-bis-(tert-butyl-diphenyl-silanyloxy)-cyclohexanecarboxylic acid. (Yield 2.54 g, 98%).

Example 32c cis-3,5-Bis-(tert-butyl-diphenyl-silanyloxy)-5-isocyanato-cyclohexane

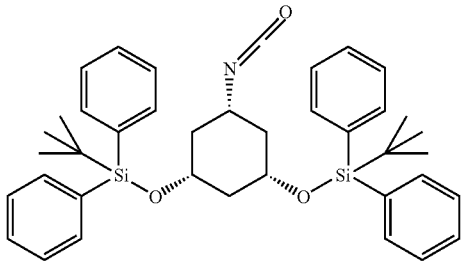

To a solution of cis-3,5-bis-(tert-butyl-diphenyl-silanyloxy)-cyclohexanecarboxylic acid (1.06 g, 1.66 mmol) (from Example 32b supra) in acetone (10 mL) at 0° C. was added triethylamine (0.28 mL, 2.0 mmol) (Burdick & Jackson) and ethyl chloroformate (0.19 mL, 2.00 mmol) (Aldrich). After the mixture was stirred for 40 minutes at 0° C., a solution of sodium azide (1.06 g, 1.66 mmol) (Aldrich) in water (5 mL) was added. The mixture was stirred at 0° C. for one more hour, then poured into ice-water (50 mL). It was extracted with ethyl acetate (3×30 mL) and the combined organic layer was washed with brine, dried over magnesium sulfate, filtered and concentrated under reduced pressure. The residue was dissolved in toluene and heated at 110° C. for 4 hours and concentrated under reduced pressure to give cis-1,3-bis-(tert-butyl-diphenyl-silanyoxy)-5-isocyanato-cyclohexane. (Yield 0.91 g, 87%).

Example 32d

1-[cis-3,5-Bis-(tert-butyl-diphenyl-silanyloxy)-cyclohexyl]-7-chloro-3-(2-fluoro-4-methoxy-phenyl)-3,4-dihydro-1H-pyrimido[4,5-d]pyrimidin-2-one

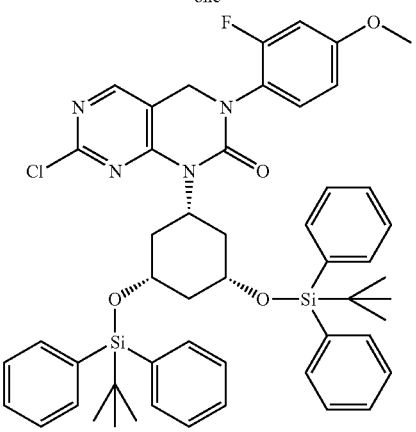

A mixture of (2,4-dichloro-pyrimidin-5-yl-methyl)-(2-fluoro-4-methoxy-phenyl)-amine (0.24 g, 0.73 mmol) (from Example 17a supra) and cis-1,3-bis-(tert-butyl-diphenyl-silanyoxy)-5-isocyanato-cyclohexane (0.46 g, 0.73 mmol) (from Example 32c supra) in toluene (10 mL) were heated to 110° C. overnight. It was concentrated under reduced pressure. The residue was dissolved in tetrahydrofuran (5 mL) and cooled to −30° C. Potassium tert-butoxide (0.9 mL, 1 M in tetrahydrofuran, 0.9 mmol) (Aldrich) was added. The mixture was stirred at room temperature overnight. It was filtered through silica gel and concentrated under reduced pressure. The residue was purified by flash chromatography eluting with ethyl acetate-hexanes (1:4) to give 1-[cis-3,5-bis-(tert-butyl-diphenyl-silanyloxy)-cyclohexyl]-7-chloro-3-(2-fluoro-4-methoxy-phenyl)-3,4-dihydro-1H-pyrimido[4,5-d]pyrimidin-2-one. (Yield 0.21 g, 29%).

Example 32e

1-[cis-3,5-Bis-(tert-butyl-diphenyl-silanyloxy)-cyclohexyl]-3-(2-fluoro-4-methoxy-phenyl)-7-(4-methoxy-phenylamino)-3,4-dihydro-1H-pyrimido[4,5-d]pyrimidin-2-one

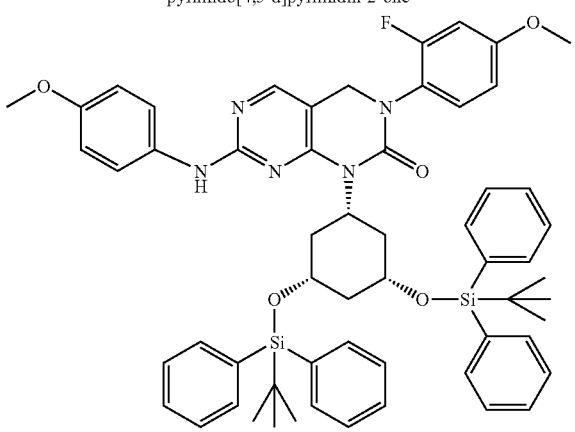

A mixture of 1-[cis-3,5-bis-(tert-butyl-diphenyl-silanyloxy)-cyclohexyl]-7-chloro-3-(2-fluoro-4-methoxy-phenyl)-3,4-dihydro-1H-pyrimido[4,5-d]pyrimidin-2-one (0.10 g, 0.11 mmol) (from Example 32d supra) and p-anisidine (17.7 mg, 0.14 mmol) (Aldrich) in 2-propanol (4 mL) was placed in a microwave reactor (SmithSynthesizer®). The reaction mixture was heated at 160° C. for 10 minutes. After cooling, it was concentrated under reduced pressure. The residue was purified by flash chromatography eluting with ethyl acetate-dichloromethane (5:95) to give 1-[cis-3,5-bis-(tert-butyl-diphenyl-silanyloxy)-cyclohexyl]-3-(2-fluoro-4-methoxy-phenyl)-7-(4-methoxy-phenylamino)-3,4-dihydro-1H-pyrimido[4,5-d]pyrimidin-2-one. (Yield 0.09 g, 60%).

Example 32f 1-(cis-3,5-Dihydroxy-cyclohexyl)-3-(2-fluoro-4-methoxy-phenyl)-7-(4-methoxyphenylamino)-3,4-dihydro-1H-pyrimido[4,5-d]pyrimidin-2-one

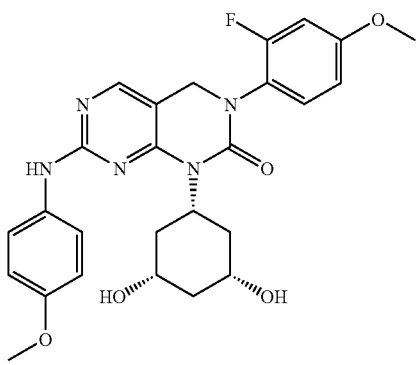

A solution of 1-[cis-3,5-bis-(tert-butyl-diphenyl-silanyloxy)-cyclohexyl]-3-(2-fluoro-4-methoxy-phenyl)-7-(4-methoxy-phenylamino)-3,4-dihydro-1H-pyrimido[4,5-d]pyrimidin-2-one (0.40 g, 0.041 mmol) (from Example 32e supra) and tetrabutylammonium fluoride (0.12 mL, 1.0 M solution in tetrahydrofuran, 0.12 mmol) (Aldrich) in tetrahydrofuran (5 mL) was heated at reflux for 3 hours. After cooling, it was concentrated under reduced pressure. The residue was purified by flash chromatography eluting with ethyl acetate-dichloromethane (5:95) to give 1-(cis-3,5-dihydroxy-cyclohexyl)-3-(2-fluoro-4-methoxy-phenyl)-7-(4-methoxyphenylamino)-3,4-dihydro-1H-pyrimido[4,5-d]pyrimidin-2-one. (Yield 10.0 mg, 48%).

Example 33a

1-[cis-3,5-Bis-(tert-butyl-diphenyl-silanyloxy)-cyclohexyl]-7-chloro-3-(4-methoxy-phenyl)-3,4-dihydro-1H-pyrimido[4,5-d]pyrimidin-2-one

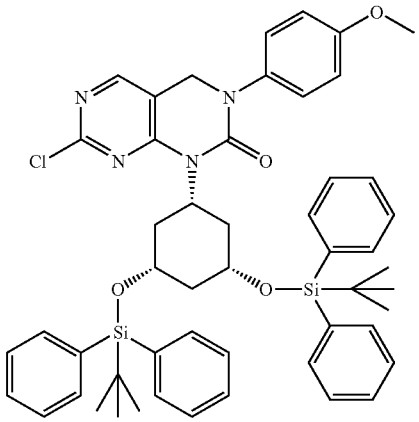

A mixture of [(2,4-dichloropyrimidin-5-yl)methyl](4-methoxyphenyl)amine (0.21 g, 0.75 mmol) (from Example 1d supra) and cis-1,3-bis-tert-butyl-(5-isocyanato-cyclohexyloxy)-diphenyl-silane (0.45 g, 0.68 mmol) (from Example 32c supra) in toluene (10 mL) was heated to 110° C. overnight. It was concentrated under reduced pressure. The residue was dissolved in tetrahydrofuran (5 mL) and cooled to −30° C. Potassium tert-butoxide (0.9 mL, 1 M in tetrahydrofuran, 0.9 mmol) (Aldrich) was added. The mixture was stirred at room temperature overnight. It was filtered through silica gel and concentrated under reduced pressure. The residue was purified by flash chromatography eluting with ethyl acetate-hexanes (1:4) to give 1-[cis-3,5-bis-(tert-butyl-diphenyl-silanyloxy)-cyclohexyl]-7-chloro-3-(4-methoxy-phenyl)-3,4-dihydro-1H-pyrimido[4,5-d]pyrimidin-2-one. (Yield 0.29 g, 44%).

Example 33b

1-[cis-3,5-Bis-(tert-butyl-diphenyl-silanyloxy)-cyclohexyl]-3-(4-methoxy-phenyl)-7-(4-methoxy-phenylamino)-3,4-dihydro-1H-pyrimido[4,5-d]pyrimidin-2-one

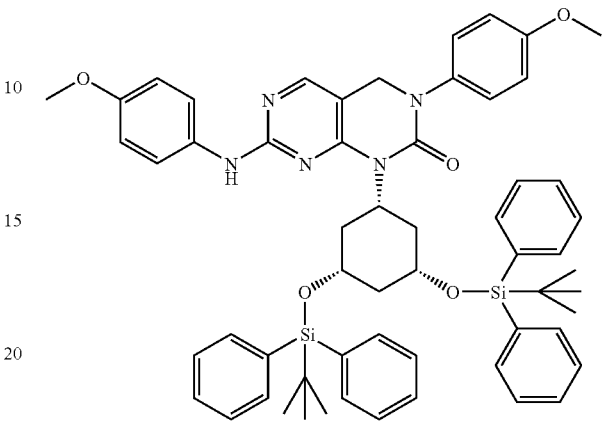

A mixture of 1-[cis-3,5-bis-(tert-butyl-diphenyl-silanyloxy)-cyclohexyl]-7-chloro-3-(4-methoxy-phenyl)-3,4-dihydro-1H-pyrimido[4,5-d]pyrimidin-2-one (0.15 g, 0.16 mmol) (from Example 33a supra) and p-anisidine (25.9 mg, 0.21 mmol) (Aldrich) in 2-propanol (4 mL) was placed in a microwave reactor (SmithSynthesizer®). The reaction mixture was heated at 160° C. for 10 minutes. After cooling, it was concentrated under reduced pressure. The residue was purified by flash chromatography eluting with ethyl acetate-hexanes (3:7 then 2:3) to give 1-[cis-3,5-bis-(tert-butyl-diphenyl-silanyloxy)-cyclohexyl]-3-(4-methoxy-phenyl)-7-(4-methoxy-phenylamino)-3,4-dihydro-1H-pyrimido[4,5-d]pyrimidin-2-one. (Yield 0.09 g, 60%).

Example 33c

1-[cis-3,5-Dihydroxy-cyclohexyl]-3-(4-methoxy-phenyl)-7-(4-methoxy-phenylamino)-3,4-dihydro-1H-pyrimido[4,5-d]pyrimidin-2-one

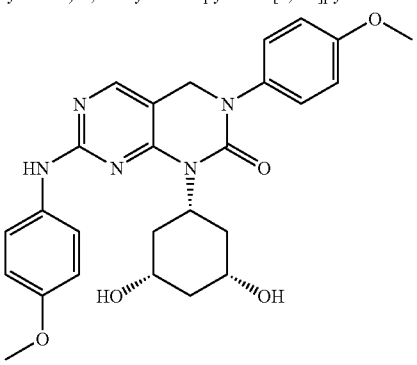

A solution of 1-[cis-3,5-bis-(tert-butyl-diphenyl-silanyloxy)-cyclohexyl]-3-(4-methoxy-phenyl)-7-(4-methoxy-phenylamino)-3,4-dihydro-1H-pyrimido[4,5-d]pyrimidin-2-one (0.09 g, 0.09 mmol) (from Example 33b supra) and tetrabutylammonium fluoride (0.28 mL, 1.0 M solution in tetrahydrofuran, 0.28 mmol) (Aldrich) in tetrahydrofuran (5 mL) was heated at reflux for 3 hours. After cooling, it was concentrated under reduced pressure. The residue was purified by flash chromatography eluting with ethyl acetate-dichloromethane (5:95) to give 1-(cis-3,5-dihydroxy-cyclohexyl)-3-(4-methoxy-phenyl)-7-(4-methoxy-phenylamino)-3,4-dihydro-1H-pyrimido[4,5-d]pyrimidin-2-one. (Yield 18.0 mg, 39

Example 34a

4-Fluoro-3-methoxybenzoic acid methyl ester

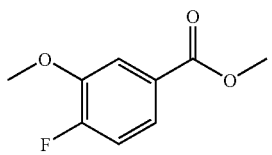

4-Fluoro-3-hydroxybenzoic acid (4.33 g, 27.7 mmol) (Aldrich) was dissolved in anhydrous dimethylformamide (Aldrich). Potassium carbonate (38.3 g, 277 mmol) and methyl iodide (8.6 mL, 138.5 mmol) (Aldrich) were successively added at room temperature and the mixture was stirred overnight. After filtration, the solution was washed with water and extracted with ethyl acetate. The layers were separated and the organic layer was successively washed with water, 1 N aqueous sodium hydroxide, water and brine. The organic layer was dried over anhydrous sodium sulfate and concentrated under reduced pressure to give 4-fluoro-3-methoxybenzoic acid methyl ester as a pale yellow oil that solidified upon standing. (Yield 4.72 g, 92%).

Example 34b

4-Fluoro-3-methoxybenzoic acid

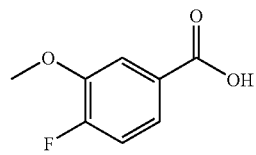

4-Fluoro-3-methoxybenzoic acid methyl ester (2.55 g, 13.85 mmol) (from Example 34a supra) was dissolved in a mixture of tetrahydrofuran (140 mL) and water (70 mL). Lithium hydroxide monohydrate (5.8 g, 138.5 mmol) was added and the mixture was heated at reflux for 3.5 hours. After quenching with 1 N aqueous hydrochloric acid (150 mL), the solution was extracted with dichloromethane. The phases were separated and the organic layer was dried over anhydrous sodium sulfate. Concentration under reduced pressure gave 4-fluoro-3-methoxybenzoic acid as an off-white solid. (Yield 2.26 g, 96%).

Example 34c (tert-Butoxy)-N-(4-fluoro-3-methoxyphenyl)carboxamide

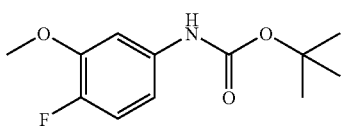

4-Fluoro-3-methoxybenzoic acid (1.00 g, 5.87 mmol) (from Example 34b supra) was dissolved in toluene (30 mL). Triethylamine (3.2 mL, 23.48 mmol) (Fisher), diphenyl phosphoryl azide (2.5 mL, 11.74 mmol) (Aldrich) and tert-butanol (6 mL) (Fisher) were successively added at room temperature. The reaction mixture was heated at reflux for 2 hours, then quenched at room temperature with 1 N aqueous hydrochloric acid (20 mL). The mixture was extracted with ethyl acetate and the layers were separated. The organic layer was washed with saturated aqueous sodium bicarbonate solution and brine, then dried over anhydrous sodium sulfate and filtered. Concentration under reduced pressure gave a yellow oil that was purified by flash chromatography (20% ethyl acetate in hexanes) to give (tert-butoxy)-N-(4-fluoro-3-methoxyphenyl)carboxamide as a white solid. (Yield 0.98 g, 70%).

Example 34d

4-Fluoro-3-methoxyphenylamine hydrochloric acid salt

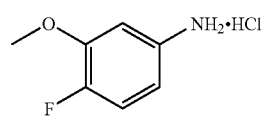

(tert-Butoxy)-N-(4-fluoro-3-methoxyphenyl)carboxamide (0.98 g, 4.06 mmol) (from Example 34c supra) was treated with 4 N hydrochloric acid in dioxane (20 mL) (Aldrich) overnight at room temperature. The resulting precipitate was collected by filtration and washed with dry ether to give 4-fluoro-3-methoxyphenylamine hydrochloric acid salt as a white, crystalline, solid. (Yield 512 mg, 71%).

Example 34e
1-[cis-3,5-Bis-(tert-butyl-diphenyl-silanyloxy)-cyclohexyl]-3-(4-methoxy-phenyl)-7-(4-fluoro-3-methoxy-phenylamino)-3,4-dihydro-1H-pyrimido[4,5-d]pyrimidin-2-one

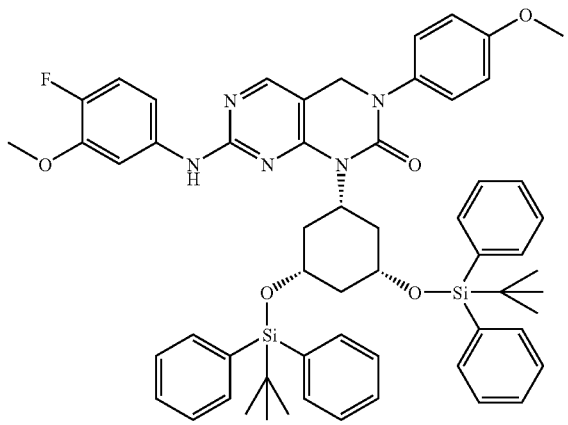

A solution of 1-[cis-3,5-bis-(tert-butyl-diphenyl-silanyloxy)-cyclohexyl]-7-chloro-3-(4-methoxy-phenyl)-3,4-dihydro-1H-pyrimido[4,5-d]pyrimidin-2-one (0.20 g, 0.23 mmol) (from Example 33a supra) and 4-fluoro-3-methoxy-phenylamine hydrochloride salt (51 mg, 0.29 mmol) (from Example 34d supra) in 2-propanol (4 mL) was placed in a microwave reactor (SmithSynthesizer®). The reaction mixture was heated at 160° C. for 10 minutes. After cooling, it was concentrated under reduced pressure. The residue was purified by flash chromatography eluting with ethyl acetate-hexanes (3:7 then 2:3) to give 1-[cis-3,5-bis-(tert-butyl-diphenyl-silanyloxy)-cyclohexyl]-3-(4-methoxy-phenyl)-7-(4-fluoro-3-methoxy-phenylamino)-3,4-dihydro-1H-pyrimido[4,5-d]pyrimidin-2-one. (Yield 0.08 g, 35

Example 34f 1-(cis-3,5-Dihydroxy-cyclohexyl)-3-(4-methoxy-phenyl)-7-(4-fluoro-3-methoxy-phenylamino)-3,4-dihydro-1H-pyrimido[4,5-d]pyrimidin-2-one

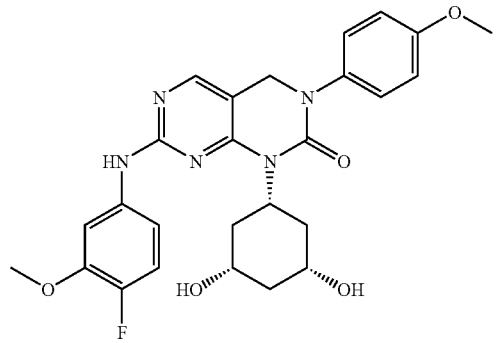

A solution of 1-[cis-3,5-bis-(tert-butyl-diphenyl-silanyloxy)-cyclohexyl]-3-(4-methoxy-phenyl)-7-(4-fluoro-3-methoxy-phenylamino)-3,4-dihydro-1H-pyrimido[4,5-d]pyrimidin-2-one (0.08 g, 0.08 mmol) (from Example 34e supra) and tetrabutylammonium fluoride (0.24 mL, 1.0 M solution in tetrahydrofuran, 0.24 mmol) (Aldrich) in tetrahydrofuran (5 mL) was heated at reflux for 3 hours. After cooling, it was concentrated under reduced pressure. The residue was purified by flash chromatography eluting with ethyl acetate-dichloromethane (5:95) to give 1-(cis-3,5-dihydroxy-cyclohexyl)-3-(4-methoxy-phenyl)-7-(4-fluoro-3-methoxy-phenylamino)-3,4-dihydro-1H-pyrimido[4,5-d]pyrimidin-2-one. (Yield 18.0 mg, 78%).

Example 35a

1-[cis-3,5-Bis-(tert-butyl-diphenyl-silanyloxy)-cyclohexyl]-3-(4-methoxy-phenyl)-7-phenylamino-3,4-dihydro-1H-pyrimido[4,5-d]pyrimidin-2-one

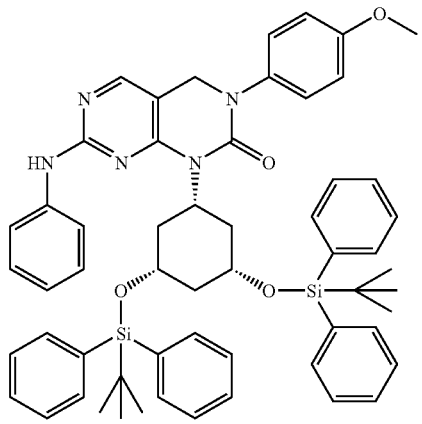

A mixture of 1-[cis-3,5-bis-(tert-butyl-diphenyl-silanyloxy)-cyclohexyl]-7-chloro-3-(4-methoxy-phenyl)-3,4-dihydro-1H-pyrimido[4,5-d]pyrimidin-2-one (0.20 g, 0.23 mmol) (from Example 33a supra) and aniline (0.03 mL, 0.29 mmol) (Aldrich) in 2-propanol (4 mL) was placed in a microwave reactor (SmithSynthesizer®). The reaction mixture was heated at 160° C. for 10 minutes. After cooling, it was concentrated under reduced pressure. The residue was purified by flash chromatography eluting with ethyl acetate-hexanes (3:7 then 2:3) to give 1-[cis-3,5-bis-(tert-butyl-diphenyl-silanyloxy)-cyclohexyl]-3-(4-methoxy-phenyl)-7-phenylamino-3,4-dihydro-1H-pyrimido[4,5-d]pyrimidin-2-one. (Yield 0.14 g, 64%).

Example 35b 1-(cis-3,5-Dihydroxy-cyclohexyl)-3-(4-methoxy-phenyl)-7-phenylamino-3,4-dihydro-1H-pyrimido[4,5-d]pyrimidin-2-one

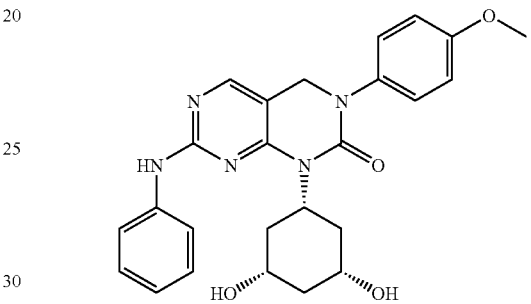

A solution of 1-[cis-3,5-bis-(tert-butyl-diphenyl-silanyloxy)-cyclohexyl]-3-(4-methoxy-phenyl)-7-phenylamino-3,4-dihydro-1H-pyrimido[4,5-d]pyrimidin-2-one (0.14 g, 0.15 mmol) (from Example 35a supra) and tetrabutylammonium fluoride (0.44 mL, 1.0 M solution in tetrahydrofuran, 0.44 mmol) (Aldrich) in tetrahydrofuran (5 mL) was heated at reflux for 3 hours. After cooling, it was concentrated under reduced pressure. The residue was purified by flash chromatography eluting with ethyl acetate-edichloromethane (5:95) to give 1-(cis-3,5-dihydroxy-cyclohexyl)-3-(4-methoxy-phenyl)-7-phenylamino-3,4-dihydro-1H-pyrimido[4,5-d]pyrimidin-2-one. (Yield 42.0 mg, 61%).

Example 36a

1-[cis-3,5-Bis-(tert-butyl-diphenyl-silanyloxy)-cyclohexyl]-3-(2-fluoro-4-methoxy-phenyl)-7-phenylamino-3,4-dihydro-1H-pyrimido[4,5-d]pyrimidin-2-one

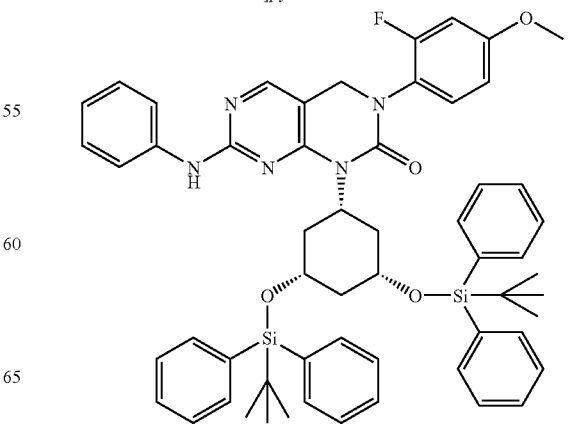

A mixture of 1-[cis-3,5-bis-(tert-butyl-diphenyl-silanyloxy)-cyclohexyl]-7-chloro-3-(2-fluoro-4-methoxy-phenyl)-3,4-dihydro-1H-pyrimido[4,5-d]pyrimidin-2-one (0.21 g, 0.23 mmol) (from Example 32d supra) and aniline (0.03 mL, 0.30 mmol) (Aldrich) in 2-propanol (4 mL) was placed in a microwave reactor (SmithSynthesizer®). The reaction mixture was heated at 160° C. for 10 minutes. After cooling, it was concentrated under reduced pressure. The residue was purified by flash chromatography eluting with ethyl acetate-dichloromethane (5:95) to give 1-[cis-3,5-bis-(tert-butyl-diphenyl-silanyloxy)-cyclohexyl]-3-(2-fluoro-4-methoxy-phenyl)-7-phenylamino-3,4-dihydro-1H-pyrimido[4,5-d]pyrimidin-2-one. (Yield 0.21 g, 35%).

Example 36b 1-(cis-3,5-Dihydroxy-cyclohexyl)-3-(2-fluoro-4-methoxy-phenyl)-7-phenylamino-3,4-dihydro-1H-pyrimido[4,5-d]pyrimidin-2-one

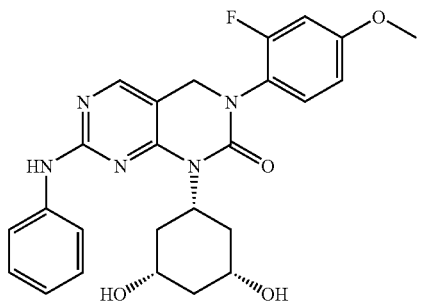

A solution of 1-[cis-3,5-bis-(tert-butyl-diphenyl-silanyloxy)-cyclohexyl]-3-(2-fluoro-4-methoxy-phenyl)-7-phenylamino-3,4-dihydro-1H-pyrimido[4,5-d]pyrimidin-2-one (0.21 g, 0.22 mmol) (from Example 36a supra) and tetrabutylammonium fluoride (0.66 mL, 1.0 M solution in tetrahydrofuran, 0.66 mmol) (Aldrich) in tetrahydrofuran (5 mL) was heated at reflux for 3 hours. After cooling, it was concentrated under reduced pressure. The residue was purified by flash chromatography eluting with ethyl acetate-dichloromethane (5:95) to give 1-(cis-3,5-dihydroxy-cyclohexyl)-3-(2-fluoro-4-methoxy-phenyl)-7-phenylamino-3,4-dihydro-1H-pyrimido[4,5-d]pyrimidin-2-one. (Yield 82.0 mg, 78%)

Example 37a

1-[cis-3,5-Bis-(tert-butyl-diphenyl-silanyloxy)-cyclohexyl]-3-(2-fluoro-4-methoxy-phenyl)-7-(4-fluoro-3-methoxy-phenylamino)-3,4-dihydro-1H-pyrimido[4,5-d]pyrimidin-2-one

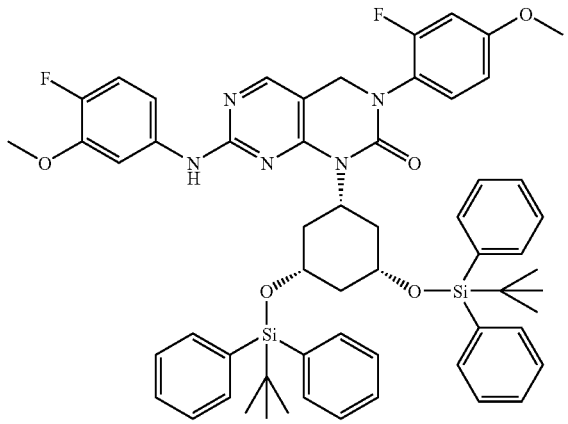

A mixture of 1-[cis-3,5-bis-(tert-butyl-diphenyl-silanyloxy)-cyclohexyl]-7-chloro-3-(2-fluoro-4-methoxy-phenyl)-3,4-dihydro-1H-pyrimido[4,5-d]pyrimidin-2-one (0.22 g, 0.24 mmol) (from Example 32d supra) and 4-fluoro-3-methoxy-phenylamine hydrochloric acid salt (56.3 mg, 0.32 mmol) (from Example 34d supra) in 2-propanol (4 mL) was placed in a microwave reactor (SmithSynthesizer®). The reaction mixture was heated at 160° C. for 10 minutes. After cooling, it was concentrated under reduced pressure. The residue was purified by flash chromatography eluting with ethyl acetate-hexanes (3:7 then 2:3) to give 1-[cis-3,5-bis-(tert-butyl-diphenyl-silanyloxy)-cyclohexyl]-3-(2-fluoro-4-methoxy-phenyl)-7-(4-fluoro-3-methoxy-phenylamino)-3,4-dihydro-1H-pyrimido[4,5-d]pyrimidin-2-one. (Yield 0.15 g, 63%).

Example 37b 1-(cis-3,5-Dihydroxy-cyclohexyl)-3-(2-fluoro-4-methoxy-phenyl)-7-(4-fluoro-3-methoxyphenylamino)-3,4-dihydro-1H-pyrimido[4,5-d]pyrimidin-2-one

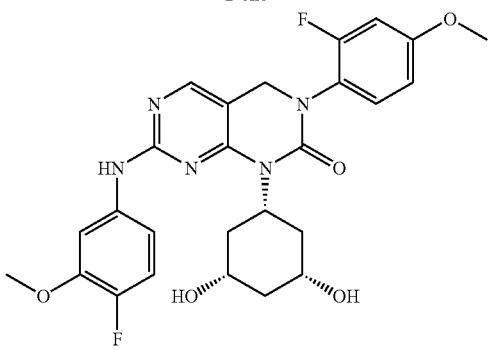

A solution of 1-[cis-3,5-bis-(tert-butyl-diphenyl-silanyloxy)-cyclohexyl]-3-(2-fluoro-4-methoxy-phenyl)-7-(4-fluoro-3-methoxy-phenylamino)-3,4-dihydro-1H-pyrimido[4,5-d]pyrimidin-2-one (0.15 g, 0.15 mmol) (from Example 37a supra) and tetrabutylammonium fluoride (0.45 mL, 1.0 M solution in tetrahydrofuran, 0.45 mmol) (Aldrich) in tetrahydrofuran (5 mL) was heated at reflux for 3 hours. After cooling, it was concentrated under reduced pressure. The residue was purified by flash chromatography eluting with ethyl acetate-dichloromethane (5:95) to give 1-(cis-3,5-dihydroxy-cyclohexyl)-3-(2-fluoro-4-methoxy-phenyl)-7-(4-fluoro-3-methoxyphenylamino)-3,4-dihydro-1H-pyrimido[4,5-d]pyrimidin-2-one. (Yield 35.0 mg, 44%).

Example 38a (R)-2-(tert-Butyl-dimethyl-silanyloxy)-1-methyl-ethylamine

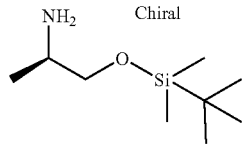

D-Alaninol hydrochloride (500 mg, 6.66 mmol) (Aldrich) was dissolved in anhydrous dimethylformamide (10 mL) (Aldrich). Imidazole (544 mg, 8 mmol) (Aldrich) and tert-butyldimethylsilyl chloride (1.05 g, 7 mmol) (Aldrich) were successively added at room temperature. This mixture was stirred at room temperature for 2 hours, quenched with a solution of water-saturated aqueous sodium bicarbonate solution (5:1, 15 mL) and extracted with ethyl acetate. The organic layer was washed with water and brine, dried over sodium sulfate, and concentrated under reduce pressure to yield (R)-2-(tert-butyl-dimethyl-silanyloxy)-1-methyl-ethylamine as a colorless oil. (Yield 852 mg, 68%).

Example 38b (R)-[2-(tert-Butyl-dimethyl-silanyloxy)-1-methyl-ethyl]-carbamic acid 4-nitro-phenyl ester

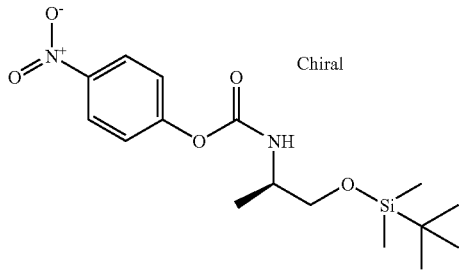

A mixture of (R)-2-(tert-butyl-dimethyl-silanyloxy)-1-methyl-ethylamine (693 mg, 3,66 mmol) (from Example 38a supra) and triethylamine (0.77 mL, 5.5 mmol) (Allied Signal) in dichloromethane was treated with 4-nitrophenyl chloroformate (885 mg, 4.39 mmol) (Aldrich) at room temperature for 30 minutes. The reaction was quenched with 1 N aqueous hydrochloric acid and then extracted with ethyl acetate. The combined organic layers were washed with saturated aqueous sodium bicarbonate solution followed with brine, dried over anhydrous sodium sulfate, filtered and concentrated under reduced pressure. The crude product was purified by flash chromatography (15% ethyl acetate in hexanes) to give (R)-[2-(tert-butyl-dimethyl-silanyloxy)-1-methyl-ethyl]-carbamic acid 4-nitro-phenyl ester as a colorless oil that solidified upon standing. (Yield 0.49 g, 38%).

Example 38c (2,4-Dichloro-pyrimidin-5-ylmethyl)-(4-ethyl-phenyl)-amine

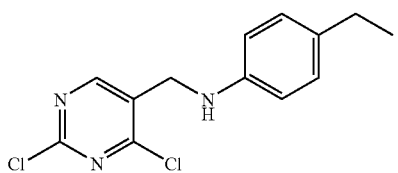

A heterogeneous mixture of 2,4-dichloro-5-(iodomethyl) pyrimidine (31.07 g, 107.3 mmol) (from Example 1c supra) and potassium carbonate (74 g, 536.5 mmol) in acetone (535 mL) was treated with 4-ethylaniline (13.3 mL, 107.3 mmol) (Aldrich). The mixture was stirred at room temperature overnight, then diluted with water (500 mL) and extracted with ethyl acetate. The combined organic layers were successively washed with 1 N aqueous hydrochloric acid, saturated aqueous sodium bicarbonate solution and brine, then dried over anhydrous sodium sulfate, filtered and concentrated under reduce pressure. The crude mixture was purified by flash chromatography (20% ethyl acetate in hexanes) to give (2,4-dichloro-pyrimidin-5-yl-methyl)-(4-ethyl-phenyl)-amine as a beige solid. (Yield 21.4 g, 70%).

Example 38d (R)-3-[2-(tert-Butyl-dimethyl-silanyloxy)-1-methyl-ethyl]-1-(2,4-dichloro-pyrimidin-5-ylmethyl)-1-(4-ethyl-phenyl)-urea

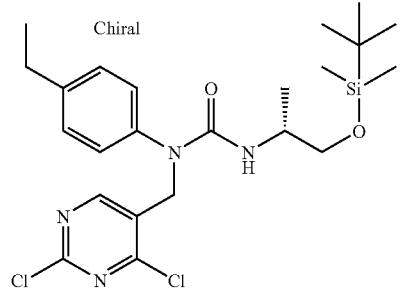

A solution of (2,4-dichloro-pyrimidin-5-yl-methyl)-(4-ethyl-phenyl)amine (620 mg, 2.19 mmol) (from Example 38c supra), (R)-[2-(tert-butyl-dimethyl-silanyloxy)-1-methyl-ethyl]-carbamic acid 4-nitro-phenyl ester (778 mg, 2.19 mmol) (from Example 38b supra) and triethylamine (0.93 mL, 6.6 mmol) (Allied Signal) in toluene (20 mL) was heated at reflux for 48 hours. The reaction mixture was quenched at room temperature with 1 N aqueous hydrochloric acid then extracted with ethyl acetate. The combined organic layers were successively washed with 1 N aqueous sodium hydroxide solution and brine, then dried over anhydrous sodium sulfate, filtered and concentrated under reduced pressure. The residue was purified by flash chromatography (30% ethyl acetate in hexanes) to give (R)-3-[2-(tert-butyl-dimethyl-silanyloxy)-1-methyl-ethyl]-1-(2,4-dichloro-pyrimidin-5-yl-methyl)-1-(4-ethyl-phenyl)-urea. (Yield 383 mg, 36%).

Example 38e (R)-1-[2-(tert-Butyl-dimethyl-silanyloxy)-1-methyl-ethyl]-7-chloro-3-(4-ethyl-phenyl)-3,4-dihydro-1H-pyrimido[4,5-d]pyrimidin-2-one

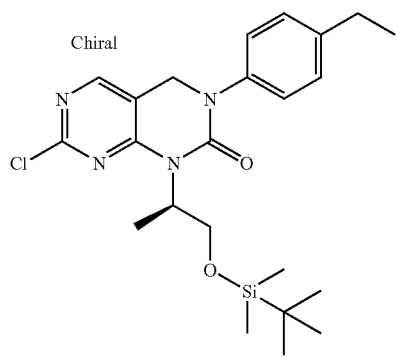

A solution of (R)-3-[2-(tert-butyl-dimethyl-silanyloxy)-1-methyl-ethyl]-1-(2,4-dichloro-pyrimidin-5-yl-methyl)-1-(4-ethyl-phenyl)-urea (380 mg, 0.76 mmol) (from Example 38d supra) in tetrahydrofuran (10 mL) was treated at room temperature with potassium tert-butoxide (160 mg, 1.14 mmol) (Aldrich). The mixture was stirred at room temperature for 1.5 hours. The reaction mixture was quenched with saturated aqueous sodium bicarbonate solution and extracted with ethyl acetate. The combined organic layers were washed with brine, dried over anhydrous sodium sulfate, filtered and concentrated under reduced pressure. The residue (395 mg, yellow oil) was purified by flash chromatography to give (R)-1-[2-(tert-butyl-dimethyl-silanyloxy)-1-methyl-ethyl]-7-chloro-3-(4-ethyl-phenyl)-3,4-dihydro-1H-pyrimido[4,5-d]pyrimidin-2-one as a colorless oil. (Yield 102 mg, 30%).

Example 38f (R)-1-[2-(tert-Butyl-dimethyl-silanyloxy)-1-methyl-ethyl]-3-(4-ethyl-phenyl)-7-(4-fluoro-phenylamino)-3,4-dihydro-1H-pyrimido[4,5-d]pyrimidin-2-one

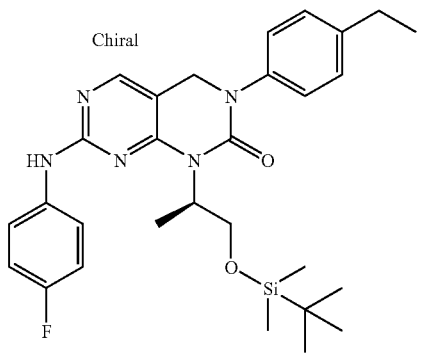

(R)-1-[2-(tert-Butyl-dimethyl-silanyloxy)-1-methyl-ethyl]-7-chloro-3-(4-ethyl-phenyl)-3,4-dihydro-1H-pyrimido[4,5-d]pyrimidin-2-one (100 mg, 0.21 mmol) (from Example 38e supra) was suspended in 2-propanol (2 mL) (Fisher). 4-Fluoroaniline (0.03 mL, 0.32 mmol) (Aldrich) was added and the mixture was heated to 160° C. in a microwave synthesizer (SmithSynthesizer™) for 30 minutes. After cooling to room temperature, the heterogeneous reaction mixture was diluted with dichloromethane. The resulting solution was washed with 1 N aqueous hydrochloric acid. The layers were separated and the organic phase was dried over anhydrous sodium sulfate, filtered and then concentrated under reduce pressure to give (R)-1-[2-(tert-butyl-dimethyl-silanyloxy)-1-methyl-ethyl]-3-(4-ethyl-phenyl)-7-(4-fluoro-phenylamino)-3,4-dihydro-1H-pyrimido[4,5-d]pyrimidin-2-one as a pale yellow solid. (Yield 107 mg, 91%).

Example 38g (R)-3-(4-Ethyl-phenyl)-7-(4-fluoro-phenylamino)-1-(2-hydroxy-1-methyl-ethyl)-3,4-dihydro-1H-pyrimido[4,5-d]pyrimidin-2-one

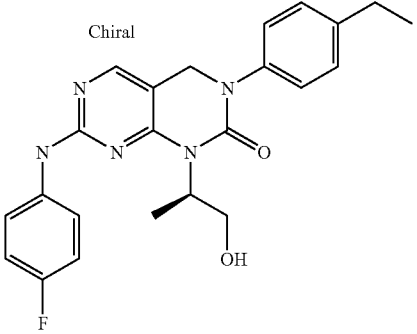

(R)-1-[2-(tert-Butyl-dimethyl-silanyloxy)-1-methyl-ethyl]-3-(4-ethyl-phenyl)-7-(4-fluoro-phenylamino)-3,4-dihydro-1H-pyrimido[4,5-d]pyrimidin-2-one (100 mg, 0.18 mmol) (from Example 38f supra) in pyridine (1.5 mL) (Fisher) was treated at room temperature with hydrogen fluoride-pyridine (0.6 mL) (Aldrich) for 15 minutes. The reaction mixture was quenched with 1 N aqueous hydrochloric acid at 0° C., then extracted with ethyl acetate. The organic layer was dried over anhydrous sodium sulfate, filtered and concentrated under reduced pressure. The residue was purified by flash chromatography (50% ethyl acetate in hexanes) to give (R)-3-(4-ethyl-phenyl)-7-(4-fluoro-phenylamino)-1-(2-hydroxy-1-methyl-ethyl)-3,4-dihydro-1H-pyrimido[4,5-d]pyrimidin-2-one as a colorless viscous oil. (Yield 45 mg, 61%).

Example 39a (±)-(trans-3-(tert-Butyl-dimethyl-silanyloxy)-cyclopentyl]-{2-chloro-5-[(4-ethyl-phenylamino)-methyl]-pyrimidin-4-yl}-amine

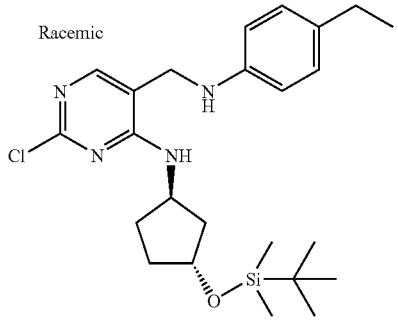

(2,4-Dichloro-pyrimidin-5-yl-methyl)-(4-ethyl-phenyl)-amine (200 mg, 0.71 mmol) (from Example 38c supra) was dissolved in hot n-butanol (2 mL) (Aldrich). After cooling to room temperature, triethylamine (0.20 mL, 0.92 mmol) (Allied Signal) and (±)-trans-3-(tert-butyl-dimethyl-silanyloxy)-cyclopentylamine (198 mg, 0.91 mmol) (from Example 9c supra) were successively added and the mixture was stirred at room temperature for 18 hours. The mixture was concentrated under reduced pressure and purified by flash chromatography (20% ethyl acetate in hexanes) to give (±)-[trans-3-(tert-butyl-dimethyl-silanyloxy)-cyclopentyl]-

{2-chloro-5-[(4-ethyl-phenylamino)-methyl]-pyrimidin-4-yl}-amine as a viscous oil. (Yield 272 mg, 84%).

Example 39b (±)-1-[trans-3-(tert-Butyl-dimethyl-silanyloxy)-cyclopentyl]-7-chloro-3-(4-ethyl-phenyl)-3,4-dihydro-1H-pyrimido[4,5-d]pyrimidin-2-one Racemic

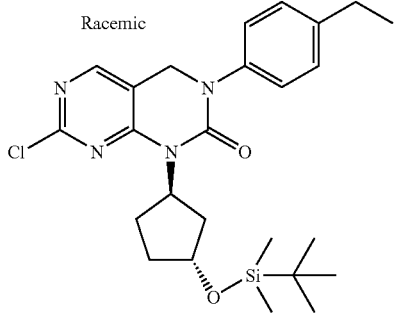

A mixture of (±)-[trans-3-(tert-butyl-dimethyl-silanyloxy)-cyclopentyl]-{2-chloro-5-[(4-ethyl-phenylamino)-methyl]-pyrimidin-4-yl}-amine (270 mg, 0.58 mmol) (from Example 39a supra) and triethylamine (0.25 mL, 1.76 mmol) (Allied Signal) in dichloromethane (6 mL) was cooled to 0° C. A 20% phosgene in toluene solution (0.32 mL, 0.61 mmol) (Fluka) was added dropwise and the mixture was stirred at 0° C. for 1 hour. The mixture was allowed to warm up to room temperature and 4-(dimethylamino)pyridine (15 mg, 0.12 mmol) (Aldrich) was added. The reaction was stirred at room temperature overnight, heated at reflux for 4 hours, and then concentrated to dryness. The yellow residue was purified by flash chromatography (20% ethyl acetate in hexanes) to give (±)-1-[trans-3-(tert-butyl-dimethyl-silanyloxy)-cyclopentyl]-7-chloro-3-(4-ethyl-phenyl)-3,4-dihydro-1H-pyrimido[4,5-d]pyrimidin-2-one. (Yield 213 mg, 75%).

Example 39c (±)-1-[trans-3-(tert-Butyl-dimethyl-silanyloxy)-cyclopentyl]-3-(4-ethyl-phenyl)-7-(4-fluoro-phenylamino)-3,4-dihydro-1H-pyrimido[4,5-d]pyrimidin-2-one Racemic

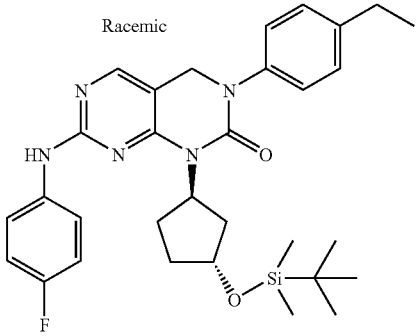

(±)-1-[trans-3-(tert-Butyl-dimethyl-silanyloxy)-cyclopentyl]-7-chloro-3-(4-ethyl-phenyl)-3,4-dihydro-1H-pyrimido[4,5-d]pyrimidin-2-one (125 mg, 0.25 mmol) (from Example 39b supra) was suspended in 2-propanol (3 mL) (Fisher). 4-Fluoroaniline (0.036 mL, 0.38 mmol) (Aldrich) and p-toluenesulfonic acid mono-hydrate (12.5 mg, 0.05 mmol) (Aldrich) were added and the mixture was heated to 160° C. in a microwave synthesizer (SmithSynthesizer®) for 30 minutes. After cooling to room temperature, the heterogeneous reaction mixture was diluted with dichloromethane. The resulting solution was washed with 1 N aqueous hydrochloric acid. The layers were separated and the organic phase was dried over anhydrous sodium sulfate, filtered and then concentrated under reduce pressure to give (±)-1-[trans-3-(tert-butyl-dimethyl-silanyloxy)-cyclopentyl]-3-(4-ethyl-phenyl)-7-(4-fluoro-phenylamino)-3,4-dihydro-1H-pyrimido[4,5-d]pyrimidin-2-one as a pale green solid. (Yield 123 mg, 85%).

Example 39d (±)-3-(4-Ethyl-phenyl)-7-(4-fluoro-phenylamino)-1-(trans-3-hydroxy-cyclopentyl)-3,4-dihydro-1H-pyrimido[4,5-d]pyrimidin-2-one Racemic

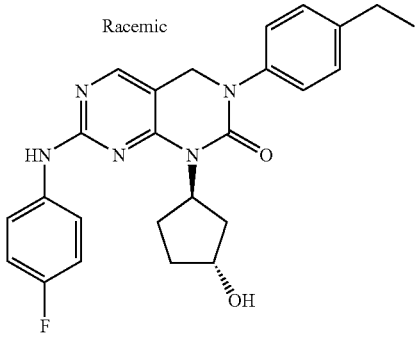

A solution of (±)-1-[trans-3-(tert-butyl-dimethyl-silanyloxy)-cyclopentyl]-3-(4-ethyl-phenyl)-7-(4-fluoro-phenylamino)-3,4-dihydro-1H-pyrimido[4,5-d]pyrimidin-2-one (47 mg, 0.08 mmol) in pyridine (1 mL) (Fisher) was treated at room temperature with hydrogen fluoride-pyridine (0.6 mL) (Aldrich) for 20 minutes. The reaction mixture was quenched with 1 N aqueous hydrochloric acid at 0° C., then extracted with ethyl acetate. The organic layer was dried over anhydrous sodium sulfate, filtered and concentrated under reduced pressure. The residue was purified by flash chromatography (50% ethyl acetate in hexanes) to give (±)-3-(4-ethyl-phenyl)-7-(4-fluoro-phenylamino)-1-(trans-3-hydroxy-cyclopentyl)-3,4-dihydro-1H-pyrimido[4,5-d]pyrimidin-2-one as a white solid. (Yield 32 mg, 87%).

Example 40

1-Cyclopropylmethyl-3-(4-methoxy-phenyl)-7-phenylamino-3,4-dihydro-1H-pyrimido[4,5-d]pyrimidin-2-one

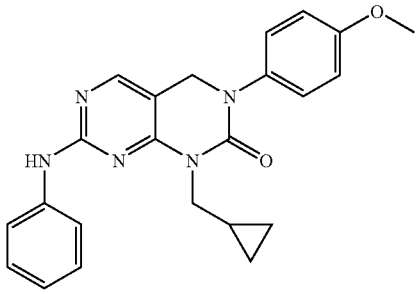

To a solution of [(2,4-dichloropyrimidin-5-yl)methyl](4-methoxy-phenyl)amine (198 mg, 0.7 mmol) (from Example 1d supra) in n-butanol (5 mL) was added cyclopropanemethylamine (0.12 mL, 1.4 mmol) (Aldrich) and N,N-diisopropylethylamine (10.13 mL) (Aldrich). The reaction mixture was stirred at room temperature overnight, and then quenched with water and extracted with ethyl acetate (3×50 mL). The combined organic extracts were successively washed with water (10 mL) and brine (10 mL), dried over anhydrous sodium sulfate, filtered, and concentrated under reduced pressure to give the crude mono chloride as a colorless oil (Yield 220 mg) which was used in the next step without further purification.

To a solution of crude mono chloride (220 mg) in dichloromethane (20 mL) at 0° C. was added triethylamine (0.3 mL, 2.1 mmol) (Aldrich) followed by addition of 20% solution of phosgene in toluene (0.5 mL, 0.98 mmol) (Fluka) dropwise. This mixture was stirred at room temperature for 15 minutes. The reaction mixture was then poured into ice-cold water (50 mL) and extracted with ethyl acetate (3×50 mL). The combined organic extracts were successively washed with water (10 mL) and brine (10 mL), dried over anhydrous sodium sulfate, filtered, and concentrated under reduced pressure to give the crude intermediate which was dissolved again in dichloromethane (5 mL) and heated under reflux in the presence of 4-(dimethylamino)pyridine (20 mg) (Aldrich) overnight. The reaction mixture was quenched with water and extracted with ethyl acetate (3×50 mL). The combined organic extracts were successively washed with water (10 mL) and brine (10 mL), dried over anhydrous sodium sulfate, filtered, and concentrated under reduced pressure to give the crude products which was then separated by preparative thin layer chromatography to give 7-chloro-1-cyclopropylmethyl-3-(4-methoxy-phenyl)-3,4-dihydro-1H-pyrimido[4,5-d]pyrimidine-2-one. (Yield 259 mg, 74.8%, 3 steps).

The mixture of 7-chloro-1-cyclopropylmethyl-3-(4-methoxy-phenyl)-3,4-dihydro-1H-pyrimido[4,5-d]pyrimidine-2-one (129 mg, 0.37 mmol) in aniline (1.0 mL) (Aldrich) was heated to 120° C. for 5.5 hours. After cooling, the reaction mixture was washed with hexanes (4×100 mL) and the crude product was purified by preparative thin layer chromatography to give 1-cyclopropylmethyl-3-(4-methoxy-phenyl)-7-phenylamino-3,4-dihydro-1H-pyrimido[4,5-d]pyrimidine-2-one as an off-white solid. (Yield 20.6 mg, 13.7%).

Antiproliferative Activity

The antiproliferative activity of the compounds of the invention is demonstrated below in Examples 41 and 42. These activities indicate that the compounds of the present invention are useful in treating cancer, in particular solid tumors such as breast, lung, prostate and colon tumors, more particularly breast and colon tumors.

Example 41

Kinase Assays

To determine inhibition of KDR, FGFR, EGFR, and PDGFR activity, kinase assays were conducted using an HTRF (Homogeneous Time Resolved Fluorescence) assay. This assay is described in A. J. Kolb et. al., Drug Discovery Today, 1998, 3(7), p 333.

Prior to kinase reaction, recombinant EEE-tagged KDR was activated in the presence of activation buffer (50 mM HEPES, pH 7.4, 1 mM DTT, 10% glycerol, 150 mM NaCl, 0.1 mM EDTA, 26 mM $MgCl_2$, and 4 mM ATP). The enzyme was incubated at 4° C. for 1 hour.

Kinase activity assays were performed in 96-well polypropylene plates (Falcon) with a total volume of 90 µL in each well. Each well contained 1 µM KDR substrate (Biotin-EEEEYFELVAKKKK), 1 nM activated KDR, and a test compound with one of 8 assay concentrations ranging from 100 µM to 128 pM (1:5 serial dilution). The kinase activity assay was done in the presence of 100 mM HEPES, pH 7.4, 1 mM DTT, 0.1 mM $Na_2VO_4$, 25 mM $MgCl_2$, 50 mM NaCl (from KDR stock solution), 1% DMSO (from compound), 0.3 mM ATP (at $K_m$ concentration) and 0.02% BSA. The reaction was incubated at 37° C. for 30 minutes. To stop the KDR reaction, 72 µL of reaction mixture was transferred into a STOP plate containing 18 µL of revelation buffer (20 mM EDTA, 50 mM HEPES, pH 7.4, 0.02% BSA, 10 nM Eu-labelled anti-pY antibody (final conc. 2 nM), and 100 nM streptavidin (final conc. 20 nM)). After mixing, 35 µL of solution was transferred into duplicate wells of a 384-well black plate (Costar), and read at 615/665 nm on a Wallac Victor 5 reader.

FGFR, EGFR, and PDGFR activity assays were carried out as described above for the KDR activity assay with the following differences. GST-tagged FGFR enzyme was activated at room temperature for 1 hour in the following activation buffer: 100 mM HEPES, pH 7.4, 50 mM NaCl, 20 mM $MgCl_2$, and 4 mM ATP. The kinase activity assay was performed with 1 µM substrate (Biotin-EEEEYFELV), 1.5 nM activated FGFR, and test compound in the presence of 100 mM HEPES, 1 mM DTT, 0.4 mM $MgCl_2$, 0.4 mM $MnCl_2$, 50 mM NaCl, 1% DMSO, 10 µM ATP ($K_m$=8.5 µM for FGFR), 0.1 mM $Na_2VO_4$, and 0.02% BSA, in a total volume of 90 µL. The rest of the assay was performed in the same manner as KDR assay.

The EGFR kinase activity assay was performed with 1 µM substrate (Biotin-EEEEYFELV), 1.5 nM EGFR, test compounds, 100 mM HEPES, pH 7.4, 1 mM DTT, 5 mM $MgCl_2$, 2 mM $MnCl_2$, 1% DMSO, 0.5 µM ATP ($K_m$ for EGFR), 0.1 mM $Na_2VO_4$, and 0.02% BSA. The rest of the assay was performed in the same manner as the KDR assay.

The PDGFR kinase activity assay was performed with 1 µM substrate (Biotin-EEEEYFELV), 1.0 nM PDGFR, test compounds, 100 mM HEPES, pH 7.4, 1 mM DTT, 5 mM $MgCl_2$, 2 mM $MnCl_2$, 1% DMSO, 2.3 µM ATP ($K_m$ for PDGFR), 0.1 mM $Na_2VO_4$, and 0.02% BSA. The rest of the assay was performed in the same manner as the KDR assay.

Compound $IC_{50}$ values were determined from duplicate sets of data, and calculated by using Excel and fitting data to equation $Y=[(a-b)/\{1+(X/c)^d\}+b$, where a and b are enzyme activity in the presence of no test inhibitor compound and an infinite amount of inhibitor test compound, respectively, c is the $IC_{50}$ and d is the hill constant of the compound response. The $IC_{50}$ value is the concentration of test compound that reduces by 50% the enzyme activity under the test conditions described.

The $IC_{50}$ values in the above-described enzyme inhibition assays for the compounds of the invention are as follows: KDR less than 0.50 µM; FGFR less than 2 µM.

Example 42

VEGF and FGF-stimulated HUVEC Proliferation Assays

The antiproliferative activity of test compounds of this invention in cell-based assays was evaluated by BrdU assay using the BrdU kit (Roche Biochemicals 1-647-229). Human umbilical vein endothelial cells (Clonetics CC-2519) were cultured in EGM-2 (Clonetics CC-3162)

medium and seeded at 10000 cells per well in a volume of 200 μL of EGM-2 (Clonetics CC-3162) media in a 96-well flat bottom plates (Costar 3595) overnight. After 24 hours of growth at 37° C. with 5% $CO_2$, the incubation media was removed slowly by aspiration and the content of each well was washed with 300 μL pre-warmed EBM-2 (Clonetics CC-3156) containing 50 μg per mL of gentamycin and 50 ng per mL of amphotericin-B (Clonetics CC4083). Subsequently, the remaining media was again aspirated and replaced with 160 μL per well of serum starvation media (EBM-2 supplemented with 1% heat inactivated FBS (Clonetics CC-4102), 50 μg per mL gentamycin and 50 ng per mL of amphotericin-B (Clonetics CC-4083), 10 units per mL of Wyeth-Ayerst heparin (NDC0641-0391-25), and 2 mM L-glutamine (GIBCO 25030-081). After serum starving the cells for 24 hours, 20 μL of test compound at 10× test concentration in serum starvation medium with 2.5% DMSO was added to the appropriate wells. The control wells contained 20 μL of serum starvation medium with 2.5% DMSO. Plates were returned to the incubator for 2 hours. After pre-incubating the cells with the test compounds for 2 hours, 20 μL of growth factors at 10× assay concentration diluted in serum starvation media, FGF at 50 ng per mL, or VEGF (R&D systems 293-VE) at 200 ng per mL were added. The final concentration of FGF in the assay was 5 ng per mL, and the final concentration of VEGF in the assays was 20 ng per mL. The growth factor free control wells had 20 μL per well of serum starvation media with the same amount of BSA as the wells with growth factors. The plates were returned to the incubator for an additional 22 hours.

BrdU ELISA

After 24 hour exposure to the test compounds, the cells were labeled with BrdU (Roche Biochemicals 1-647-229), by adding 20 μL per well of BrdU labeling reagent that has been diluted (1:100) in serum starvation medium. The plates were then returned to the incubator for 4 hours. The labeling medium was removed by draining the medium onto paper towels. The cells were fixed and DNA denatured by adding 200 μL of fixation/denaturation solution to each well and incubating at room temperature for 45 minutes. The fixation/denaturation solution was drained onto paper towels and to each well was added 100 μL of anti-BrdU-POD and the wells were incubated for 2 hours at room temperature. The antibody solution was removed and the wells were each washed 3–4 times with 300 μL PBS. 100 μL of the TMB substrate solution was added to each well and the wells were incubated at room temperature for 5–8 minutes. The reaction was then stopped by adding 100 μL per well of 1 M phosphoric acid. The plates were read at 450 nm with reference wavelength of 650 nm. The percent inhibition for each test compound was calculated by subtracting the absorbency of the blank (no cells) wells from all wells, then subtracting the division of the average absorbency of each test duplicate by the average of the controls from 1. The final product was then multiplied by 100 (% of inhibition=(1-average absorbency of test duplicate/average of control) 100). The $IC_{50}$ value is the concentration of test compound that inhibits by 50% BrdU labeling, and is a measure of inhibition of cell proliferation. The $IC_{50}$ is determined from the linear regression of a plot of the logarithm of the concentration versus percent inhibition.

The $IC_{50}$ values of VEGF and FGF-stimulated HUVEC proliferation assays for the compounds of the invention measured as described herein are as follows: HUVEC/VEFG less than 1.00 μM; HUVEC/bFGF less than 1.00 μM.

Example 43

Tablet Formulation

| Item | Ingredients | Mg/Tablet | | | | | |
|------|-------------|-----|-----|-----|-----|-----|-----|
| 1 | Compound A* | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |
| 4 | Povidone K30 | 5 | 5 | 6 | 12 | 24 | 36 |
| 5 | Magnesium Stearate | 1 | 1 | 1 | 3 | 6 | 9 |
| | Total Weight | 120 | 120 | 150 | 300 | 600 | 900 |

*Compound A represents a compound of the invention.

Manufacturing Procedure:
1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50° C.
4. Pass the granulation from Step 3 through a suitable milling equipment.
5. Add the Item 5 to the milled granulation Step 4 and mix for 3 minutes.
6. Compress the granulation from Step 5 on a suitable press.

Example 44

Capsule Formulation

| Item | Ingredients | mg/Capsule | | | | |
|------|-------------|-----|-----|-----|-----|-----|
| 1 | Compound A* | 5 | 25 | 100 | 250 | 500 |
| 2 | Anhydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

*Compound A represents a compound of the invention.

Manufacturing Procedure:
1. Mix Items 1, 2 and 3 in a suitable mixer for 15 minutes.
2. Add Items 4 & 5 and mix for 3 minutes.
3. Fill into a suitable capsule.

Example 45

Injection Solution/Emulsion Preparation

| Item | Ingredient | mg/mL |
|------|------------|-------|
| 1 | Compound A* | 1 mg |
| 2 | PEG 400 | 10–50 mg |
| 3 | Lecithin | 20–50 mg |
| 4 | Soy Oil | 1–5 mg |
| 5 | Glycerol | 8–12 mg |
| 6 | Water q.s. | 1 mL |

*Compound A represents a compound of the invention.

Manufacturing Procedure:
1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 μm filter and fill into vials.

Example 46

| | Injection Solution/Emulsion Preparation | |
|---|---|---|
| Item | Ingredient | mg/mL |
| 1 | Compound A* | 1 mg |
| 2 | Glycofurol | 10–50 mg |
| 3 | Lecithin | 20–50 mg |
| 4 | Soy Oil | 1–5 mg |
| 5 | Glycerol | 8–12 mg |
| 6 | Water | q.s. 1 mL |

*Compound A represents a compound of the invention.

Manufacturing Procedure:
1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 μm filter and fill into vials.

While the invention has been illustrated by reference to specific and preferred embodiments, those skilled in the art will understand that variations and modifications may be made through routine experimentation and practice of the invention. Thus, the invention is intended not to be limited by the foregoing description, but to be defined by the appended claims and their equivalents.

What is claimed is:
1. A compound of formula

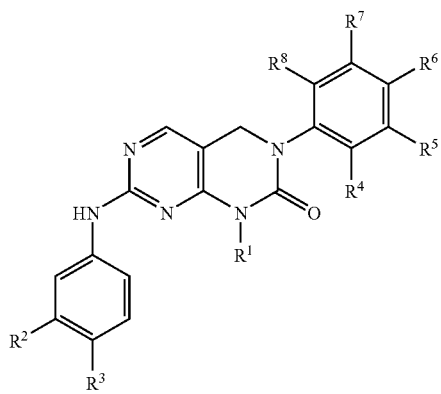

I wherein
$R^1$ is selected from the group consisting of
—H,
—$(CH_2)_n$-heterocycle,
-lower alkyl substituted by up to three groups selected from —$OR^9$, —$COR^{10}$, —$CO_2R^{10}$, —$CONR^{10}R^{11}$, —$SO_2NR^{10}R^{11}$, $SO_2R^{10}$ or —CN;
-alkyl,
-cycloalkyl,
-alkenyl, and
-alkynyl,
where n is 0, 1, 2, or 3, and the heterocycle, cycloalkyl, alkenyl, and alkynyl groups are each independently, optionally substituted by up to 3 groups selected from
—$OR^9$,
—$COR^{10}$,
—$CO_2R^{10}$,
—$CONR^{10}R^{11}$,
—$SO_2NR^{10}R^{11}$,
—$SO_2R^{10}$, and
—CN;
$R^2$ and $R^3$ are independently selected from the group consisting of
—H,
—$OR^9$,
-halogen,
—$COR^{10}$,
—$(CH_2)_n$-heterocycle,
-alkyl,
-cycloalkyl,
-alkenyl, and
-alkynyl,
where n is 0, 1, 2, or 3, and the heterocycle, alkyl, cycloalkyl, alkenyl, and alkynyl groups are each independently, optionally substituted by up to 3 groups selected from
—$OR^9$,
-halogen,
—$COR^{10}$, and
—$CO_2R^{10}$;
$R^4$, $R^5$, $R^6$, $R^7$ and $R^8$ are each independently selected from the group consisting of
—H,
-lower alkyl that optionally may be substituted by hydroxy or alkoxy,
—$OR^{12}$,
-halogen,
—$COR^{13}$, and
—$CO_2R^{13}$;
$R^9$ is selected from the group consisting of
—H,
—$COR^{10}$,
-lower alkyl that optionally may be substituted by hydroxy or alkoxy,
-cycloalkyl that optionally may be substituted by hydroxy, alkoxy, and lower alkyl, and
-heterocycle that optionally may be substituted by hydroxy, alkoxy or lower alkyl;
$R^{10}$ and $R^{11}$ are each independently selected from the group consisting of
—H,
-lower alkyl that optionally may be substituted by hydroxy or alkoxy,
-cycloalkyl that optionally may be substituted by hydroxy, alkoxy or lower alkyl, and
-heterocycle that optionally may be substituted by hydroxy, alkoxy or lower alkyl;
$R^{12}$ is selected from the group consisting of —H, lower alkyl and —$COR^{13}$; and
$R^{13}$ is selected from the group consisting of —H and lower alkyl;
or the pharmaceutically acceptable salts thereof.

2. The compound of claim 1 wherein $R^1$ is selected from cycloalkyl; cycloaklyl substituted by —OH; heterocycle; and lower alkyl substituted by —OH.

3. The compound of claim 1 wherein $R^2$ is —H or —OCH$_3$.

4. The compound of claim 1 wherein $R^3$ is —H, F, or —OCH$_3$.

5. The compound of claim 1 wherein $R^2$ and $R^3$ are both —H.

6. The compound of claim 1 wherein $R^4$, $R^5$ and $R^7$ are —H.

7. The compound of claim 1 wherein $R^6$ is halogen or $OR^{12}$.

8. The compound of claim 7 wherein $R^6$ is —OCH$_3$.

9. The compound of claim 1 wherein $R^8$ is —H or —F.

10. The compound of claim 1 wherein $R^9$ is —H, lower alkyl, or lower alkyl substituted by hydroxy.

11. The compound of claim 10 wherein $R^9$ is —H.

12. The compound of claim 1 wherein $R^{10}$ is —H, lower alkyl, or lower alkyl substituted by hydroxy.

13. The compound of claim 12 wherein $R^{10}$ is —H.

14. The compound of claim 1 wherein $R^{11}$ is —H, lower alkyl, or lower alkyl substituted by hydroxy.

15. The compound of claim 14 wherein $R^{11}$ is —H.

16. The compound of claim 1 wherein $R^{12}$ is —H or lower alkyl.

17. The compound of claim 16 wherein $R^{12}$ is —H.

18. The compound of claim 1 wherein $R^{13}$ is —H or lower alkyl.

19. The compound of claim 18 wherein $R^{13}$ is —H.

20. A compound selected from the group:
1-Cyclohexyl-3-(4-methoxy-phenyl)-7-phenylamino-3,4-dihydro-1H-pyrimido[4,5-d]pyrimidin-2-one,
3-(4-Methoxy-phenyl)-7-phenylamino-1-piperidin-4-yl-3,4-dihydro-1H-pyrimido[4,5-d]pyrimidin-2-one,
1-(trans-4-Hydroxy-cyclohexyl)-3-(4-methoxy-phenyl)-7-phenylamino-3,4-dihydro-1H-pyrimido[4,5-d]pyrimidin-2-one,
3-(4-Methoxy-phenyl)-7-phenylamino-1-piperidin-3-yl-3,4-dihydro-1H-pyrimido[4,5-d]pyrimidin-2-one,
1-Cyclopentyl-3-(4-methoxy-phenyl)-7-phenylamino-3,4-dihydro-1H-pyrimido[4,5-d]pyrimidin-2-one,
1-(1,1-Dioxo-tetrahydro-1l6-thiophen-3-yl)-3-(4-methoxy-phenyl)-7-phenylamino-3,4-dihydro-1H-pyrimido[4,5-d]pyrimidin-2-one,
3-[3-(4-Methoxy-phenyl)-2-oxo-7-phenylamino-3,4-dihydro-2H-pyrimido[4,5-d]pyrimidin-1-yl]-piperidine-1-carbaldehyde,
3-(4-Methoxy-phenyl)-7-phenylamino-1-(tetrahydro-pyran-4-yl)-3,4-dihydro-1H-pyrimido[4,5-d]pyrimidin-2-one,
(±)-1-(trans-3-Hydroxy-cyclopentyl)-3-(4-methoxy-phenyl)-7-phenylamino-3,4-dihydro-1H-pyrimido[4,5-d]pyrimidin-2-one, and
(±)-cis-1-(3-Hydroxy-cyclopentyl)-3-(4-methoxy-phenyl)-7-phenylamino-3,4-dihydro-1H-pyrimido[4,5-d]pyrimidin-2-one.

21. A compound selected from the group:
(R)-3-(4-Methoxy-phenyl)-7-phenylamino-1-(tetrahydro-furan-3-yl)-3,4-dihydro-1H-pyrimido[4,5-d]pyrimidin-2-one,
(R)-3-(4-Methoxy-phenyl)-7-phenylamino-1-pyrrolidin-3-yl-3,4-dihydro-1H-pyrimido[4,5-d]pyrimidin-2-one,
(±)-7-(4-Fluoro-phenylamino)-1-(trans-3-hydroxy-cyclopentyl)-3-(4-methoxy-phenyl)-3,4-dihydro-1H-pyrimido[4,5-d]pyrimidin-2-one,
(±)-3-(2-Fluoro-4-methoxy-phenyl)-1-(trans-3-hydroxy-cyclopentyl)-7-phenylamino-3,4-dihydro-1H-pyrimido[4,5-d]pyrimidin-2-one,
(S)-(+)-1-(2-Hydroxy-1-methyl-ethyl)-3-(4-methoxy-phenyl)-7-phenylamino-3,4-dihydro-1H-pyrimido[4,5-d]pyrimidin-2-one,
(S)-(+)-7-(4-Fluoro-phenylamino)-1-(2-hydroxy-1-methyl-ethyl)-3-(4-methoxy-phenyl)-3,4-dihydro-1H-pyrimido[4,5-d]pyrimidin-2-one,
3-(2-Fluoro-4-methoxy-phenyl)-1-(trans-4-hydroxy-cyclohexyl)-7-(4-methoxy-phenylamino)-3,4-dihydro-1H-pyrimido[4,5-d]pyrimidin-2-one,
3-(2-Fluoro-4-methoxy-phenyl)-1-(trans-4-hydroxy-cyclohexyl)-7-(3,4-dimethoxy-phenylamino)-3,4-dihydro-1H-pyrimido[4,5-d]pyrimidin-2-one,
3-(4-Methoxy-phenyl)-1-(trans-4-hydroxy-cyclohexyl)-7-(3,4-dimethoxy-phenylamino)-3 ,4-dihydro-1H-pyrimido[4,5-d]pyrimidin-2-one,
3-(4-Methoxy-phenyl)-1-(trans-4-hydroxy-cyclohexyl)-7-(4-methoxy-phenylamino)-3,4-dihydro-1H-pyrimido[4,5-d]pyrimidin-2-one, and
(S)-(+)-3-(2-Fluoro-4-methoxy-phenyl)-7-(4-fluoro-phenylamino)-1-(2-hydroxy-1-methyl-ethyl)-3,4-dihydro-1H-pyrimido[4,5-d]pyrimidin-2-one.

22. A compound selected from the group:
(S)-(+)-3-(2-Fluoro-4-methoxy-phenyl)-1-(2-hydroxy-1-methyl-ethyl)-7-(4-methoxy-phenylamino)-3,4-dihydro-1H-pyrimido[4,5-d]pyrimidin-2-one,
(R)-(−)-1-(2-Hydroxy-1-methyl-ethyl)-3-(4-methoxy-phenyl)-7-phenylamino-3,4-dihydro-1H-pyrimido[4,5-d]pyrimidin-2-one,
3-(4-Methoxy-phenyl)-1-methyl-7-phenylamino-3,4-dihydro-1H-pyrimido[4,5-d]pyrimidine-2-one,
1-(2-methoxy-ethoxymethyl)-3-(4-methoxy-phenyl)-7-phenylamino-3,4-dihydro-1H-pyrimido[4,5-d]pyrimidin-2-one,
3-[-3-(4-Methoxy-phenyl)-2-oxo-7-phenylamino-3,4-dihydro-1H-pyrimido[4,5-d]pyrimidin-1-yl]-propionitrile,
(+)-(1R,3R)-1-(3-Hydroxy-cyclopentyl)-3-(4-methoxy-phenyl)-7-phenylamino-3,4-dihydro-1H-pyrimido[4,5-d]pyrimidin-2-one,
(R)-1-(2-Hydroxy-propyl)-3-(4-methoxy-phenyl)-7-phenylamino-3,4-dihydro-1H-pyrimido[4,5-d]pyrimidin-2-one,
(−)-(1S,3S)-1-(3-Hydroxy-cyclopentyl)-3-(4-methoxy-phenyl)-7-phenylamino-3,4-dihydro-1H-pyrimido[4,5-d]pyrimidin-2-one,
3-[-3-(4-Methoxy-phenyl)-2-oxo-7-phenylamino-3,4-dihydro-1H-pyrimido[4,5-d]pyrimidin-1-yl]-propionamide, and
(S)-(+)-1-(2-Hydroxy-propyl)-3-(4-methoxy-phenyl)-7-phenylamino-3,4-dihydro-1H-pyrimido[4,5-d]pyrimidin-2-one.

23. A compound selected from the group:
1-(cis-3,5-Dihydroxy-cyclohexyl)-3-(2-fluoro-4-methoxy-phenyl)-7-(4-methoxyphenylamino)-3,4-dihydro-1H-pyrimido[4,5-d]pyrimidin-2-one,
1-(cis-3,5-Dihydroxy-cyclohexyl)-3-(4-methoxy-phenyl)-7-(4-methoxy-phenylamino)-3,4-dihydro-1H-pyrimido[4,5-d]pyrimidin-2-one,
1-(cis-3,5-Dihydroxy-cyclohexyl)-3-(4-methoxy-phenyl)-7-(4-fluoro-3-methoxy-phenylamino)-3,4-dihydro-1H-pyrimido[4,5-d]pyrimidin-2-one,
1-(cis-3,5-Dihydroxy-cyclohexyl)-3-(4-methoxy-phenyl)-7-phenylamino-3,4-dihydro-1H-pyrimido[4,5-d]pyrimidin-2-one, 1-(cis-3,5-Dihydroxy-cyclohexyl)-3-(2-fluoro-4-methoxy-phenyl)-7-phenylamino-3,4-dihydro-1H-pyrimido[4,5-d]pyrimidin-2-one,
1-(cis-3,5-Dihydroxy-cyclohexyl)-3-(2-fluoro-4-methoxy-phenyl)-7-(4-fluoro-3-methoxyphenylamino)-3,4-dihydro-1H-pyrimido[4,5-d]pyrimidin-2-one,
(R)-3-(4-Ethyl-phenyl)-7-(4-fluoro-phenylamino)-1-(2-hydroxy-1-methyl-ethyl)-3,4-dihydro-1H-pyrimido[4,5-d]pyrimidin-2-one,
(±)-3-(4-Ethyl-phenyl)-7-(4-fluoro-phenylamino)-1-(trans-3-hydroxy-cyclopentyl)-3,4-dihydro-1H-pyrimido[4,5-d]pyrimidin-2-one, and
1-Cyclopropylmethyl-3-(4-methoxy-phenyl)-7-phenylamino-3,4-dihydro-1H-pyrimido[4,5-d]pyrimidine-2-one.

24. A compound of formula

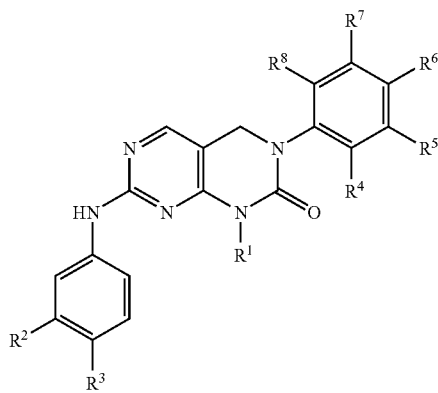

I wherein
$R^1$ is selected from
—H,
-lower alkyl substituted by —OH, $COR^{10}$, —CN or —$CONH_2$,
—$(CH_2)_n$-heterocycle,
—$(CH_2)_n$-heterocycle substituted by —$COR^{10}$, —$CO^2R^{10}$ or (=O)$_2$,
cycloalkyl,
cycloalkyl substituted by —OH;
$R^2$ is H or —$OCH_3$;
$R^3$ is H, F or —$OCH_3$;
$R^4$, $R^5$ and $R^7$ are H;
$R^6$ is —$OCH_3$ or lower alkyl;
$R^8$ is H or F H;
$R^{10}$ is lower alkyl substituted by alkoxy; and
n is 0 or 1.

25. A compound selected from the group:
4-[3-(4-Methoxy-phenyl)-2-oxo-7-phenylamino-3,4-dihydro-2H-pyrimido[4,5-d]pyrimidin-1-yl]-piperidine-1-carboxylic acid tert-butyl ester,
1-[trans-4-(tert-Butyl-dimethyl-silanyloxy)-cyclohexyl]-3-(4-methoxy-phenyl)-7-phenylamino-3,4-dihydro-1H-pyrimido[4,5-d]pyrimidin-2-one,
3-[3-(4-Methoxy-phenyl)-2-oxo-7-phenylamino-3,4-dihydro-2H-pyrimido[4,5-d]pyrimidin-1-yl]-piperidine-1-carboxylic acid tert-butyl ester,
(±)-3-cis-(tert-Butyl-dimethyl-silanyloxy)-cyclopentyl]-3-(4-methoxy-phenyl)-7-phenylamino-3,4-dihydro-1H-pyrimido[4,5-d]pyrimidin-2-one,
(R)-2-Methylsulfanyl-4-(tetrahydro-furan-3-ylamino)-pyrimidine-5-carboxylic acid ethyl ester,
(±)-4-[trans-3-(tert-Butyl-dimethyl-silanyloxy)-cyclopentylamino]-2-methylsulfanyl-pyrimidine-5-carbaldehyde,
(±)-1-[trans-3-(tert-Butyl-dimethyl-silanyloxy)-cyclopentyl]-3-(4-methoxy-phenyl)-7-methylsulfanyl-3,4-dihydro-1H-pyrimido[4,5-d]pyrimidin-2-one,
(±)-[3-trans-(tert-Butyl-dimethyl-silanyloxy)-cyclopentyl]-{5-[(2-fluoro-4-methoxy-phenylamino)-methyl]-2-methylsulfanyl-pyrimidin-4-yl}-amine,
(±)-1-[trans-3-(tert-Butyl-dimethyl-silanyloxy)-cyclopentyl]-3-(4-methoxy-phenyl)-7-methylsulfanyl-3,4-dihydro-1H-pyrimido[4,5-d]pyrimidin-2-one,
(S)-1-[2-(tert-Butyl-diphenyl-silanyloxy)-1-methyl-ethyl]-7-chloro-3-(4-methoxy-phenyl)-3,4-dihydro-1H-pyrimido[4,5-d]pyrimidin-2-one,
1-[trans-4-(tert-Butyl-dimethyl-silanyloxy)-cyclohexyl]-7-chloro-3-(2-fluoro-4-methoxy-phenyl)-3,4-dihydro-1H-pyrimido[4,5-d]pyrimidin-2-one,
1-[trans-4-(tert-Butyl-dimethyl-silanyloxy)-cyclohexyl]-7-chloro-3-(4-methoxy-phenyl)-3,4-dihydro-1H-pyrimido[4,5-d]pyrimidin-2-one,
1-[trans-4-(tert-Butyl-dimethyl-silanyloxy)-cyclohexyl]-3-(4-methoxy-phenyl)-7-(3,4-dimethoxy-phenylamino)-3,4-dihydro-1H-pyrimido[4,5-d]pyrimidin-2-one, and
1-[trans-4-(tert-Butyl-dimethyl-silanyloxy)-cyclohexyl]-3-(4-methoxy-phenyl)-7-(4-methoxy-phenylamino)-3,4-dihydro-1H-pyrimido[4,5-d]pyrimidin-2-one.

26. A compound selected from the group:
(S)-1-[2-(tert-Butyl-diphenyl-silanyloxy)-1-methyl-ethyl]-7-chloro-3-(2-fluoro-4-methoxy-phenyl)-3,4-dihydro-1H-pyrimido[4,5-d]pyrimidin-2-one,
(R)-1-[2-(tert-Butyl-diphenyl-silanyloxy)-1-methyl-ethyl]-7-chloro-3-(4-methoxy-phenyl)-3,4-dihydro-1H-pyrimido[4,5-d]pyrimidin-2-one,
3-(4-Methoxy-phenyl)-7-phenylamino-3,4-dihydro-1H-pyrimido[4,5-d]pyrimidine-2-one,
(+)-(1R, 3R)-4-[3-(tert-Butyl-dimethyl-silanyloxy)-cyclopentylamino]-2-methylsulfanyl-pyrimidine-5-carboxylic acid ethyl ester,
(−)-(1R,3R)-1-[3-(tert-Butyl-dimethyl-silanyloxy)-cyclopentyl]-3-(4-methoxy-phenyl)-7-phenylamino-3,4-dihydro-1H-pyrimido[4,5-d]pyrimidin-2-one,
(R)-1-[2-(tert-Butyl-diphenyl-silanyloxy)-propyl]-7-chloro-3-(4-methoxy-phenyl)-3,4-dihydro-1H-pyrimido[4,5-d]pyrimidin-2-one,
(−)-(1S,3S)-4-[3-(tert-Butyl-dimethyl-silanyloxy)-cyclopentylamino]-2-methylsulfanyl-pyrimidine-5-carboxylic acid ethyl ester,
(−)-(1S,3S)-4-[3-(tert-Butyl-dimethyl-silanyloxy)-cyclopentylamino]-2-methylsulfanyl-pyrimidine-5-carbaldehyde,
(−)-(1S,3S)-1-[3-(tert-Butyl-dimethyl-silanyloxy)-cyclopentyl]-3-(4-methoxy-phenyl)-7-methylsulfanyl-3,4-dihydro-1H-pyrimido[4,5-d]pyrimidin-2-one,
(−)-(1S,3S)-1-[3-(tert-Butyl-dimethyl-silanyloxy)-cyclopentyl]-3-(4-methoxy-phenyl)-7-phenylamino-3,4-dihydro-1H-pyrimido[4,5-d]pyrimidin-2-one,
(S)-1-[2-(tert-Butyl-diphenyl-silanyloxy)-propyl]-7-chloro-3-(4-methoxy-phenyl)-3,4-dihydro-1H-pyrimido[4,5-d]pyrimidin-2-one,
1-[cis-3,5-Bis-(tert-butyl-diphenyl-silanyloxy)-cyclohexyl]-7-chloro-3-(2-fluoro-4-methoxy-phenyl)-3,4-dihydro-1H-pyrimido[4,5-d]pyrimidin-2-one, 1-[cis-3,5-Bis-(tert-butyl-diphenyl-silanyloxy)-cyclohexyl]-3-(2-fluoro-4-methoxy-phenyl)-7-(4-methoxy-phenylamino)-3,4-dihydro-1H-pyrimido[4,5-d]pyrimidin-2-one, and 1-[cis-3,5-Bis-(tert-butyl-diphenyl-silanyloxy)-cyclohexyl]-7-chloro-3-(4-methoxy-phenyl)-3,4-dihydro-1H-pyrimido[4,5-d]pyrimidin-2-one.

27. A compound selected from the group:

1-[cis-3,5-Bis-(tert-butyl-diphenyl-silanyloxy)-cyclohexyl]-3-(4-methoxy-phenyl)-7-(4-methoxy-phenylamino)-3,4-dihydro-1H-pyrimido[4,5-d]pyrimidin-2-one, 1-[cis-3,5-Bis-(tert-butyl-diphenyl-silanyloxy)-cyclohexyl]-3-(4-methoxy-phenyl)-7-(4-fluoro-3-methoxy-phenylamino)-3,4-dihydro-1H-pyrimido[4,5-d]pyrimidin-2-one, 1-[cis-3,5-Bis-(tert-butyl-diphenyl-silanyloxy)-cyclohexyl]-3-(4-methoxy-phenyl)-7-phenylamino-3,4-dihydro-1H-pyrimido[4,5-d]pyrimidin-2-one, 1-[cis-3,5-Bis-(tert-butyl-diphenyl-silanyloxy)-cyclohexyl]-3-(2-fluoro-4-methoxy-phenyl)-7-phenylamino-3,4-dihydro-1H-pyrimido[4,5-d]pyrimidin-2-one, 1-[cis-3,5-Bis-(tert-butyl-diphenyl-silanyloxy)-cyclohexyl]-3-(2-fluoro-4-methoxy-phenyl)-7-(4-fluoro-3-methoxy-phenylamino)-3,4-dihydro-1H-pyrimido[4,5-d]pyrimidin-2-one, (2,4-Dichloro-pyrimidin-5-ylmethyl)-(4-ethyl-phenyl)-amine, (R)-3-[2-(tert-Butyl-dimethyl-silanyloxy)-1-methyl-ethyl]-1-(2,4-dichloro-pyrimidin-5-ylmethyl)-1-(4-ethyl-phenyl)-urea, (R)-1-[2-(tert-Butyl-dimethyl-silanyloxy)-1-methyl-ethyl]-7-chloro-3-(4-ethyl-phenyl)-3,4-dihydro-1H-pyrimido[4,5-d]pyrimidin-2-one, (R)-1-[2-(tert-Butyl-dimethyl-silanyloxy)-1-methyl-ethyl]-3-(4-ethyl-phenyl)-7-(4-fluoro-phenylamino)-3,4-dihydro-1H-pyrimido[4,5-d]pyrimidin-2-one, (±)-[trans-3-(tert-Butyl-dimethyl-silanyloxy)-cyclopentyl]-{2-chloro-5-[(4-ethyl-phenylamino)-methyl]-pyrimidin-4-yl}-amine, (±)-1-[trans-3-(tert-Butyl-dimethyl-silanyloxy)-cyclopentyl]-7-chloro-3-(4-ethyl-phenyl)-3,4-dihydro-1H-pyrimido[4,5-d]pyrimidin-2-one, and (±)-1-[trans-3-(tert-Butyl-dimethyl-silanyloxy)-cyclopentyl]-3-(4-ethyl-phenyl)-7-(4-fluoro-phenylamino)-3,4-dihydro-1H-pyrimido[4,5-d]pyrimidin-2-one.

28. A pharmaceutical composition comprising a therapeutically effective amount of a compound of claim 1 and pharmaceutically acceptable carrier or excipient.

29. A method for treating breast, lung, colon or prostate cancer comprising administering to a patient in need of such treatment a therapeutically effective amount of a compound of claim 1.

30. A method of controlling breast, lung, colon or prostate cancer comprising administering to a patient in need of such treatment a therapeutically effective amount of a compound of claim 1.

* * * * *

UNITED STATES PATENT AND TRADEMARK OFFICE
CERTIFICATE OF CORRECTION

PATENT NO. : 7,115,740 B2  Page 1 of 1
APPLICATION NO. : 10/817697
DATED : October 3, 2006
INVENTOR(S) : Chen et al.

It is certified that error appears in the above-identified patent and that said Letters Patent is hereby corrected as shown below:

IN THE CLAIMS:

Claim 1, Column 96, line 1: delete the word "-alkyl,".

Signed and Sealed this

Twenty-eighth Day of August, 2007

JON W. DUDAS
*Director of the United States Patent and Trademark Office*